United States Patent [19]

Armistead et al.

[11] Patent Number: 5,723,459
[45] Date of Patent: Mar. 3, 1998

[54] BIOLOGICALLY ACTIVE ACYLATED AMINO ACID DERIVATIVES

[75] Inventors: David M. Armistead, Maynard; Matthew W. Harding; Jeffrey O. Saunders, both of Acton; Joshua S. Boger, Concord, all of Mass.

[73] Assignee: Vertex Pharmaceuticals Incorporated, Cambridge, Mass.

[21] Appl. No.: 377,315

[22] Filed: Jan. 24, 1995

Related U.S. Application Data

[63] Continuation-in-part of Ser. No. 217,982, Mar. 25, 1994, Pat. No. 5,620,971, and Ser. No. 881,152, May 11, 1992, abandoned, which is a continuation-in-part of Ser. No. 697,785, May 9, 1991, abandoned, said Ser. No. 217,982, is a continuation-in-part of Ser. No. 127,814, Sep. 28, 1993, abandoned, which is a continuation-in-part of Ser. No. 952,299, Sep. 28, 1992, abandoned.

[51] Int. Cl.$^6$ .................. A61K 31/54; A61K 31/535; C07D 401/02; C07D 403/02

[52] U.S. Cl. .................. 514/237.8; 514/261; 514/357; 514/538; 514/541; 560/41; 544/162; 544/277; 546/335

[58] Field of Search .................. 546/335; 544/277, 544/162; 560/41; 514/357, 261, 237.8, 538, 541

[56] References Cited

U.S. PATENT DOCUMENTS

| | | | |
|---|---|---|---|
| 4,296,113 | 10/1981 | Ondetti | 424/246 |
| 4,376,124 | 3/1983 | Carlson | 514/569 |
| 4,579,840 | 4/1986 | Hahn | 530/327 |
| 4,920,218 | 4/1990 | Askin | 540/456 |
| 5,135,915 | 8/1992 | Czarniecki | 530/399 |
| 5,192,773 | 3/1993 | Armistead | 514/330 |
| 5,274,167 | 12/1993 | Lange et al. | 560/40 |
| 5,330,993 | 7/1994 | Armistead | 514/315 |

FOREIGN PATENT DOCUMENTS

| | | |
|---|---|---|
| A-0172458 | 2/1986 | European Pat. Off. |
| A-0384341 | 8/1990 | European Pat. Off. |
| A-0457163 | 11/1991 | European Pat. Off. |
| WO 92/00278 | 1/1992 | WIPO |

OTHER PUBLICATIONS

D. R. Bender et al., "Periodate Oxidation of α–Ketoy–Lactams. Enol Oxidation and β–Lactam Formation. Mechanism of Periodate Hydroxylation Reactions", *J. Org. Chem.*, 43(17), pp. 3354–3361 (1978).

D. Boesch et al., "In Vivo Circumvention of P–Glycoprotein–Mediated Multidrug Resistance of Tumor Cells with SDZ PSC 833", *Cancer Res.*, 51, pp. 4226–4233 (1991).

S.P.C. Cole et al., "Overexpression of a Transporter Gene in a Multidrug Resistant Human Lung Cancer Cell Line", *Science*, 258, pp. 1650–1654 (1992).

R.F. Epand and R.M. Epand, "The New Potent Immunosuppressant FK–506 Reverses Multidrug Resistance in Chinese Hamster Ovary Cells", *Anti–Cancer Drug Design* 6, pp. 189–193 (1991).

W.N. Hait and D. T. Aftab, "Rational Design and Pre–Clinical Pharmacology of Drugs for Reversing Multidrug Resistance", *Biochem. Pharmacol.*, 43, pp. 103–107 (1992).

W. N. Hait et al., "Activity of Cyclosporin A and a Non–Immunosuppressive Cyclosporin Against Multidrug Resistant Leukemic Cell Lines", *Cancer Commun.*, 1(1), pp. 35–43 (1989).

X.F. Hu et al., "Combined Use of Cyclosporin A and Verapamil in Modulating Multidrug Resistance in Human Leukemia Cell Lines", *Cancer Res.*, 50, pp. 2953–2957 (1990).

G. Jedlitschky et al., "ATP–Dependent Transport of Glutathione S–conjugates by the Multidrug Resistance–Associated Protein", *Cancer Res.*, 54, 4833–4836 (1994).

N. Krishnamachary et al., "The MRP Gene Associated with a Non–P–Glycoprotein Multidrug Resistance Encodes a 190–kDa Membrane Bound Glycoprotein", *Cancer Res.*, 53, 3658–3661 (1993).

I. Leier et al., "The MRP Gene Encodes an ATP–Dependent Export Pump for Leukotriene $C_4$ and Structurally Related Conjugates", *J.Biol.Chem.*, 269, pp. 27807–27810 (1994).

M. Muller et al., "Overexpression of the Gene Encoding the Multi–Drug Resistance–Associated Protein Results in Increased APT–Dependent Glutathione S–Conjugate Transport," *Proc. Natl. Acad. Sci. USA*, 91, pp. 13033–13037 (1994).

E. Schneider et al., "Multidrug Resistance–Associated Protein Gene Overexpression and Reduced Drug Sensitivity of Topoisomerase II in a Human Breast Carcinoma MCF7 Cell Line Selected for Etopside Resistance", *Cancer Res.*, 54, pp. 152–158 (1994).

L. M. Slater et al., "Cyclosporin A Corrects Daunorubicin Resistance in Ehrlich Ascites Carcinoma", *Br. J. Cancer*, 54, pp. 235–238 (1986).

K. Soai et al., "Asymmetric Allylation of α–Keto Amides Derived from (S)–Proline Esters", *Peptide Chemistry 1986, Proceedings of the 24th Symposium on Peptide Chemistry*, (T. Miyazawa, Ed., Protein Research Foundation) pp. 327–330 (1987).

P.R. Twentyman, "Cyclosporins as Drug Resistance Modifiers", *Biochem. Pharmacol.*, 43, pp. 109–117 (1992).

P.R. Twentyman et al., "Cyclosporin A and Its Analogues as Modifiers of Adriamycin and Vincristine Resistance in a Multi–drug Resistant Human Lung Cancer Cell Line", *Br.J. Cancer*, 56, pp. 55–57 (1987).

I.C. West, "What Determines the Substrate Specificity of the Multi–Drug–Resistance Pump?", *TIBS*, 15, pp. 42–46 (1990).

*Primary Examiner*—Matthew V. Grumbling
*Attorney, Agent, or Firm*—Fish & Neave; James F. Haley, Jr.; Andrew S. Marks

[57] ABSTRACT

The present invention relates to novel compounds which possess a broad range of useful biological activities. These compounds can maintain, increase, or restore sensitivity of cells to therapeutic or prophylactic agents. They can also suppress, modify, or significantly reduce an immune response, including an autoimmune response in a mammal. This invention also relates to pharmaceutical compositions comprising these compounds. The compounds and pharmaceutical compositions of this invention are particularly well-suited for treatment of multi-drug resistant cells, for prevention of the development of multi-drug resistance, for use in multi-drug resistant cancer therapy, and for prevention or treatment of graft rejection and various autoimmune diseases.

28 Claims, No Drawings

BIOLOGICALLY ACTIVE ACYLATED AMINO ACID DERIVATIVES

CROSS-REFERENCE TO RELATED APPLICATIONS

This is a continuation-in-part of U.S. application Ser. No. 08/217,982, filed Mar. 25, 1994, now U.S. Pat. No. 5,620,971, which is a continuation-in-part of U.S. application Ser. No. 08/127,814, filed Sep. 28, 1993, now abandoned, which is a continuation-in-part of Ser. No. 07/952,299, filed Sep. 28, 1992, now abandoned. This is also a continuation-in-part of U.S. application Ser. No. 07/881,152, filed May 11, 1992 abandoned as a continuation-in-part of Ser. No. 07/697,785, filed May 9, 1991, now abandoned.

TECHNICAL FIELD OF THE INVENTION

The present invention relates to novel compounds which possess a broad range of useful biological activities. These compounds can maintain, increase, or restore sensitivity of cells to therapeutic or prophylactic agents. They can also suppress or modify the immune response in humans and other mammals. This invention also relates to pharmaceutical compositions comprising these compounds. The compounds and pharmaceutical compositions of this invention are particularly well-suited for treatment of multi-drug resistant cells, for prevention of the development of multi-drug resistance and for use in multi-drug resistant cancer therapy. In addition, the compounds and pharmaceutical compositions of this invention are useful for prevention, suppression or reduction of graft rejection, as well as the treatment or prevention of autoimmune diseases.

BACKGROUND OF THE INVENTION

Two important areas of medicine are cancer chemotherapy and chemical modifications of the immune system. These have been the focus of much recent medical research.

A major problem affecting the efficacy of chemotherapy regimens is the evolution of cells which, upon exposure to a chemotherapeutic drug, become resistant to a multitude of structurally unrelated drugs and therapeutic agents. The appearance of such multi-drug resistance often occurs in the presence of overexpression of the 170-kDA membrane P-glycoprotein (gp-170). The gp-170 protein is present in the plasma membranes of some healthy tissues, in addition to cancer cell lines, and is homologous to bacterial transport proteins (Hait et al., *Cancer Communications*, Vol. 1(1), 35 (1989); West, TIBS, Vol. 15, 42 (1990)). The protein acts as an export pump, conferring drug resistance through active extrusion of toxic chemicals. Although the mechanism for the pump is unknown, it is speculated that the gp-170 protein functions by expelling substances that share certain chemical or physical characteristics, such as hydrophobicity, the presence of carbonyl groups, or the existence of a glutathione conjugate (see West).

Recently, another protein responsible for multidrug resistance, MRP (multidrug resistance associated protein), was identified in H69AR cells, an MDR cell line that lacks detectable P-glycoprotein [S. P. C. Cole et al., *Science*, 258, pp. 1650–54 (1992)]. MRP has also been detected in other non-P-glycoprtoein MDR cell lines, such as HL60/ADR and MCF-7 brast carcinoma cells [(E. Schneider et al., *Cancer Res.*, 54, pp. 152–58 (1994); and N. Krishnamachary et al., *Cancer Res.*, 53, pp. 3658–61 (1993)].

The MRP gene encodes a 190 kD membrane-associated protein that is another member of the ATP binding cassette superfamily. MRP appears to function in the same manner as P-glycoprotein, acting as a pump for removing natural product drugs from the cell. A possible physiological function for MRP maybe ATP-dependent transport of glutathione S-conjugates [G. Jedlitschky et al., *Cancer Res.*, 54, pp. 4833–36 (1994); I. Leier et al., *J. Biol. Chem.*, 269, pp. 27807–10 (1994); and Muller et al., *Proc. Natl. Acad. Sci. USA*, 91, pp. 13033–37 (1994)].

The role of MRP in clinical drug resistance remains to be clearly defined, but it appears likely that MRP may be another protein responsible for a broad resistance to anticancer drugs.

Various chemical agents have been administered to repress multi-drug resistance and restore drug sensitivity. While some drugs have improved the responsiveness of multi-drug resistant ("MDR") cells to chemotherapeutic agents, they have often been accompanied by undesirable clinical side effects (see Hait et al.). For example, although cyclosporin A ("CsA"), a widely accepted immunosuppressant, can sensitize certain carcinoma cells to chemotherapeutic agents (Slater et al., *Br. J. Cancer*, Vol. 54, 235 (1986)), the concentrations needed to achieve that effect produce significant immunosuppression in patients whose immune systems are already compromised by chemotherapy (see Hait et al.). In addition, CsA usage is often accompanied by adverse side effects including nephrotoxicity, hepatotoxicity and central nervous system disorders. Similarly, calcium transport blockers and calmodulin inhibitors both sensitize MDR cells, but each produces undesirable physiological effects (see Hait et al.; Twentyman et al., *Br. J. Cancer*, Vol. 56, 55 (1987)).

Recent developments have led to agents said to be of potentially greater clinical value in the sensitization of MDR cells. These agents include analogs of CsA which do not exert an immunosuppressive effect, such as 11-methyl-leucine cyclosporin (11-met-leu CsA) (see Hait et al.; Twentyman et al.), or agents that may be effective at low doses, such as the immunosuppressant FK-506 (Epand and Epand, *Anti-Cancer Drug Design* 6, 189 (1991)). Despite these developments, the need remains for effective agents which may be used to resensitize MDR cells to therapeutic or prophylactic agents or to prevent the development of multi-drug resistance.

A second significant medical objective constitutes the ability to modulate the immune system. For example, post operative graft rejections are a major complication affecting the success of bone marrow and organ transplantations. However, through the use of immunosuppressive drug therapy, graft rejection in organ transplantation can be significantly reduced. Immunosuppressive therapy may also be used in preventing or treating autoimmune diseases, which are similar to graft rejection, except that the rejection is of self tissue.

One widely accepted immunosuppressant for the prevention of graft rejection is CsA. A natural product of fungal metabolism, CsA has been demonstrated to have potent immunosuppressive activity in clinical organ transplantations. Calne, R. Y. et al., *Br. Med. J.*, Vol. 282, pp. 934–936 (1981); White, D. J. C., *Drugs*, Vol. 24, pp. 322–334 (1982).

Many disorders have been treated with cyclosporin A with positive results, confirming the importance of the autoimmune component in these diseases and their effective treatment with compounds working by selective T-cell immune suppression similar to cyclosporin A. These disorders include ophthalmological diseases, such as uveitis, Nussenblatt, R. B. et al., *Lancet*, pp. 235–238 (1983);

Behcet's disease,* French-Constant, C. et al., *Lancet*, p. 454 (1983); Sanders, M. et al., *Lancet*, pp. 454–455 (1983); and Grave's ophthalmopathy, Weetman, A. P. et al., *Lancet*, pp. 486–489 (1982).

* Cyclosporin A is currently approved in Japan for the treatment of Behcet's disease, the first autoimmune disease indication for this compound.

CsA has also been used in dermatological applications, including various autoimmune skin diseases, such as psoriasis, Ellis, C. N. et al., *J. Amer. Med. Assoc.*, Vol. 256, pp. 3110–3116 (1986); Griffiths, C. E. M. et al., *Brit. Med. J.*, Vol. 293, pp. 731–732 (1986); acute dermatomyositis, Zabel, P. et al., *Lancet*, p. 343 (1984); atopic skin disease, van Joost, T. et al., *Arch. Dermatol.*, Vol. 123, pp. 166–167 (1987); scleroderma, Appleboom, T. et al., *Amer. J. Med*, Vol. 82, pp. 866–867 (1987); and eczema, Logan, R. A. and Camo R. D. R., *J. Roy. Soc. Med.*, Vol. 81, pp. 417–418 (1988).

Various hematological diseases treated with CsA include anemia, such as aplastic anemia, Stryckmans, P. A. et al., *New Engl. J. Med.*, Vol. 310, pp. 655–656 (1984); and Gluckman, E. et al., *Bone Marrow Transplant*, Vol. 3 Suppl. 1, 241 (1988); and pure red cell aplasia (PRCA), Toetterman, T. H. et al., *Lancet*, p. 693 (1984).

CsA has also been used in the fields of gastroenterology and hepatology to treat primary cirrhosis, Wiesner, R. H. et al., *Hepatology*, Vol. 7, p. 1025, Abst. #9 (1987); autoimmune hepatitis, Hyams, J. S. et al., *Gastroenterolochy*, Vol. 93, pp. 890–893 (1987); ulcerative coliris, Porro, G. B. et al., *Ital. J. Gastroenterol.*, Vol. 19, pp. 40–41 (1987); Crohn's disease, Allison, M. C. et al., *Lancet*, pp. 902–903 (1984), and Brynskov, J. et al., *Gastroenterology*, Vol. 92, p. 1330 (1987); and other gastrointestinal autoimmune diseases.

Neurological applications of CsA include amyotrophic lateral sclerosis (ALS, "Lou Gehrig's disease"), Appel, S. H. et al., *Arch. Neurol.*, Vol. 45, pp. 381–386 (1988); myasthenia gravis, Tindall, R. S. A. et al., *New Engl. J. Med.*, Vol. 316, pp. 719–724 (1987); and multiple sclerosis, *Ann. Neurol.*, Vol. 24, No. 1, p. 169,m Abstract P174 (1988), and Dommasch, D. et al., *Neurology*, Vol. 38 Suppl. 2, pp. 28–29 (1988).

CsA has been used to treat nephrotic syndromes, membrano-proliferative glomerulonephritis (MPGN) and related diseases, Watzon, A. R. et al., *Clin. Nephrol.*, Vol. 25, pp. 273–274 (1986); Tejani, A. et al., *Kidney Int.*, Vol. 33, pp. 729–734 (1988); Meyrier, A. et al., *Transplat Proc.*, Vol. 20, Suppl. 4 (Book III), pp. 259–261 (1988); LaGrue, G. et al., *Nephron.*, Vol. 44, pp. 382–382 (1986).

In addition, CsA has been used to treat rheumatoid arthritis, Harper, J. I. et al., *Lancet*, pp. 981–982 (1984); Van Rijthoven, A. W. et al., *Ann. Rheum. Dis.*, Vol. 45, pp. 726–731 (1986), and Dougados, M. et al., *Ann Rheum. Dis.*, Vol. 47, pp. 127–133 (1988); and insulin-dependent diabetes mellitus (IDDM), Stiller, C. R. et al., *Science*, Vol. 233, pp. 1362–1367 (1984), Assan, R. et al., *Lancet*, pp. 67–71 (1985); Bougneres, P. F. et al., *New Engl. J. Med.*, Vol. 318, pp. 663–670 (1988), and *Diabetes*, Vol. 37, pp. 1574–1582 (1988).

Many veterinary diseases are also characterized as autoimmune diseases. Autoimmune diseases such as those discussed above have been observed in mammals. Papa, F. O. et al., *Equine Vet. J.*, Vol. 22, pp. 145–146 (1990)—infertility of autoimmune origin in the stallion; Gorman, N. T. and L. L. Werner, *Brit. Vet. J.*, Vol. 142, pp. 403–410, 491–497 and 498–505 (1986)—immune mediated diseases of cats and dogs; George, L. W. and S. L. White, *Vet. Clin. North Amer.*, Vol. 6, pp. 203–213 (1984)—autoimmune skin diseases in large mammals; Bennett, D., *In. Pract.*, Vol. 6, pp. 74–86 (1984)—autoimmune diseases in dogs; Halliwell, R. E., *J. Amer. Vet. Assoc.*, Vol. 181, pp. 1088–1096 (1982)—autoimmune diseases in domesticated animals.

The mechanism by which CsA causes immunosuppression has been established. In vitro, CsA inhibits the release of lymphokines, such as interleukin 2 (IL-2) [Bunjes, D. et al., *Eur. J. Immunol.*, Vol. 11, pp. 657–661 (1981)] and prevents clonal expansion of helper and cytotoxic T cells [Larsson, E., *J. Immunol.*, Vol. 124, pp. 2828–2833 (1980)]. CsA has been shown to bind the cytosolic protein, cyclophilin, and inhibit the prolyl-peptidyl cis-trans isomerase (PPIase) activity of that protein. Fischer, G. et al., *Nature*, Vol. 337, pp. 476–478 (1989); Takashaski, N. et al., *Nature*, Vol. 337, pp. 473–475 (1989).

Recently, a second natural product isolated from Streptomyces, referred to as FK-506, has been demonstrated to be a potent immunosuppressive agent. Tanaka, H. et al., *J. Am. Chem. Soc.*, Vol. 109, pp. 5031–5033 (1987). FK-506 inhibits IL-2 production, inhibits mixed lymphocyte culture response and inhibits cytotoxic T-cell generation in vitro at 100 times lower concentration than cyclosporin A. Kino, T. et al., *J. Antibiot.*, Vol. 15, pp. 1256–1265 (1987). FK-506 also inhibits PPIase activity, but is structurally different from CsA and binds to a binding protein (FKBP) distinct from cyclophilin. Harding, M. W. et al., *Nature*, Vol. 341, pp. 758–760 (1989); Siekierka, J. J., *Nature*, Vol. 341, pp. 755–757 (1989).

In view of the wide variety of disorders that may be alleviated by immunosuppression, and the scant number of available immunosuppressants, there remains a great need for novel immunosuppressive agents. Such agents may be used alone or serve as supplemental therapeutics to CsA and FK-506.

SUMMARY OF THE INVENTION

The present invention provides novel compounds that are useful to maintain, increase or restore drug sensitivity in multi-drug resistant ("MDR") cells, compositions containing those compounds and methods for using them. The compounds of this invention may be used alone or in combination with other therapeutic or prophylactic agents to maintain, increase or restore the therapeutic or prophylactic effects of drugs in cells, especially MDR cells, or to prevent the development of MDR cells. According to one embodiment of this invention, these novel compounds, compositions and methods are advantageously used to aid or enhance chemotherapy regimens for the treatment or prophylaxis of cancer and other diseases.

The novel compounds of this invention are also useful to prevent, suppress or significantly reduce an immune response in a mammal. Their ability to bind to the FK-506 binding protein (FKBP) allows immunosuppressive compounds of this invention, once bound to FKBP, to inhibit T-cell activation. Thus, the compounds of this invention can also be used as immunosuppressive drugs to prevent or significantly reduce graft rejection in bone marrow and organ transplantations and in the treatment or prevention of autoimmune diseases in humans and other mammals.

The present invention also provides methods for preparing the compounds of this invention and intermediates useful in those methods.

DETAILED DESCRIPTION OF THE INVENTION

This invention relates to a novel class of compounds represented by the formula (I):

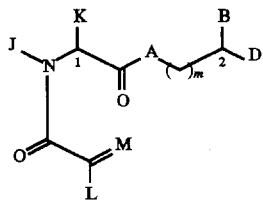

wherein A is $CH_2$, oxygen, NH or N—(C1–C4 alkyl);
wherein B and D are independently (i) hydrogen, Ar, (C1–C10)-straight or branched alkyl, (C2–C10)-straight or branched alkenyl or alkynyl, (C5–C7)-cycloalkyl substituted (C1–C6)-straight or branched alkyl, (C2–C6)-straight or branched alkenyl or alkynyl, (C5–C7)-cycloalkenyl substituted (C1–C6)-straight or branched alkyl, (C2–C6)-straight or branched alkenyl or alkynyl, or Ar substituted (C1–C6)-straight or branched alkyl, (C2–C6)-straight or branched alkenyl or alkynyl wherein, in each case, any one of the $CH_2$ groups of said alkyl, alkenyl or alkynyl chains may be optionally replaced by a heteroatom selected from the group consisting of O, S, SO, $SO_2$, N, and NR, wherein R is selected from the group consisting of hydrogen, (C1–C4)-straight or branched alkyl, (C2–C4)-straight or branched alkenyl or alkynyl, and (C1–C4) bridging alkyl wherein a bridge is formed between the nitrogen and a carbon atom of said heteroatom-containing chain to form a ring, and wherein said ring is optionally fused to an Ar group; or (ii) 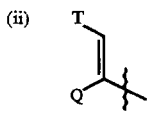

wherein Q is hydrogen, (C1–C6)-straight or branched alkyl or (C2–C6)-straight or branched alkenyl or alkynyl;

wherein T is Ar or substituted 5–7 membered cycloalkyl with substituents at positions 3 and 4 which are independently selected from the group consisting of oxo, hydrogen, hydroxyl, O—(C1–C4)-alkyl, and O—(C2–C4)-alkenyl;

wherein Ar is a carbocyclic aromatic group selected from the group consisting of phenyl, 1-naphthyl, 2-naphthyl, indenyl, azulenyl, fluorenyl, anthracenyl, and mono and bicyclic heterocyclic ring systems with individual ring sizes being 5 or 6 which may contain in either or both rings a total of 1–4 heteroatoms independently selected from oxygen, nitrogen, and sulfur—such ring systems include heterocyclic aromatic groups selected from the group consisting of 2-furyl, 3-furyl, 2-thienyl, 3-thienyl, 2-pyridyl, 3-pyridyl, 4-pyridyl, pyrrolyl, oxazolyl, thiazolyl, imidazolyl, pyraxolyl, 2-pyrazolinyl, pyrazolidinyl, isoxazolyl, isotiazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolylo, isoindolyl, 3H-indolyl, indolinyl, benzo[b]furanyl, benzo[b]thiophenyl, 1H-indazolyl, benzimidazolyl, benzthiazolyl, purinyl, 4H-quinolizinyl, quinolinyl, isoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl, and phenoxazinyl;

wherein Ar may contain one to three substituents which are independently selected from the group consisting of hydrogen, halogen, hydroxyl, nitro, trifluoromethyl, trifluoromethoxy, (C1–C6)-straight or branched alkyl, (C2–C6)-straight or branched alkenyl, O—(C1–C4)-straight or branched alkyl, O—(C2–C4)-straight or branched alkenyl, O-benzyl, O-phenyl, 1,2-methylenedioxy, amino, carboxyl, N—(C1–C5-straight or branched alkyl or alkenyl)carboxamides, N,N-di-(C1–C5-straight or branched alkyl or C2–C5-straight or branched alkenyl)carboxamides, N-morpholinocarboxamide, N-benzylcarboxamide, N-thiomorpholinocarboxamide, N-picolinoylcarboxamide, O—X, $CH_2$—$(CH_2)_q$—X, O—$(CH_2)_q$—X, $(CH_2)_q$—O—X, and CH=CH—X; wherein X is 4-methoxyphenyl, 2-pyridyl, 3-pyridyl, 4-pyridyl, pyrazyl, quinolyl, 3,5-dimethylisoxazoyl, isoxazoyl, 2-methylthiazoyl, thiazoyl, 2-thienyl, 3-thienyl, or pyrimidyl, and q is 0–2;

wherein L is U; M is either oxygen or CH—U, provided that if L is hydrogen, then M is CH—U or if M is oxygen then L is not hydrogen;

wherein U is hydrogen, O—(C1–C4)-straight or branched alkyl or O—(C2–C4)straight or branched alkenyl, (C1–C6)-straight or branched alkyl or (C2–C6)-straight or branched alkenyl, (C5–C7)-cycloalkyl or (C5–C7)-cycloalkenyl substituted with (C1–C4)-straight or branched alkyl or (C2–C4)-straight or branched alkenyl, [(C1–C4)-alkyl or (C2–C4)-alkenyl]—Y or Y;

wherein Y is selected from the group consisting of phenyl, 1-naphthyl, 2-naphthyl, indenyl, azulenyl, fluorenyl, anthracenyl, 2-pyrrolinyl, 3-pyrrolinyl, pyrolidinyl, 1,3-dioxolyl, 2-imidazolinyl, imidazolidinyl, 2H-pyranyl, 4H-pyranyl, piperidyl, 1,4-dioxanyl, morpholinyl, 1,4-dithianyl, thiomorpholinyl, piperazinyl, quinuclidinyl, and heterocyclic aromatic groups as defined above;

where Y may contain one to three substituents which are independently selected from the group consisting of hydrogen, halogen, hydroxyl, hydroxymethyl, nitro, trifluoromethyl, trifluoromethoxy, (C1–C6)-straight or branched alkyl, (C1–C6)-straight or branched alkenyl, O—(C1–C4)-straight or branched alkyl, O—(C2–C4)-straight or branched alkenyl, O-benzyl, O-phenyl, 1,2-methylenedioxy, amino, and carboxyl;

wherein J is hydrogen, (C1–C2)alkyl or benzyl; K is (C1–C4)-straight or branched alkyl, benzyl or cyclohexylmethyl, or wherein J and K may be taken together to form a 5–7 membered heterocyclic ring which may contain a heteroatom selected from the group consisting of O, S, SO and $SO_2$; and wherein m is 0–3.

The stereochemistry at positions 1 and 2 (formula I) may be independently R or S.

In one embodiment of this invention, B and D are independently Ar, (C5–C7)-cycloalkyl substituted (C1–C6)-straight or branched alkyl or (C2–C6)-straight or branched alkenyl, (C5–C7)-cycloalkenyl substituted (C1–C6)-straight or branched alkyl or (C2–C6)-straight or branched alkenyl, or Ar substituted (C1–C6)-straight or branched alkyl or (C2–C6)-straight of branched alkenyl, wherein in each case, any one of the $CH_2$ groups of said alkyl or alkenyl chains is optionally replaced by a heteroatom selected from the group consisting of oxygen, sulfur, SO and $SO_2$; or

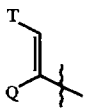

(T and Q as defined above);

and Ar is selected from the group consisting of phenyl, 1-naphthyl, 2-naphtyl, 2-furyl, 3-furyl, 2-thienyl, 3-thienyl, 2-pyridyl, 3-pyridyl, 4-pyridyl, monocyclic and bicyclic heterocyclic ring systems with individual ring sizes being 5 or 6 which may contain in either or both rings a total of 1–4 heteroatoms independently selected from oxygen, nitrogen and sulfur; wherein Ar may contain one to three substituents which are independently selected from the group consisting of hydrogen, halogen, hydroxyl, nitro, trifluoromethyl, trifluoromethoxy, (C1–C6)-straight or branched alkyl, (C1–C6)-straight or branched alkenyl, O—(C1–C4)-straight or branched alkyl, O—(C2–C4)-straight or branched alkenyl, O-benzyl, O-phenyl, 1,2-methylenedioxy, amino, carboxyl and phenyl;

and U is hydrogen, O—(C1–C4)-straight or branched alkyl, O—(C1–C4)-straight or branched alkenyl, (C1–C6)-straight or branched alkyl, (C1–C6)-straight or branched alkenyl, (C5–C7)-cycloalkyl, (C5–C7)-cycloalkenyl substituted with (C1–C4)-straight or branched alkyl or (C2–C4)-straight or branched alkenyl, [(C1–C4)-alkyl or (C2–C4)-alkenyl]—Ar or Ar (Ar as defined above). In another embodiment of this invention, the Ar group in the previous paragraph may also contain a hydroxymethyl substituent.

Preferably, at least one of B or D is independently a straight chain terminated by an aryl group, i.e., a group represented by the formula $(CH_2)_r$—(X)—$(CH_2)_s$—Ar, wherein
r is 0–4;

s is 0–1;

Ar is as defined for formula (I); and each X is independently selected from the group consisting of $CH_2$, O, S, SO, $SO_2$, N, and NR, wherein R is selected from the group consisting of hydrogen, (C1–C4)-straight or branched alkyl, (C2–C4)-straight or branched alkenyl or alkynyl, and (C1–C4) bridging alkyl wherein a bridge is formed between the nitrogen atom and the Ar group.

According to one embodiment of this invention, the heterocyclic aromatic groups are selected from the group consisting of furan, thiophene, pyrrole, pyridine, indolizine, indole, isoindole, benzo[b]furan, benzo[b]thiophene, 4H-quinolizine, quinoline, isoquinoline, 1,2,3,4-tetrahydroquinoline, isoxazole, and 1,2,3,4-tetrahydroisoquinoline.

According to another embodiment of this invention, at least one of B or D is selected from the group consisting of (C2–C10)-straight or branched alkynyl, (C5–C7)-cycloalkyl substituted (C2–C6)-straight or branched alkynyl, (C5–C7)-cycloalkenyl substituted (C2–C6)-straight or branched alkynyl, and Ar substituted (C2–C6)-straight or branched alkynyl.

Also within the scope of this invention are compounds of formula (I), wherein at least one of B or D is selected from the group consisting of Ar', Ar'-substituted (C1–C6)-straight or branched alkyl, and Ar'-substituted (C2–C6)-straight or branched alkenyl or alkynyl; wherein Ar' is an Ar group substituted with one to three substituents which are independently selected from the group consisting of N-(straight or branched C1–C5 alkyl or C2–C5 alkenyl)carboxamides, N,N-di-(straight or branched C1–C5 alkyl or C2–C5 alkenyl)carboxamides, N-morpholinocarboxamide, N-benzylcarboxamide, N-thiomorpholinocarboxamide, N-picolinoylcarboxamide, O—X, $CH_2$—$(CH_2)_q$—X, O—$(CH_2)_q$—X, $(CH_2)_q$—O—X, and CH=CH—X; wherein X is 4-methoxyphenyl, 2-pyridyl, 3-pyridyl, 4-pyridyl, pyrazyl, quinolyl, 3,5-di-methylisoxazoyl, isoxazoyl, 2-methylthiazoyl, thiazoyl, 2-thienyl, 3-thienyl, and pyrimidyl, and wherein q is 0–2.

Examples of some preferred compounds of formula (I), wherein J and K are taken together to form a 5–7 membered heterocyclic ring, are shown in Table 1 and are further illustrated in the examples herein.

TABLE 1

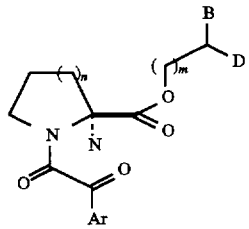

| Cpd. | n | m | B | D | Ar |
|---|---|---|---|---|---|
| 2 | 1 | 0 | 3-(Pyridin-2-yl)propyl | 3-Phenylpropyl | 3,4,5-Trimethoxyphenyl |
| 3 | 2 | 0 | 3-Phenylpropyl | 3-Phenylpropyl | 3,4,5-Trimethoxyphenyl |
| 4 | 2 | 0 | 2-Phenoxyphenyl | 3-Phenylpropyl | 3,4,5-Trimethoxyphenyl |
| 5 | 2 | 0 | Phenyl | 2-Phenoxyphenyl | 3,4,5-Trimethoxyphenyl |
| 6 | 2 | 0 | Phenyl | 3-Phenylpropyl | 3,4,5-Trimethoxyphenyl |
| 7 | 2 | 0 | 2-(Pyridin-3-yl)ethyl | 3-Phenylpropyl | 3,4,5-Trimethoxyphenyl |

TABLE 1-continued

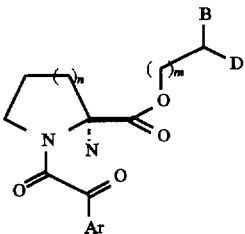

| Cpd. | n | m | B | D | Ar |
|---|---|---|---|---|---|
| 8 | 2 | 0 | E-3-[trans-(4-Hydroxycyclohexyl)]-2-methyl-eth-2-enyl | 3-Phenylpropyl | 3,4,5-Trimethoxyphenyl |
| 9 | 2 | 0 | 3-(Pyridin-3-yl)propyl | 3-Phenylpropyl | 3,4,5-Trimethoxyphenyl |
| 10 | 2 | 0 | Benzyl | 3-Phenylpropyl | 3,4,5-Trimethoxyphenyl |
| 11 | 2 | 0 | Benzyl | 3-(Indol-3-yl)propyl | 3,4,5-Trimethoxyphenyl |
| 12 | 2 | 0 | 2-Phenylethyl | 3-Phenylpropyl | 3,4,5-Trimethoxyphenyl |
| 13 | 2 | 0 | 2-(4-Methoxyphenyl)ethyl | 3-Phenylpropyl | 3,4,5-Trimethoxyphenyl |
| 14 | 2 | 0 | 2-(4-Methoxyphenyl)ethyl | 3-Phenylpropyl | Phenyl |
| 15 | 2 | 0 | 3-(N-Benzimidazolyl)propyl | 3-Phenylpropyl | 3,4,5-Trimethoxyphenyl |
| 16 | 2 | 1 | Benzyl | 2-Phenylethyl | 3,4,5-Trimethoxyphenyl |
| 17 | 2 | 0 | 3-(4-Methoxyphenyl)propyl | 3-Phenylpropyl | 3,4,5-Trimethoxyphenyl |
| 18 | 2 | 0 | 3-(Pyridin-3-yl)propyl | 3-Phenylpropyl | Phenyl |
| 19 | 2 | 0 | 3-(Pyridin-2-yl)propyl | 3-Phenylpropyl | Phenyl |
| 20 | 2 | 0 | 3-(Pyridin-2-yl)propyl | 3-Phenylpropyl | 3,4,5-Trimethoxyphenyl |
| 21 | 2 | 0 | 3-(Pyridin-2-yl)propyl | 3-Phenylpropyl | tert-Butyl |
| 22 | 2 | 0 | 3-(Pyridin-3-yl)propyl N-oxide | 3-Phenylpropyl | 3,4,5-Tdmethoxyphenyl |
| 23 | 2 | 0 | 3-lN-(7-Azaindolyl)-propyl | 3-Phenylpropyl | 3,4,5-Trimethoxyphenyl |
| 24 | 2 | 0 | 3-(Pyridin-3-yl)-propyl | 3-(4-Mathoxyphenyl)propyl) | 3,4,5-Trimethoxyphenyl |
| 25 | 2 | 0 | 3-(N-Purinyl)propyl | 3-Phenylpropyl | 3,4,5-Trimethoxyphenyl |
| 26 | 2 | 0 | 3-(4-Hydroxymethylphenyl)propyl | 3-Phenylpropyl | 3,4,5-Trimethoxyphenyl |
| 27 | 2 | 0 | 3-(Pyridin-3-yl)-propyl | 3-Phenylpropyl | 3-Benzyloxyphenyl |
| 28 | 2 | 0 | 3-(Pyridin-3-yl)propyl | 3-Phenylpropyl | 3-Allyloxyphenyl |
| 29 | 2 | 0 | 3-(Pyridin-3-yi)propyl | 3-Phenylpropyl | 3-Isopropoxyphenyl |
| 30 | 2 | 0 | 3-(Thiophen-2-yl)propyl | 3-Phenylpropyl | 3,4,5-Trimethoxyphenyl |
| 31 | 2 | 0 | 3-(4-Carboxyphenyi)propyl | 3-Phenylpropyl | 3,4,5-Trimethoxyphenyl |
| 32 | 2 | 0 | 3-Phenylbutyl | 3-Phenylpropyl | 3,4,5-Trimethoxyphenyl |
| 33 | 2 | 0 | 2-Hydroxymethylphenyl | 3-Phenylpropyl | 3,4,5-Trimethoxyphenyl |
| 34 | 2 | 0 | 2-Allyloxyphenyl | 3-Phenylpropyl | 3,4,5-Trimethoxyphenyl |
| 35 | 2 | 0 | 3-(3-Hydroxymethylphenyl)propyl | 3-Phenylpropyl | 3,4,5-Trimethoxyphenyl |
| 36 | 2 | 0 | 3-(3-Carboxyphenyl)propyl | 3-Phenylpropyl | 3,4,5-Trimethoxyphenyl |
| 37 | 2 | 0 | 3-Hydroxymethylphenyl | 3-Phenylpropyl | 3,4,5-Trimethoxyphenyl |
| 38 | 2 | 0 | 2-Hydroxypheny | 3-Phenylpropyl | 3,4,5-Trimethoxyphenyl |
| 39 | 2 | 0 | Pyridin-3-yi | 3-Phenylpropyl | 3,4,5-Trimethoxyphenyl |
| 40 | 2 | 0 | 3-(Thiopen-2-yl)propyl | 4-Phenylbutyl | 3,4,5-Trimethoxyphenyl |
| 41 | 2 | 0 | 5-Phenylpentyl | 3-Phenylpropyl | 3,4,5-Trimethoxyphenyl |

TABLE 1-continued

| Cpd. | n | m | B | D | Ar |
|---|---|---|---|---|---|
| 42 | 2 | 0 | 3-Allyloxypropyl | 3-Phenylpropyl | 3,4,5-Trimethoxyphenyl |
| 43 | 2 | 0 | 3-[4-(N,N-Di methylamine-carbonyl)-phenyl]propyl | 3-Phenylpropyl | 3,4,5-Trimethoxyphenyl |
| 44 | 2 | 0 | 3-14-(Morpholine-4-carbonyl)phenyl propyl | 3-Phenylpropyl | 3,4,5-Trimethoxyphenyl |
| 45 | 2 | 0 | 4-Alllyoxybutyl | 3-Phenylpropyl | 3,4,5-Trimethoxyphenyl |
| 46 | 2 | 0 | 3-Allyloxy-prop-1-ynyl | 3-Phenylpropyl | 3,4,5-Trimethoxyphenyl |
| 47 | 2 | 0 | 3-[4-(Piperidine-1-carbonyl)phenyl)-propyl | 3-Phenylpropyl | 3,4,5-Trimethoxyphenyl |
| 48 | 2 | 0 | 5-Allyloxynonyl | 3-Phenylpropyl | 3,4,5-Trimethoxyphenyl |
| 49 | 2 | 0 | Methyl | 3,5-Bis(benzyloxy)phenyl | 3,4,5-Trimethoxyphenyl |
| 50 | 2 | 0 | 2-Allyloxyethyl | 3-Phenylpropyl | 3,4,5-Trimethoxyphenyl |
| 51 | 2 | 0 | 3-Allyloxy-(E)-prop-l-onyl | 3-Phenylpropyl | 3,4,5-Trimethoxyphenyl |
| 52 | 2 | 0 | 3-13-(Morpholine-4-carbonyl)phenyl]propyl | 3-Phenylpropyl | 3,4,5-Trimethoxyphenyl |
| 53 | 2 | 0 | Dec-9-enyl | 3-Phenylpropyl | 3,4,5-Trimethoxyphenyl |
| 54 | 2 | 0 | 3-[4-(N-Benzyl-aminecarbonyl)-phenyl]propyl | 3-Phenylpropyl | 3,4,5-Trimethoxyphenyl |
| 55 | 2 | 0 | 3-[4-(Thiomorpholine-4-carbonyl)-phenyl]propyl | 3-Phenylpropyl | 3,4,5-Trimethoxyphenyl |
| 56 | 2 | 0 | 3-(Morpholine-4-carbonyl)phenyl- | 3-Phenylpropyl | 3,4,5-Trimethoxyphenyl |
| 57 | 2 | 0 | 3-[4-(1-Methyl-piperazine-4-carbonyl)-phenyl]propyl | 3-Phenylpropyl | 3,4,5-Trimethoxyphenyl |
| 58 | 2 | 0 | 3-[4-(1-Benzyl-piperazine-4-carbonyl)-phenyl]propyl | 3-Phenylpropyl | 3,4,5-Trimethoxyphenyl |
| 59 | 2 | 0 | 3-[3-(N-Benzyl-aminocarbonyl)-phenyl]propyl | 3-Phenylpropyl | 3,4,5-Trimethoxyphenyl |
| 60 | 2 | 0 | 3-[4-(N-Pyridin-2-ylaminecarbonyl)-phenyl]propyl | 3-Phenylpropyl | 3,4,5-Trimethoxyphenyl |
| 61 | 2 | 0 | Pyridin-3-yl | 3-(Pyridin-3-yl)-propyl | 3,4,5-Trimethoxyphenyl |
| 62 | 2 | 0 | Prop-2-enyl | 3,4-Bis-(Pyridin-4-ylmethoxy)phenyl | 3,4,5-Trimethoxyphenyl |
| 63 | 2 | 0 | Pyridin-3-yl | 3-(Pyridin-4-ylmethoxy)phenyl | 3,4,5-Trimethoxyphenyl |
| 64 | 2 | 0 | 3-Phenylpropyl | 3-(Pyridin-4-ylmethoxy)phenyl | 3,4,5-Trimethoxyphenyl |
| 65 | 2 | 0 | 3-Phenylpropyl | 3,4-Bis-(Pyridin-4-ylmethoxy)phenyl | 3,4,5-Trimethoxyphenyl |
| 66 | 2 | 0 | Methyl | 3,4-Bis-(Pyridin-4-ylmethoxy)phenyl | 3,4,5-Trimethoxyphenyl |
| 67 | 2 | 0 | 3-Phenylpropyl | 2,3,4-Tris-(Pyridin-4-ylmethoxy)phenyl | 3,4,5-Trimethoxyphenyl |
| 68 | 2 | 0 | 3-Phenylpropyl | 3-(Morpholine-4-carbonyl)-4-(Pyridin-4-ylmethoxy)phenyl | 3,4,5-Trimethoxyphenyl |
| 69 | 2 | 0 | Methyl | 3,4,5-Tris-(Pyridin-4-ylmethoxy)phenyl | 3,4,5-Trimethoxyphenyl |

TABLE 1-continued

| Cpd. | n | m | B | D | Ar |
|---|---|---|---|---|---|
| 70 | 2 | 0 | 3-Phenylpropyl | 3,4,5-Tris-(Pyridin-4-ylmethoxy)phenyl | 3,4,5-Trimethoxyphenyl |
| 71 | 2 | 0 | Methyl | 3,5-Bis-(Pyridin-4-ylmethoxy)phenyl | 3,4,5-Trimethoxyphenyl |
| 72 | 2 | 0 | 3,5-Bis-(Pyridin-4-ylmethoxy)phenyl | Methyl | 3,4,5-Trimethoxyphenyl |
| 73 | 2 | 0 | Methyl | 3,5-Bis-(Pyridin-4-yl[methoxy)-4-Methyl-phenyl | 3,4,5-Trimethoxyphenyl |
| 74 | 2 | 0 | Ethyl | 3,4,5-Tris-(Pyridin-4-ylmethoxy)phenyl | 3,4,5-Trimethoxyphenyl |
| 75 | 2 | 0 | 3,4,5-Tris-(Pyridin-4-yl-methoxy)phenyl | Ethyl | 3,4,5-Trimethoxyphenyl |
| 76 | 2 | 0 | Prop-2-enyl | 3,4,5-Tris-(Pyridin-4-ylmethoxy)phenyl | 3,4,5-Trimethoxyphenyl |
| 77 | 2 | 0 | Methyl | 3,4,5-Tris-(Pyridin-4-ylmethoxy)phenyl | 3,4-Dimethoxyphenyl |
| 78 | 2 | 0 | Ethenyl | 3,4,5-Tris-(Pyridin-4-ylmethoxy)phenyl | 3,4,5-Trimethoxyphenyl |
| 79 | 2 | 0 | 3,4,5-Tris-(Pyridin-4-ylmethoxy)phenyl | Ethenyl | 3,4,5-Trimethoxyphenyl |
| 80 | 2 | 0 | Propyl | 3,4,5-Tris-(Pyridin-4-ylmethoxy)phenyl | 3,4,5-Trimethoxyphenyl |
| 81 | 2 | 0 | 3,4,5-Tris-(Pyridin-4-ylmethoxy)phenyl | Propyl | 3,4,5-Trimethoxyphenyl |
| 82 | 2 | 0 | Methyl | 3,4,5-Tris-(Thiophen-3-ylmethoxy)phenyl | 3,4,5-Trimethoxyphenyl |
| 83 | 2 | 0 | 3,4,5-Tris-(Thio-phen3-ylmethoxy)-phenyl | Methyl | 3,4,5-Trimethoxyphenyl |
| 84 | 2 | 0 | Methyl | 2-Isopropoxy-3,4-Bis-(Pyridin-4-ylmethoxy)-phenyl | 3,4,5-Trimethoxyphenyl |
| 85 | 2 | 0 | 2-Isopropoxy-3,4-Bis-(Pyridin-4-yl-methoxy)phenyl | Methyl | 3,4,5-Trimethoxyphenyl |
| 86 | 1 | 0 | Methyl | 3,4,5-Tris-(Pyridin-4-ylmethoxy)phenyl | 3,4,5-Trimethoxyphenyl |
| 87 | 1 | 0 | 3,4,5-Tris-(Pyridin-4-ylmethoxy)phenyl | Methyl | 3,4,5-Trimethoxyphenyl |
| 88 | 2 | 0 | Methyl | 3,4,5-Tris-(Pyrimidin-4-ylmethoxy)phenyl | 3,4,5-Trimethoxyphenyl |
| 89 | 2 | 0 | Benzyloxymethyl | Benzyloxyphenyl | 3,4,5-Trimethoxyphenyl |
| 90 | 2 | 0 | Methyl | 3,4,5-Tris-(Benzyl-oxy)phenyl | 3,4,5-Trimethoxyphenyl |
| 91 | 2 | 0 | 3-Phenylpropyl | 3-(Pyridin-3-yl-carbonyl)phenyl | 3,4,5-Trimethoxyphenyl |
| 92 | 2 | 0 | 3-(Pyridin-3-yl-carbonyl)phenyl | 3-Phenylpropyl | 3,4,5-Trimethoxyphenyl |
| 93 | 2 | 0 | 3-Phenylpropyl | 3-(Pyridin-4-yl-methoxy)phenyl | 3,4-Dimethoxyphenyl |
| 94 | 2 | 0 | 3-Phenylpropyl | 3-(Pyridin-4-yl-carbonyl)phenyl | 4-Benzyloxy-3,5-Di-methoxyphenyl |
| 95 | 2 | 0 | 3-Phenylpropyl | 3-(Pyridin-4-yl-carbonyl)phenyl | 4-Allyloxy-3,5-Di-methoxyphenyl |
| 96 | 2 | 0 | 3-Phenylpropyl | 3-(Pyridin-4-yl-carbonyl)phenyl | 4-Benzyloxy-4-methoxyphenyl |
| 97 | 2 | 0 | 3-Phenylpropyl | 3-(Pyridin-4-yl-carbonyl)phenyl | 4-Allyloxy-4-methoxyphenyl |

TABLE 1-continued

| Cpd. | n | m | B | D | Ar |
|---|---|---|---|---|---|
| 98 | 2 | 0 | 3-Phenylpropyl | 3-(Pyridin-4-yl-carbonyl)phenyl | 3-[3-Phenyl-(E)-prop-2-enyl]-4-methoxyphenyl |
| 99 | 2 | 0 | 3-Phenylpropyl | 4-(Pyridin-4-yl-carbonyl)phenyl | 4-Benzyloxy-3,5-Di-methoxyphenyl |
| 100 | 2 | 0 | 3-Phenylpropyl | 4-(Pyridin-4-yl-carbonyl)phenyl | 3-Benzyloxy-4-methoxyphenyl |
| 101 | 2 | 0 | 3-Phenylpropyl | 3-(Pyridin-4-yl-carbonyl)phenyl | 3,4,5-Trimethoxyphenyl |
| 102 | 2 | 0 | 3-Phenylpropyl | 3-(Pyridin-4-yl-carbonyl)phenyl | 3,4-Dimethoxyphe |
| 103 | 2 | 0 | 3-Phenylpropyl | Phenyl | 3-Benzyloxy-4-methoxyphenyl |
| 104 | 2 | 0 | 3-Phenylpropyl | Phenyl | 4-Benzyloxy-3,5-Di-methoxyphenyl |
| 105 | 1 | 0 | 3-Pyridin-3-yl)-propyl | 3-Phenylpropyl | tert-Butyl |
| 106 | 2 | 0 | 3-Pyridin-3-yl)-propyl | 3-(Pyridin-3-yl)-propyl | 3,4,5-Trimethoxyphenyl |
| 107 | 1 | 0 | Benzyloxymethyl | Benzyloxyphenyl | 3,4,5-Trimethoxyphenyl |
| 108 | 1 | 0 | 3-Pyridin-3-yl)-propyl | 3-(Pyridin-3-yl)-propyl | 3,4,5-Trimethoxyphenyl |
| 109 | 2 | 0 | 3-Pyridin-3-yl)-propyl | 3-(Pyridin-3-yl)-propyl | Isopropyl |
| 110 | 2 | 0 | 3-Pyridin-3-yl)- | 3-(Pyridin-3-yl)- | Thiophen-2-yl |
| 111 | 2 | 0 | 3-Pyridin-3-yl)-propyl | 3-(Pyridin-3-yl)-propyl | 3,4-Methylenedioxy-phenyl |
| 112 | 2 | 0 | 3-Pyridin-3-yl)-prop-2-ynyl | 3-(Pyridin-3-yl)-prop-2-ynyl | 3,4-Methylenedioxy phenyl |
| 113 | 2 | 0 | 3-Pyridin-3-yl)-prop-2-ynyl | 3-(Pyridin-3-yl)-prop-2-ynyl | 3,4,5-Trimethoxyphenyl |
| 114 | 2 | 0 | 3-Pyridin-2-yl)-propyl | 3-(Pyridin-2-yl)-propyl | 3,4,5-Trimethoxyphenyl |
| 115 | 2 | 0 | Isopropyl | 3,4,5-Tris-(Pyridin-4-ylmethoxy)phenyl | 3,4,5-Trimethoxyphenyl |
| 116 | 2 | 0 | 3,4,5-Tris-(Pyridin-4-ylmethoxy)phenyl | Isopropyl | 3,4,5-Trimethoxyphenyl |
| 117 | 2 | 0 | Prop-2-enyl | 3,4,5-Tris-(Pyridin-4-ylmethoxy)phenyl | 3,4,5-Trimethoxyphenyl |
| 118 | 2 | 0 | 3,4,5-Tris-(Pyridin-4-ylmethoxy)phenyl | Prop-2-enyl | 3,4,5-Trimethoxyphenyl |

The most preferred compounds of this invention are (S)-1-(2-oxo-2-(3,4,5-trimethoxyphenyl)acetyl)piperidine-2-carboxylic acid-4-pyridin-3-yl-1-(3-pyridin-3-yl)propyl) butyl ester, and (R)-1-(2-oxo-2-(3,4,5-trimethoxyphenyl) acetyl)piperidine-2-carboxylic acid-4-pyridin-3-yl-1-(3-pyridin-3-yl)propyl)butyl ester, pharmaceutically acceptable derivatives thereof and mixtures thereof.

As used herein, the compounds of this invention, including the compounds of formula (I), are defined to include pharmaceutically acceptable derivatives thereof. A "pharmaceutically acceptable derivative" denotes any pharmaceutically acceptable salt, ester, or salt of such ester, of a compound of this invention or any other compound which, upon administration to a patient, is capable of providing (directly or indirectly) a compound of this invention, or a metabolite or residue thereof, characterized by the ability to maintain, increase or restore sensitivity of MDR cells to therapeutic or prophylactic agents or to prevent development of multi-drug resistance. Alternatively, a "pharmaceutically acceptable derivative" denotes any pharmaceutically acceptable salt, ester, or salt of such ester, of a compound of this invention or any other compound which, upon administration to a patient, is capable of providing (directly or indirectly) a compound of this invention, or a metabolite or residue thereof, characterized by the ability to prevent, suppress or reduce an immune response.

Compounds of this invention, including those represented by formula (I), may be obtained using any conventional technique. Preferably, these compounds are chemically synthesized from readily available starting materials, such as alpha-amino acids. Modular and convergent methods for the synthesis of these compounds are also preferred. In a convergent approach, for example, large sections of the final product are brought together in the final stages of the synthesis, rather than by incremental addition of small pieces to a growing molecular chain.

Scheme 1 illustrates a representative example of a convergent process for the synthesis of compounds of formula (I'), a preferred subset of compounds of formula (I), wherein A is oxygen. The process comprises esterification of a protected alpha-amino acid of formula (X), wherein P is a protecting group, with an alcohol of formula (XI). Protected alpha-amino acids are well known in the art and many are commercially available. For example, common protecting groups and convenient methods for the protection of amino acids are described in T. W. Greene, P. G. M. Wuts, *Protective Groups in Organic Chemistry*, 2nd Ed., John Wiley and Sons, New York (1991). Alkoxycarbonyl groups are preferred for protection of the nitrogen atom in compounds of formula (X), with t-butoxycarbonyl (Boc), benzyloxycarbonyl (Cbz), allyloxycarbonyl (Alloc), and trimethylsilylethoxycarbonyl (Teoc) being more preferred.

After esterification, compounds of formula (XII) are deprotected under suitable deprotection conditions (see Greene, supra), and the free amino group of (XIII) is then acylated with a compound of formula (XIV), or an activated derivative thereof, to yield a compound of formula (I'). Methods for activation of carboxyl functionalities in carboxylic acids such as compounds of formula (XIV) are well known and many activating agents are commercially available.

Alcohols of formula (XI) wherein m is 0 (XI') can also be conveniently prepared, for example, as illustrated in Schemes 2 and 3. Reaction of an organometallic reagent of formula (XV) and an aldehyde of formula (XVI) provides alcohols of formula (XI') (Scheme 2).

Alternatively (Scheme 3), 1,6-heptadiyn-4-ol can be coupled via a metal-catalyzed reaction to aromatic halides of formula (XVII) to give an alcohol of formula (XVIII). Subsequent hydrogenation provides an alcohol of formula (XI"), a preferred subset of alcohols of formula (XI).

Scheme 1

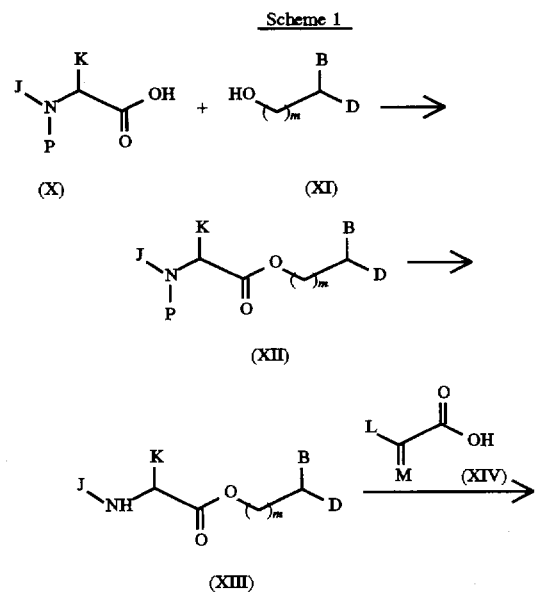

-continued
Scheme 1

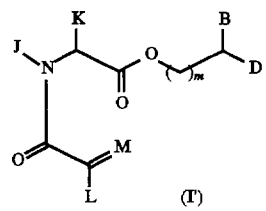

Scheme 2

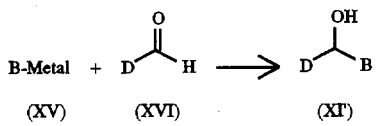

Scheme 3

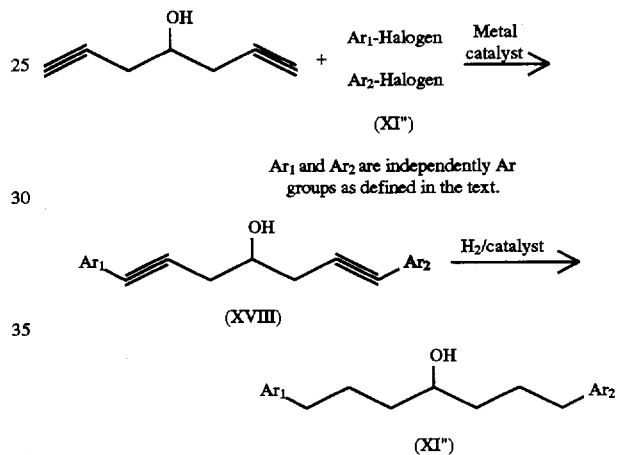

Ar₁ and Ar₂ are independently Ar groups as defined in the text.

Thus, this invention also provides a method for preparing compounds of formula (I') comprising the steps of:

(a) esterifying a protected amino acid of formula (X) with an alcohol of formula (XI) to give an intermediate of formula (XII);

(b) deprotecting the amino protecting group in the intermediate of formula (XII) to give an amino ester of formula (XIII); and (c) acylating the free amino group in the compound of formula (XIII) with a compound of formula (XIV) or an activated derivative thereof.

It should be appreciated by those of ordinary skill in the art that a large variety of compounds of formula (I) may be readily prepared, according to the processes illustrated in synthetic Schemes 1, 2 and 3. The same processes may be used for the synthesis of many different end-products, by altering the variables in the starting materials.

For example, compounds of formula (I'') (not shown) wherein A is NH or N—(C1–C4 alkyl) can be synthesized by a peptide coupling reaction between a carboxylic acid of formula (X) and an amine of formula (XI''') (not shown) to give an amide of formula (XII'). This step is analogous to the first esterification reaction of Scheme 1. The steps leading from (XII') to (I'') are also analogous to those from (XII) to (I') shown in Scheme 1.

Optically active compounds of formula (I) may also be prepared using optically active starting materials, thus obviating the need for resolution of enantiomers or separation of diastereomers at a late stage in the synthesis.

It will also be appreciated by those of ordinary skill in the art that the above synthetic schemes are not intended to comprise a comprehensive list of all means by which the compounds or the intermediates of this invention may be synthesized. Further methods or modifications of the above general schemes will be evident to those of ordinary skill in the art.

The compounds of this invention may be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

According to one embodiment, the compounds of this invention are characterized by the ability to increase, restore or maintain the sensitivity of MDR cells to cytotoxic compounds, such as, for example, those typically used in chemotherapy. Based on that ability, the compounds of this invention are advantageously used as chemosensitizing agents, to increase the effectiveness of chemotherapy in individuals who are afflicted with drug-resistant cancers, tumors, metastases or disease. In addition, the compounds of this invention are capable of maintaining sensitivity to therapeutic or prophylactic agents in non-resistant cells. Therefore, the compounds of this invention are useful in treating or preventing multi-drug resistance in a patient. More specifically, these compounds are useful intreating of preventing P-glycoprotein-meidated MDR and MRP-mediated MDR.

As used throughout this application, the term "patient" refers to mammals, including humans. And the term "cell" refers to mammalian cells, including human cells.

As used herein, the terms "sensitizing agent", "sensitizer", "chemosensitizing agent", "chemosensitizer" and "MDR modifier" denote a compound having the ability to increase or restore the sensitivity of an MDR cell, or to maintain the sensitivity of a non-resistant cell, to one or more therapeutic or prophylactic agents. The term "MDR sensitization" and "sensitization" and "resensitization" refer to the action of such a compound in maintaining, increasing, or restoring drug sensitivity.

According to one embodiment of this invention, compounds of this invention that are useful in increasing, restoring or maintaining drug sensitivity are also capable of binding to the protein FKBP-12 or other related FK-506 binding proteins such as FKBP-13, FKBP-26 and FKBP-52. In vitro tests (data not shown) of these compounds demonstrate that the agents bind to FKBP-12. Thus, this invention also comprises a class of chemosensitizing agents other than FK-506, characterized by the ability to bind to the FK binding protein-12 or related FK binding proteins, pharmaceutical compositions including such agents and a physiologically acceptable adjuvant, carrier or vehicle, and methods of using those compositions for treating or preventing multi-drug resistance in a patient.

According to another embodiment, the compounds of this invention can also be used as immunosuppressants for treatment or prophylaxis of organ rejection or treatment of chronic graft rejection and for the treatment or prevention of autoimmune diseases.

For example, the immunosuppressive compounds of this invention can be periodically administered to a patient undergoing bone marrow or organ transplantation or for another reason in which it is desirable to prevent, reduce substantially or suppress a patient's immune response, such as in various autoimmune diseases. The compounds of this invention can also be administered to mammals other than humans for prevention or treatment of various mammalian autoimmune diseases.

The novel compounds of the present invention possess a high degree of activity in suppression of antigen-stimulated growth and clonal expansion of T-cells, especially those T-cells characterized as "helper" T-cells. This activity is useful in the primary prevention of organ transplant rejection, in the rescue of transplanted organs during a rejection episode, and in the treatment of any of several autoimmune diseases known to be associated with inappropriate autoimmune responses. These autoimmune diseases include: uveitis, Behcet's disease, Grave's ophthalmopathy, psoriasis, acute dermatomyositis, atopic skin disease, scleroderma, eczema, pure red cell aplasia, aplastic anemia, primary cirrhosis, autoimmune hepatitis, ulcerative colitis, Crohn's disease, amyotrophic lateral sclerosis, myasthenia gravis, multiple sclerosis, nephrotic syndrome, membrano-proliferative glomerulonephritis, rheumatoid arthritis and insulin-dependent diabetes mellitus. In all of the above-listed autoimmune diseases, treatment is effective to reduce the symptoms and slow progression of the disease. In the case of insulin-dependent diabetes mellitus, treatment as described below is most effective when instituted before the complete cessation of natural insulin production and transition to complete dependence on external insulin.

Because compounds according to this invention exhibit immunosuppressive activity, as well as activity against multi-drug resistance, it will be appreciated by those of ordinary skill in the art that compounds preferred for use in preventing or modulating multi-drug resistance are those which are not significantly immunosuppressive at clinically useful or prophylactically or therapeutically active levels—i.e., the effect, if any, of immunosuppression of a given patient does not outweigh the value of sensitization activity of the compound to that patient. Those of ordinary skill in the art will also appreciate that such immunosuppressive capabilities can be ascertained by the in vitro assays set forth below or as described in U.S. patent application Ser. No. 07/547,814 (now U.S. Pat. No. 5,192,773), the disclosure of which is incorporated herewith.

The compounds of the present invention may be used in the form of pharmaceutically acceptable salts derived from inorganic or organic acids and bases. Included among such acid salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth. Also, the basic nitrogen-containing groups can be quaternized with such agents as lower alkyl halides, such as methyl, ethyl, propyl, and butyl chloride, bromides and iodides;

dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The compounds of the present invention may be administered orally, parenterally, by inhalation spray, topically, rectally, nasally, buccally, vaginally or via an implanted reservoir in dosage formulations containing conventional non-toxic pharmaceutically-acceptable carriers, adjuvants and vehicles. The term "parenteral" as used herein includes subcutaneous, intravenous, intramuscular, intra-articular, intra-synovial, intrasternal, intrathecal, intrahepatic, intralesional and intracranial injection or infusion techniques.

The pharmaceutical compositions of this invention comprise any of the compounds of the present invention, or pharmaceutically acceptable salts thereof, with any pharmaceutically acceptable carrier, adjuvant or vehicle. Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to this invention, the pharmaceutical compositions may be in the form of a sterile injectable preparation, for example a sterile injectable aqueous or oleaginous suspension. This suspension may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of active ingredient that may be combined with the carrier materials to produce a single dosage form will vary depending upon the host treated, the particular mode of administration and the intended effect of therapy, i.e., immunosuppression or treatment or prevention of multi-drug resistance. It should be understood, however, that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredient may also depend upon the therapeutic or prophylactic agent, if any, with which the ingredient is co-administered.

According to those embodiments of this invention directed to the treatment or prevention of multi-drug resistance, the term "pharmaceutically effective amount"

refers to an amount effective to prevent multi-drug resistance or maintain, increase or restore drug sensitivity in MDR cells. According to those embodiments of this invention directed to immunosuppression, rather than treatment or prevention of multi-drug resistance, the term "pharmaceutically effective amount" refers to an amount effective to prevent, suppress or substantially reduce the immune response of a mammal.

Dosage levels of between about 0.01 and about 100 mg/kg body weight per day, preferably between about 0.5 and about 50 mg/kg body weight per day of the active ingredient compound are useful. A typical preparation will contain between about 5% and about 95% active compound (w/w). Preferably, such preparations contain between about 20% and about 80% active compound. Generally speaking, within the dosage ranges specified herein, the preferred compounds of this invention induce MDR-sensitization at doses which are not substantially immunosuppressive to the patient.

When the compounds of this invention are administered in combination therapies with other agents, they may be administered sequentially or concurrently to the patient. Alternatively, pharmaceutical or prophylactic compositions according to this invention may comprise a combination of a compound of this invention and another therapeutic or prophylactic agent.

For example, the compounds may be administered either alone or in combination with one or more therapeutic agents, such as chemotherapeutic agents. (e.g., actinomycin D, doxorubicin, vincristine, vinblastine, etoposide, amsacrine, mitoxantrone, tenipaside, taxol and colchicine) and/or a chemosensitizing agent (e.g., cyclosporin A and analogs, phenothiazines and thioxanthenes), in order to increase the susceptibility of the MDR cells within the patient to the agent or agents.

Alternatively, when the target use of the compounds of this invention is immunosuppression, rather than treatment or prevention of multi-drug resistance, the compounds may be administered in combination with asteroid, such as methyl prednisalone acetate, for additional immunosuppressive effect. The steroid is administered orally, intravenously, rectally, topically or by inhalation. Dosages (based upon methyl prednisalone acetate) of 0.1–5 mg/kg/day may be employed. An initial loading dose of 100–500 mg may be employed. Steroid doses may be decreased with time from the higher toward the lower doses as the clinical situation indicates.

The compounds can be administered with other immunosuppressant drugs, such as rapamycin, azathioprine, 15-deoxyspergualin, mycophenolic acid, brequinar, cyclosporin A, FK-506 or combinations of these, to increase the immunosuppressive effect. Administration of cyclosporin and FK-506 together should be avoided due to contraindications reported resulting from coadministration of these immunosuppressants. The dosage level of other immunosuppressant drugs will depend upon the factors previously stated and the immunosuppressive effectiveness of the drug combination.

OKT3, which is a murine monoclonal antibody to CD3 surface antigen of human T lymphocytes, can also be coadministered intravenously with compounds of the present invention for rescue and reversal of acute allograft rejections, particularly in renal transplantations.

In order that this invention may be more fully understood, the following examples are set forth. These examples are for the purpose of illustration only and are not to be construed as limiting the scope of the invention in any way.

EXAMPLES

General Methods

Proton nuclear magnetic resonance ($^1$H NMR) spectra were recorded at 500 MHz on a Bruker AMX 500. Chemical shifts are reported in parts per million ($\delta$) relative to Me$_4$Si ($\delta$ 0.0). Analytical high performance liquid chromatography was performed on either a Waters 600E or a Hewlett Packard 1050 liquid chromatograph.

Example 1

Synthesis of (S)-1,7-Diphenyl-4-heptanyl N-(3,4,5-trimethoxyphenylglyoxyl)pipecolate (3)

4-Phenyl-1-butanal (119).

To a solution of 3.2 mL (20.8 mmol) of 4-phenyl-1-butanol (Aldrich Chemical Co.) in 20 mL of CH$_2$Cl$_2$ at 0° C. was added 3.2 g of powdered 3 Å molecular sieves and then 5.37 g (24.9 mmol) of pyridinium chlorochromate (PCC). The resulting suspension was stirred at 0° C. for 1 h at which time an additional 2.16 g (10.0 mmol) of PCC was added and the reaction mixture was warmed to room temperature. After stirring at ambient temperature for 0.5 h, the reaction mixture was diluted with ether and filtered through celite to give 2.5 g of the crude product. Flash chromatography (elution with 5% ethyl acetate in hexane) yielded 700 mg of the aldehyde 119. $^1$H NMR was consistent with the structure.

3-Phenyl-1-propylmagnesium bromide (120).

To a suspension of 736 mg (30.3 mmol) of magnesium turnings in 50 mL of THF at room temperature was added 50 µL of 1,2-dibromoethane followed by the dropwise addition of 5.5 g (25.1 mmol) of 1-bromo-3-phenylpropane (Aldrich Chemical Co.). After stirring at room temperature for 0.5 h, the supernatant was transferred via cannula to a 100 mL storage vessel and subsequently used as a 0.5M THF solution of the Grignard reagent 120.

1,7-Diphenyl-4-heptanol (121).

To a solution of 700 mg (4.7 mmol) of 4-phenyl-1-butanal (119) in 5.0 mL of THF at 0° C. was added 10.0 mL (5.0 mmol) of 3-phenyl-1-propylmagnesium bromide (120) and the resulting mixture was stirred at 0° C. for 0.5 h. The mixture was then quenched by the dropwise addition of saturated NH$_4$Cl and diluted with ether. The phases were separated and the organic layer was washed with water and brine and then dried over MgSO$_4$. Concentration gave 1.12 g of the alcohol 121 as an oil. $^1$H NMR spectrum was consistent with the structure.

(S)-Boc-1-Pipecolyl-1,7-diphenyl-4-heptanyl ester (122).

To a solution of 164 mg (0.72 mmol) of Boc-L-Pipecolic acid in 5.0 mL of CH$_2$Cl$_2$ at room temperature was added 174 mg (0.65 mmol) of alcohol 121, 140 mg (0.72 mmol) of 1-(3-dimethylaminopropyl)-3-ethylcarbodiimide hydrochloride (EDC) and a catalytic amount of N,N-dimethylaminopyridine (DMAP). The reaction mixture was stirred at ambient temperature for 0.5 h and then applied directly to a silica gel column. Elution with 10% ethyl acetate in hexane afforded 76.2 mg of the ester 122 as an oil. $^1$H NMR spectrum was consistent with the structure.

(S)-1,7-Diphenyl-4-heptanylpipecolate (123).

To a solution of 47 mg (0.10 mmol) of the ester 122 in 1.0 mL of CH$_2$Cl$_2$ at ambient temperature was added 1.0 mL of trifluoroacetic acid. After stirring at room temperature for 0.5 h, the resulting solution was neutralized by the dropwise addition of saturated K$_2$CO$_3$. The layers were separated and the organic phase was washed with water, dried over MgSO₄ and concentrated to yield 23 mg of the amine 123 as an oil. ¹H NMR consistent with structure.

3,4,5-Trimethoxybenzoylformic acid (124).

To a solution of 9.2 g (43.4 mmol) of 3,4,5-trimethoxyacetophenone (Aldrich Chemical Co.) in 35 mL of pyridine was added 6.3 g (56.7 mmol) of selenium dioxide and the resulting solution was heated at reflux overnight. The reaction mixture was cooled to room temperature, filtered through celite and concentrated to yield a dark brown oil which was dissolved into ethyl acetate and washed with 1.0N HCl and then with saturated NaHCO₃. The basic aqueous layer was diluted with ether and acidified with concentrated HCl. The layers were separated and the organic phase was washed with brine and then dried over Na₂SO₄ to give 8.4 g of the acid 124 as a dark yellow solid. Recrystallization of this material from ethyl acetate-hexane then gave 6.8 g of the acid 124 as a pale yellow solid. ¹H NMR consistent with structure.

(S)-1,7-Diphenyl-4-heptanyl N-(3,4,5-trimethoxyphenylglyoxyl)pipecolate (3).

To a solution of 23 mg (0.06 mmol) of the amine 123 in 1.0 mL of CH₂Cl₂ at room temperature was added 21.8 mg (0.09 mmol) of the acid 124 and then 17.9 mg (0.09 mmol) of EDC and the resulting solution was stirred at room temperature for 0.5 h and applied directly to a silica gel column. Elution with 15% ethyl acetate in hexane gave 8.4 mg of the amide 3 as a mixture of rotamers. ¹H NMR (500 MHz CDCl₃ δ 7.35–7.06(m), 5.32(br s), 5.00(br s), 4.88(br s), 4.58(d), 4.31(br s), 3.95(s), 3.90(s), 3.89(s), 3.85(s), 3.44(d), 3.21(t), 3.04(t), 2.54(br s), 2.51(br s), 2.42(br s), 2.30(d), 2.15(d), 1.83–1.21(m).

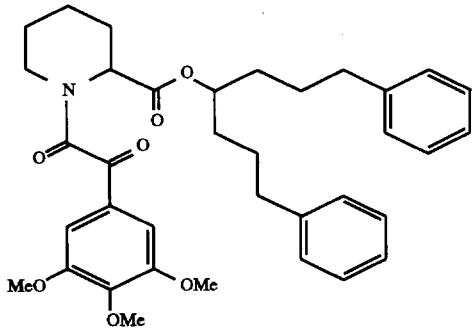

3

Example 2

Synthesis of (R and S)-1-(3-Phenoxy)phenyl-4-phenyl-1-butyl (S)-N-(3,4,5-trimethoxyphenylglyoxyl)pipecolate (4).

3-Phenoxybenzaldehyde (125).

To a solution of 1.8mL (10.3 mmol) of 3-phenoxybenzyl alcohol (Aldrich Chemical Co.) in 20 mL of CH₂Cl₂ at room temperature was added 1.5 g of powdered 4 Å molecular sieves and 2.5 g of activated MnO₂. The resulting suspension was stirred at room temperature for 0.5 h, at which time an additional 2.5 g of MnO₂ was added. After stirring at room temperature for 0.5 h the reaction mixture was filtered through celite to give 1.84 g of the aldehyde 125 as an oil. ¹H NMR consistent with structure.

(R and S)-1-(3-Phenoxy)phenyl-4-phenyl-1-butanol (126).

The alcohol 126 was prepared from 190 mg (0.96 mmol) of aldehyde 125 and 2.0 mL (1.0 mmol) of the Grignard reagent 120 in 2.0 mL of THF as described above for the synthesis of the alcohol 121 in Example 1. Flash chromatography (elution with 10% ethyl acetate in hexane) afforded 108 mg of the racemic alcohol 126. ¹H NMR consistent with structure.

(S)-N-3,4,5-(Trimethoxyphenyl)glyoxyl pipecolic acid (127).

To a slurry of 953.3 mg (3.4 mmol) of the tartrate salt of (S)-pipecolic acid (Egbertson, M. and Danishefsky, S. J., J. Org. Chem. 1989, 54, 11) in 7.0 mL of CH₂Cl₂ at 0° C. was added 3.9 mL (22.39 mmol) of diisopropylethylamine and 2.4 mL (18.9 mmol) of chlorotrimethylsilane and the resulting solution was allowed to stir at 0° C. for 0.5 h. In a separate reaction flask 450 μL (5.2 mmol) of oxalyl chloride and three drops of DMF were added to a solution of 820 mg (3.4 mmol) of acid 124 in 7.0 mL of CH₂Cl₂. After the evolution of gas ceased, the entire contents of the second flask were added to the first reaction vessel and the resulting mixture was allowed to stir at room temperature for 1 h. The reaction mixture was concentrated, dissolved into ether and washed with 0.5N HCl and then saturated NaHCO₃. The basic aqueous phase was acidified with concentrated HCl and extracted with ether. The ethereal extracts were washed with water, brine, dried over MgSO₄ and concentrated to give 490 mg of the acid 127. ¹H NMR consistent with structure.

(R and S)-1-(3-Phenoxy)phenyl-4-phenyl-1-butyl (S)-N-(3,4,5-trimethoxphenylglyoxyl)pipecolate (4).

To a solution of 29.4 mg (0.08 mmol) of acid 127 in 2.0 mL of CH₂Cl₂ at room temperature was added 11 μL (0.13 mmol) of oxalyl chloride and three drops of DMF and the reaction mixture was allowed to stir at room temperature for 0.5 h and was then concentrated and suspended in 1.0 mL of benzene. To this suspension was added 32.0 mg (0.1 mmol) of alcohol 126 and 13.4 mg (0.1 mmol) of silver cyanide. The resulting mixture was heated at reflux overnight, cooled to room temperature and concentrated. Flash chromatography (elution with 10% ethyl acetate in hexane) gave 8.8 mg of the ester 4 as a mixture of diastereomers. ¹H NMR (500 MHz CDCl₃) δ7.34–7.19 (m), 7.18–7.03 (m) 7.02–6.84 (m), 6.83–6.72 (m), 5.73 (q), 5.69–5.55 (m), 5.38 (t), 4.55 (br d), 4.35 (dd), 3.94 (s), 3.92 (s), 3.89 (s), 3.83 (s), 3.73 (s), 3.63 (s), 3.48–3.35 (m), 3.20 (t), 3.10 (t), 2.60 (q), 2.40 (dd), 1.95–1.91 (m), 1.90–1.45 (m).

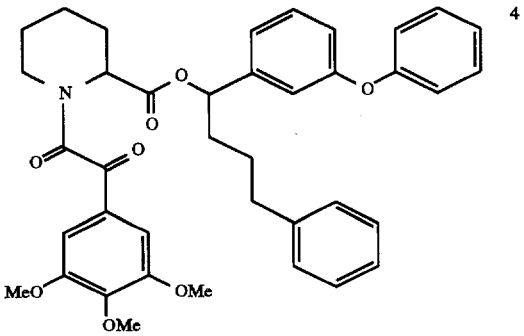

4

Example 3

Synthesis of R and S)-6-Phenyl-1-(3-pyridyl)-3-hexyl (S)-N-(3,4,5-trimethoxphenylglyoxyl) pipecolate (7)

3-(3-Pyridyl)-1-propylaldehyde (128).

To a solution of 2.3 g (5.46 mmol) of the Dess-Martin periodinane (Dess, D. B.; Martin, J. C. J. Org. Chem. 1983, 48, 4155) in 10 mL of $CH_2Cl_2$ at 0° C. was added 470 μL (3.65 mmol) of 3-(3-pyridyl)-1-propanol and the resulting mixture was allowed to warm from 0° C. to ambient temperature over a 1.5 h period. To this solution was added 6.0 g (38.22 mmol) of $Na_2S_2O_3$ in saturated $NaHCO_3$ and the reaction mixture was allowed to stir at room temperature for 15 min. The reaction was extracted with $CH_2Cl_2$, dried over $MgSO_4$ and concentrated. Flash chromatography (elution with 3:1 hexane;acetone) yielded the product aldehyde 128 as an oil. $^1H$ NMR consistent with structure.

(R and S)-6-Phenyl-1-(3- pyridyl)-3-hexanol (129).

The alcohol 129 was prepared from 125 mg (0.92 mmol) of aldehyde 128 and 2.0 mL (1.0 mmol) of 120 in 2.0 mL of THF as described above for the synthesis of alcohol 121 in Example 1 to give 221 mg of the crude alcohol 129. $^1H$ NMR consistent with structure.

(S)-Boc-Pipecolyl-(R and S)-6-Phenyl-1-(3-pyridyl)-3-hexyl ester (130).

The ester 130 was prepared from 125 mg (0.49 mmol) of alcohol 129, 93 mg (0.41 mmol) of Boc-pipecolic acid, 94 mg (0.49 mmol) of EDC and a catalytic amount of DMAP in 1.0 mL of $CH_2Cl_2$ and 1.0 mL of DMF as described above for the synthesis of 122 in Example 1. Flash chromatography (elution with 2:1 hexane: ethyl acetate) gave 105 mg of the diastereomeric ester130 as an oil. $^1H$ NMR consistent with structure.

(R and S)-6-Phenyl-1-(3- pyridyl)-3-hexyl (S)-pipecolate (131).

The amine 131 was synthesized by treating 95 mg (0.20 mmol) of the ester 130 with 1.0 mL of trifluoroacetic acid in 3.0 mL of $CH_2Cl_2$ as described above for the preparation of amine 223 in Example 1, giving 58 mg of the diastereomeric amine 131 as an oil. $^1H$ NMR consistent with structure.

(R and S)-6-Phenyl-1-(3-pyridyl)-3-hexyl (S)-N-(3,4,5-trimethoxyphenylglyoxyl)pipecolate (7).

The ester 7 was prepared from 54 mg (0.15 mmol) of the amines 131, 50 mg (0.22 mmol) of the acid 124 and 42 mg (0.22 mmol) of EDC in 3.0 mL of $CH_2Cl_2$ as described above in the synthesis of ester 3 in Example 1. Flash chromatography (elution with 1:1 ethyl acetate:hexane) gave 73 mg of the diastereomeric ester 7 as a mixture of rotamers. $^1H$ NMR (500 MHz $CDCl_3$) δ 8.48–8.42 (m), 7.50–7.41 (m), 7.32 (d), 7.27–7.03 (m), 5.38 (d), 5.31 (d), 5.06–5.01 (m), 4.97–4.93 (m), 4.60 (br d), 3.92 (s), 3.88 (s), 3.86 (s), 3.84 (s), 3.82 (s), 3.79 (s), 3.46 (br d), 3.27 (br t), 2.73–2.68 (m), 2.38–2.29 (m), 1.98–1.76 (m), 1.75–1.60 (m), 1.56–1.51 (m), 1.38–1.20 (m).

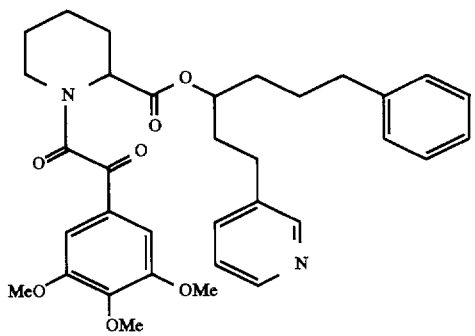

7

Example 4

Synthesis of (R and S)-E-1-[trans-(4-Hydroxycyclohexyl)]-2-methyl-6-phenyl-3-hex-1-enyl (S)-N-(3,4,5-trimethoxyphenylglyoxyl) pipecolate (8)

cis-and trans-4-(tert-Butyldimethylsilyloxy)cykclohexan-1-ol (132) and (133).

To a solution of 3.43 g (21.7 mmol) of cis- and trans-methyl 4-hydroxycyclohexane carboxylate (Noyce, D. S.; Denney, D. B. J. Am. Chem. Soc. Vol. 74, 5912 (1952)) in 45 mL of methylene chloride at 0° C. was added 3.0 mL (26.0 mmol) of 2,6-lutidine followed by 5.5 mL (23.0 mmol) of tert-butyldimethylsilyl trifluoromethanesulfonate. The ice bath was removed and the reaction mixture was allowed to stir at 25° C. for 2 h, at which time the solution was poured into saturated sodium bicarbonate. The layers were partitioned and the organic layer was washed with saturated copper sulfate and water and then dried over $MgSO_4$ to give 5.9 g of the crude methyl esters. A solution of 5.72 g (21.0 mmol) of this mixture in 45 mL of anhydrous THF was treated with 400 mg (10.5 mmol) of lithium aluminum hydride. The reaction mixture was stirred at 25° C. for 0.5 h and was then quenched by the slow addition of a saturated solution of Rochelle's salt. The mixture was diluted with ether, the layers were partitioned and the aqueous layer was washed twice with ethyl acetate. The combined organic extracts were dried over $MgSO_4$ and concentrated to give 4.9 g of the diastereomeric alcohols. Flash chromatography (elution with 1:5 ethyl acetate-hexane) gave 650 mg of 132, 1.10 g of 133 and 2.40 g of a mixture of the two. Data for 132: $^1H$ NMR (300 MHz, $CDCl_3$) δ 3.99–3.92(m), 3.46(d), 1.72–1.58 (m), 1.57–1.36(m), 0.86(s), 0.08(s). Data for 133: $^1H$ NMR (300 MHz, $CDCl_3$) δ 3.47(dddd), 3.38(d), 1.86–1.67(m), 1.47–1.16(m), 1.05–0.77(m), 0.72(s), 0.02(s).

(E)-Ethyl 3-[trans-(4-tert-Butyldimethylsilyloxycyclohexyl)]-2-methylprop-2-enoate (134).

To a –78° C. solution of oxalyl chloride (785 μL, 9.0 mmol) in 10 mL of methylene chloride was added dimethylsulfoxide (1.3 mL, 18.0 mmol). The resulting solution was stirred for 5 min and then 1.1 g (4.5 mmol) of the alcohol 133 was added in 10 mL of methylene chloride. The reaction mixture was stirred at –78° C. for 45 min at which time 3.8 mL (27.0 mmol) of triethylamine was added and the solution was allowed to warm to ambient temperature. The reaction was quenched with 1.0N HCl and the aqueous layer was extracted with three portions of methylene chloride. The combined organic extracts were dried over $MgSO_4$ and evaporated to dryness to give 1.0 g of the intermediate aldehyde. A solution of this aldehyde (450 mg, 1.86 mmol) was treated directly with 710 mg (1.95 mmol) of (carbethoxyethylidene)triphenyl-phosphorane in 5.0 mL of methylene chloride. The resulting reaction mixture was stirred at ambient temperature overnight and was then poured into water. The layers were partitioned and the aqueous layer was extracted twice with methylene chloride. The combined organic layers were dried over $MgSO_4$ and concentrated to yield the enoate 134 containing a minor amount of the Z isomer. $^1H$ NMR consistent with structure.

(E)-3-[trans-(4-tert-Butyldimethysilyloxycyclohexyl)]-2-methylprop-2-en-1-ol (135).

To a solution of 860 mg (2.6 mmol) of enoate 134 in 5.0 mL of anhydrous tetrahydrofuran at 25° C. was added 50 mg (1.3 mmol) of lithium aluminum hydride and the resulting mixture was allowed to stir for 30 min. The reaction was quenched by the slow addition of saturated Rochelle's salt and diluted with ethyl acetate. The layers were separated and the aqueous layer was extracted with two portions of ethyl acetate. The combined organic extracts were washed with both water and brine and then dried over MgSO$_4$. Evaporation and flash chromatography (elution with 15% ethyl acetate in hexane) gave 370 mg of the allylic alcohol 135. $^1$H NMR consistent with structure.

(E)-3-[trans-(4-tert-Butyldimethylsilyloxycyclohexyl)]-2-methylprop-2-en-1-al (136).

To a −78° C. solution of oxalyl chloride (105 μL, 1.2 mmol) in 1.0 mL of methylene chloride was added dimethylsulfoxide (170 μL, 2.4 mmol). The resulting solution was stirred for 5 min and then 170 mg (0.6 mmol) of the alcohol 135 was added in 1.0 mL of methylene chloride. The reaction mixture was stirred at −78° C. for 45 min at which time 500 μL (3.6 mmol) of triethylamine was added and the solution was allowed to warm to ambient temperature. The reaction was quenched with 1.0N HCl and the aqueous layer was extracted with three portions of methylene chloride. The combined organic extracts were dried over MgSO$_4$ and evaporated to dryness to give the crude aldehyde 136 which was used directly in the next reaction. $^1$H NMR consistent with structure.

(R and S)-(E)-1-[trans-(4-tert-Butyldimethylsilyloxycyclohexyl)]-2-methyl-6-phenylhex-1-en-3-ol (137).

The alcohol 137 was prepared from the crude aldehyde 136. and 1.5 mL (0.75 mmol) of 120 in 2.0 mL of THF as described above for the synthesis of alcohol 121 in Example 1 to give 220 mg of the crude diastereomeric alcohol 137. Flash chromatography (elution with 20% ethyl acetate in hexane) afforded 146 mg of the alcohol 137 as an oil. $^1$H NMR consistent with structure.

(R and S)-(E)-1-[trans-(4-tert-Butyldimethylsilyloxycyclohexyl)]-2-methyl-6-phenyl-3-hex-1-enyl (S)-N-(3,4,5-trimethoxyphenylglyoxyl)pipecolate (138).

To a solution of 75.7 mg (0.22 mmol) of acid 127 in 2.5 mL of CH$_2$Cl$_2$ at room temperature was added 30 μL (0.34 mmol) of oxalyl chloride and three drops of DMF and the reaction mixture was allowed to stir at room temperature for 0.5 h and was then concentrated and suspended in 1.0 mL of benzene. To this suspension was added 43.4 mg (0.11 mmol) of alcohol 137 and 28.8 mg (0.22 mmol) of silver cyanide. The resulting mixture was heated at reflux overnight, cooled to room temperature and concentrated. Flash chromatography (elution with 4% acetone in hexane) gave 17.5 mg of the ester 138 as a mixture of diastereomers. $^1$H NMR consistent with structure.

(R and S)-(E)-1-[trans-(4-Hydroxycyclohexyl)]-2-methyl-6-phenyl-3-hex-1-enyl (S)-N-(3,4,5-trimethoxyphenylglyoxyl)pipecolate (8).

To a solution of 17.5 mg (0.02 mmol) of the ester 138 in 1.0 mL of CH$_3$CN at room temperature was added 10 drops of a 95:5 solution of CH$_3$CN:5% HF and the resulting mixture was stirred at room temperature for 0.5 h. The reaction mixture was neutralized with saturated K$_2$CO$_3$ and extracted into ether. The ether layers were washed with water, dried over MgSO$_4$ and concentrated to yield 7.2 mg of crude material. Flash chromatography (elution with 15% acetone in hexane) gave 4.9 mg of the diastereomeric alcohol 8 as a mixture of rotamers. $^1$H NMR (500 MHZ, CDCl$_3$) δ 7.38–7.02(m), 5.35–5.01(m), 4.62–4.53(m), 4.28 (t), 3.95(s), 3.89(s), 3.87(s), 3.86(s), 3.85(s), 3.81(s), 3.55 (m), 3.45(m), 3.20(m), 3.10–2.90(m), 2.60–2.45(m), 2.32(t), 2.10(t), 1.95(d), 1.85–1.40(m), 1.39–1.02(m).

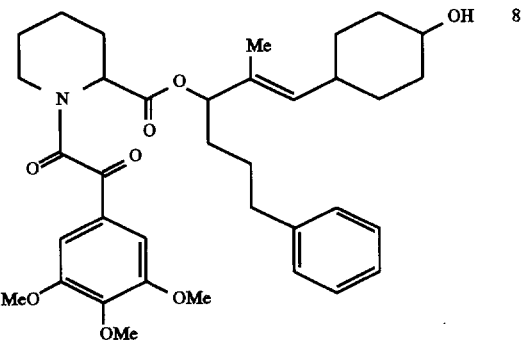

Example 5

Synthesis of (R and S)-5-(3-indolyl)-1-phenyl-2-pentyl (S)-N-(3,4,5-tri-methoxyphenylglyoxyl) pipecolate (11)

N-Methyl-N-Methoxy-4-(3-indolyl)butyramide (139).

To a slurry of 1.75 g (8.61 mmol) of 3-indolebutyric acid (Aldrich Chemical Co.) in acetonitrile at room temperature was added 7.0 mL (40.2 mmol) of N,N-diisopropylethylamine, 1.0 g (10.3 mmol) of N,N-dimethylhydroxylamine hydrochloride and 4.19 g (9.5 mmol) of benzotriazol-1-yloxy-tris(dimethylamino) phosphonium hexafluorophosphate (BOP reagent) and the resulting mixture was allowed to stir at room temperature overnight and was then concentrated to dryness. The residue was dissolved into ethyl acetate and washed with water, 0.5N HCl, saturated NaHCO$_3$ and brine and then dried over MgSO$_4$ and concentrated. Flash chromatography (elution with a gradient of 2–10% ether in methylene chloride) provided 2.0 g of the amide 139. $^1$H NMR consistent with structure.

Benzyl-3-(3-indolyl)propyl ketone (140).

To a solution of 147 mg (0.60 mmol) of amide 139 in 4.0 mL of THF at −78° C. was added 1.31 mL (1.31 mmol) of benzylmagnesium chloride (1.0M in Et$_2$O) and the reaction mixture was allowed to warm to room temperature and stir for 3 h. The reaction was quenched with 5% KHSO$_4$ and extracted into ether. The combined ethereal layers were washed with brine and dried over MgSO$_4$. Flash chromatography (elution with 25% ether in hexane) gave 108 mg of the ketone 140. $^1$H NMR consistent with structure.

(R and S)-5-(3-indolyl)-1-phenyl-2-pentanol (141).

To a slurry of 105 mg (0.38 mmol) of ketone 140 in 3.0 mL of MeOH at 0° C. was added 30 mg (0.79 mmol) of solid NaBH$_4$ and the resulting suspension was allowed to stir for 3 h. The reaction mixture was quenched with 5% KHSO$_4$ and extracted into ethyl acetate. The combined organic extracts were washed with brine and dried over MgSO$_4$. Flash chromatography (elution with 4% ether in methylene chloride) gave 81 mg of the alcohol 141 as a white solid. $^1$H NMR consistent with structure.

(S)-Boc-Pipecolyl-(R and S)-5-(3-indolyl)-1-phenyl-2-pentyl ester (142).

The ester 142 was prepared from 80 mg (0.29 mmol) of alcohol 141, 82 mg (0.36 mmol) of (S)-Boc-pipecolic acid, 66 mg (0.34 mmol) of EDC and a catalytic amount of 4-pyrrolidinopyridine in 2.0 mL of CH$_2$Cl$_2$ (mixture was allowed to stir overnight at room temperature) as described above for the synthesis of ester 122 in Example 1. Flash chromatography (elution with 4:10:26 ether: methylene chloride: hexane) gave 108 mg of the diastereomeric ester 142. as a white foam. $^1$H NMR consistent with structure.

(R and S)-5-(3-indolyl)-1-phenyl-2-pentyl (S)-pipecolate hydrochloride salt (143).

Anhydrous HCl was bubbled into a solution of 103 mg (0.21 mmol) of the ester 142 in 10 mL of EtOAc at –20° C. for 10 min and then the reaction mixture was purged with $N_2$. Concentration gave 108 mg of the crude amine 143 as the hydrochloride salt. $^1$H NMR consistent with structure.

(R and S)-5-(3-indolyl)-1-phenyl-2-pentyl (S)-N-(3,4,5-trimethoxyphenylglyoxyl)pipecolate (11)

To a slurry of 108 mg of the crude amino hydrochloride 143 in $CH_3CN$ at room temperature was added 91 µL (0.52 mmol) of N,N-diisopropylethylamine, 76 mg (0.31 mmol) of acid 124, and 111 mg (0.25 mmol) of the BOP reagent and the resulting mixture was stirred at room temperature for two days and then was concentrated to dryness. The residue was reconstituted into 75 mL of ethyl acetate and then sequentially washed with water, 5% $KHSO_4$, saturated $NaHCO_3$ and brine and then dried over $MgSO_4$ and concentrated. Flash chromatography (elution with 4% ether in methylene chloride) gave 56.7 mg of the diastereomeric amide 11 as a rotameric mixture. $^1$H NMR (500 MHz, $CDCl_3$) δ 7.98(d), 7.56(t), 7.38–6.73(m), 5.38–5.14(m), 3.90(m), 3.38(brt), 3.10(brt), 2.97–2.60(m), 2.31(d), 2.10 (d), 1.98–1.17(m), 0.8(m). $R_f$ 0.51 (10% ether in methylene chloride).

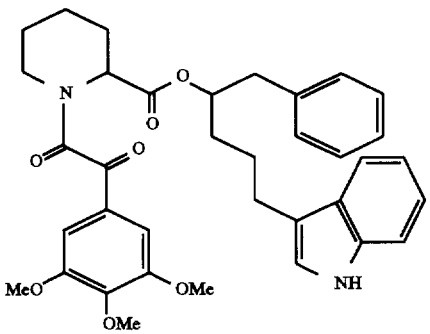

Example 6

Synthesis of (R and S)-2-Benzyl-4-phenyl-1-butyl (S)-N-(3,4,5-trimethoxyphenylglyoxyl)pipecolate (16)

(R and S)-2-Benzyl-4-phenyl-1-butyric acid (144).

To a solution of 1.06 g (6.43 mmol) of 4-phenylbutyric acid in 20 mL of THF at 0° C. was added 193 mg (6.43 mmol) of solid NaH (80% in mineral oil). After stirring at 0° C. for 0.5 h, 3.2 mL (6.43 mmol) of lithium diisopropyl amide-THF complex (2.0M) was added and the resulting red solution was stirred at 0° C. for 45 min. To this mixture was added 765 µL (6.43 mmol) of benzyl bromide and the solution was then allowed to stir overnight at room temperature. The reaction mixture was quenched by the slow addition of saturated $NaHCO_3$ and then washed with ether. The basic extracts were acidified with solid $KHSO_4$ and partitioned with ethyl acetate. The combined organic extracts were washed with brine, dried over $MgSO_4$ and concentrated to give 484 mg of the acid 144. $^1$H NMR consistent with structure.

(R and S)-2-Benzyl-4-phenyl-1-butanol (145).

To a solution of 469 mg (1.84 mmol) of acid 144 in 3.0 mL of THF at –78° C. was added 2.03 mL (2.03 mmol) of lithium aluminum hydride (1.0M in THF) and the resulting solution was allowed to warm to room temperature and stirred overnight. The reaction mixture was quenched by the slow addition of Rochelle's salt and partitioned with ether. The combined ether extracts were washed with water and brine and dried over $MgSO_4$ and concentrated. Flash chromatography (elution with 2% ether in methylene chloride) afforded 264 mg of the alcohol 1.45. $^1$H NMR consistent with structure.

(S)-Boc-Pipecolyl-(R and S)-2-Benzyl-4-phenyl-1-butyl ester (146).

The ester 146 was prepared from 264 mg (1.10 mmol) of alcohol 145, 302 mg (1.32 mmol) of (S)-Boc-L-pipecolic acid, 253 mg (1.32 mmol) of EDC and a catalytic amount of 4-pyrrolidinopyridine in 2.0 mL of $CH_2Cl_2$ (mixture was allowed to stir at room temperature for 3 days) as described above for the synthesis of ester 122 in Example 1. Flash chromatography (elution with 1:5:14 ether:methylene chloride:hexane) gave 375 mg of the diastereomeric ester 146. $^1$H NMR consistent with structure.

(R and S)-2-Benzyl-4-phenyl-1-butyl (S)-pipecolate hydrochloride salt (147).

Anhydrous HCl was bubbled into a solution of 375 mg (0.83 mmol) of the ester 146 in 10 mL of EtOAc at –20° C. for 10 min and then the reaction mixture was purged with $N_2$. Concentration gave 352 mg of the crude amine 147 as the hydrochloride salt. $^1$H NMR consistent with structure.

(R and S)-2-Benzyl-4-phenyl-1-butyl (S)-N-(3,4,5-trimethoxyphenylglyoxyl)pipecolate (16).

To a slurry of 54 mg (0.14 mmol) of the crude amine hydrochloride 147 in 2.0 mL of $CH_3CN$ at room temperature was added 60 µL (0.35 mmol) of N,N-diisopropylethylamine, 50 mg (0.21 mmol) of acid 124, and 73 mg (0.16 mmol) of the BOP reagent and the resulting mixture was stirred for 3 days at room temperature and was then concentrated to dryness. The residue was reconstituted into 75 mL of ethyl acetate and then sequentially washed with water, 5% $KHSO_4$, saturated $NaHCO_4$ and brine and then dried over $MgSO_4$ and concentrated. Flash chromatography (elution with 2% ether in methylene chloride) gave 52.7 mg of the diastereomeric amide 16 as a rotameric mixture. $^1$H NMR (500 MHz, $CDCl_3$ δ 7.21–7.01 (m), 5.41 (brs), 4.21 (dd), 4.08 (dd), 4.12 (d), 3.88 (d), 3.95 (s), 3.91 (s), 3.49 (d), 3.39 (dt), 2.80–2.62 (m), 2.38 (brt), 2.09 (br s), 1.87–1.20 (m). $R_f$ 0.9 (1:3:26 Methanol:ether:methylene chloride).

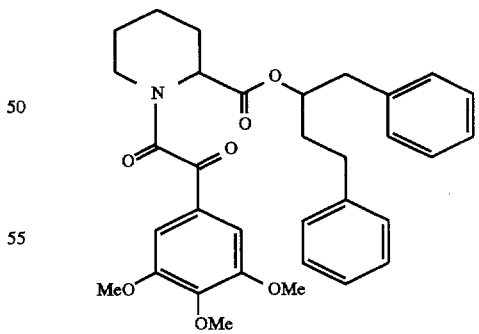

Example 7

Synthesis of (R and S)-1-Phenyl-7-(2-pyridyl)-4-heptyl (S)-N-(tert-butylglyoxyl)pipecolate (21)

(E and Z)-3-(1,3-Dioxan-2-yl)-1-(2-pyridyl)-1-propene (148 and 149).

To a suspension of 4.6 g (10.2 mmol) of [2-(1,3-dioxan-2yl)ethyl]triphenylphosphonium bromide (Aldrich Chemical Co.) in 50 mL of THF at 0° C. was added 6.4 mL (10.2 mmol) of n-butyl lithium (1.6M in hexanes) and the resulting red solution was allowed to stir at 0° C. for 0.5 h. To this solution was added 880 µL (9.3 mmol) of 2-pyridinecarboxaldehyde (Aldrich Chemical Co.). The reaction mixture was allowed to stir at room temperature for 1 h and was then poured into water and partitioned with ether. The combined either extracts were dried over MgSO$_4$ and concentrated. Flash chromatography (elution with 3:1 hexane:ethyl acetate) gave 0.43 g of E-3-(1,3-dioxan-2-yl)-1-(2-pyridyl)-1-propene (148) and 1.12 g of Z-3-(1,3-dioxan-2-yl)-1-(2-pyridyl)-1-propene (149). $^1$H NMRs consistent with structures.

1-(1,3-Dioxan-2-yl)-3-(2-pyridyl)propane (150).

Through a suspension of 800 mg (4.2 mmol) of olefin 149 and 100 mg of 10% palladium on carbon was bubbled a steady stream of hydrogen gas for a period of 10 min. The reaction mixture was then filtered through celite and concentrated to give 805 mg of the acetal 150 as a colorless oil. $^1$H NMR consistent with structure.

4-(2-Pyridyl)-1-butyraldehyde (151).

A solution of 420 mg (2.2 mmol) of acetal 150 in 4.0 mL of THF and 3.0 mL of 4N HCl was stirred at room temperature for 1.5 h and was then neutralized by the slow addition of solid NaHCO$_3$. The reaction mixture was extracted with ethyl acetate, dried over MgSO$_4$ and concentrated to yield 288 mg of the aldehyde 151. $^1$H NMR consistent with structure.

(R and S)-1-Phenyl-7-(2-pyridyl)-4-heptanol (152).

The alcohol 152 was prepared from 288 mg (1.93 mmol) of aldehyde 151 and 2.3 mL (2.3 mmol) of 120 in 3.0 mL of THF as described above for the synthesis of alcohol 121 in Example 1 to give 520 mg of the crude alcohol 152. $^1$H NMR consistent with structure.

(S)-Boc-Pipecolyl-(R and S)-1-Phenyl-7-(2-pyridyl)-4-heptyl ester (153).

The ester 153 was prepared from 520 mg (1.93 mmol) of alcohol 152, 442 mg (1.93 mmol) of (S)-Boc-L-pipecolic acid, 370 mg (1.93 mmol) of EDC and a catalytic amount of DMAP in 4.0 mL of CH$_2$Cl$_2$ and 4.0 mL of DMF as described above for the synthesis of 122 in Example 1. Flash chromatography (elution with 3:1 hexane: ethyl acetate) gave 740 mg of the diastereomeric ester 153 as an oil. $^1$H NMR consistent with structure.

(R and S)-1-Phenyl-7-(2- pyridyl)-4-heptyl (S)-pipecolate (154).

The amine 154 was synthesized by treating 740 mg (1.54 mmol) of the ester 153 with 2.0 mL of trifluoroacetic acid in 5.0 mL of CH$_2$Cl$_2$ as described above for the preparation of 123 in Example 1 giving 580 mg of the diastereomeric amine 154 as an oil. $^1$H NMR consistent with structure.

(R and S)-1-Phenyl-7-(2-pyridyl)-4-heptyl (S)-N-methyloxalylpipecolate (155).

To a solution of 48 mg (0.13 mmol) of the amine 154 in 1.0 mL of CH$_2$Cl$_2$ at 0° C. was added 33 µL (0.19 mmol) of N,N-diisopropylethylamine and 14 µL (0.15 mmol) of methyloxalyl chloride and the resulting solution was warmed to room temperature and allowed to stir overnight. The reaction mixture was diluted with ethyl acetate, washed with saturated NH$_4$Cl and brine, dried over MgSO$_4$ and then concentrated. Flash chromatography (elution with 25–30% ethyl acetate in hexane) gave 49 mg of the diastereomeric amide 155 as a mixture of rotamers. $^1$H NMR consistent with structure.

(R and S)-1-Phenyl-7-(2- pyridyl-4-heptyl (S)-N-(tert-butylglyoxyl)pipecolate (21).

To a solution of the amide 155 in 1.2 mL of THF at –78° C. was added tert-butyl lithium dropwise until TLC showed the consumption of the starting material. The reaction mixture was quenched with saturated NH$_4$Cl and partitioned with ethyl acetate. The combined organic extracts were washed with brine, dried over MgSO$_4$ and concentrated. Flash chromatography (elution with 30% ethyl acetate in hexane) gave the diastereomeric amide 21 as a mixture of rotamers. $^1$H NMR (500 MHz, CDCl$_3$) δ 8.50 (t), 7.57 (t), 7.20–7.05 (m), 5.23 (d), 5.18 (d), 4.56 (d), 4.44 (br d), 4.13 (d), 3.69 (br d), 3.37 –3.28 (m), 3.13–3.00 (m), 2.85–2.70 (m), 2.65–2.54 (m), 2.38– 2.15 (m), 1.82–1.65(m), 1.56–1.44(m), 1.55–1.30(m), 1.27(s), 1.21 (s).

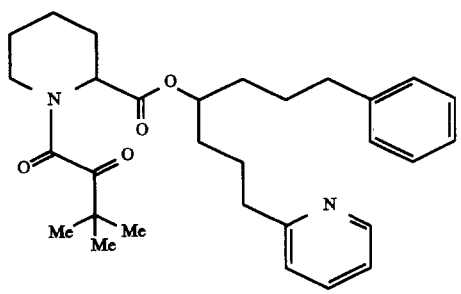

21

Example 8

Synthesis of (S)-1-[2-Oxo-2-(3,4,5-trimethoxyphenyl)acetyl]piperidine-2-carboxylic acid (R and S)-1-(3-phenylpropyl)-4-pyridin-3-yl-butyl ester (9)

(E and Z)-3-(1,3-Dioxan-2-yl)-1-(3-pyridyl)-1-propene (156).

To a suspension of 9.9 g (22.4 mmol) of [2-(1,3-dioxan-2-yl)ethyl]triphenylphosphonium bromide (Aldrich Chemical Co.) in 50 mL of THF at 0° C. was added 14.0 mL (22.4 mmol) of butyl lithium (1.6M in hexanes) and the resulting red solution was allowed to stir at 0° C. for 0.5 h. To this solution was added 1.8 mL (18.7 mmol) of 3-pyridinecarboxaldehyde (Aldrich Chemical Co.) and the reaction mixture was allowed to stir at room temperature for 1.5 h and was then poured into water and partitioned with ether. The combined ether extracts were dried over MgSO$_4$ and concentrated. Flash chromatography (elution with 2:1 hexane:ethyl acetate) gave 3.3 g of the alkene 156 as a mixture of olefin isomers. $^1$H NMR consistent with structure.

1-(1,3-Dioxan-2-yl)-3-(3-pyridyl)propane (157).

Through a solution of 3.2 g (16.7 mmol) of olefin 156 and 300 mg of 10% palladium on carbon was bubbled a steady stream of hydrogen gas for a period of 10 min. The reaction mixture was then filtered through celite and concentrated to give 2.8 g of the acetal 157 as a colorless oil. $^1$H NMR consistent with structure.

4-(3-Pyridyl-1-butyraldehyde (158).

A solution of 1.5 g (7.8 mmol) of acetal 157 in 10.0 mL of THF and 10.0 mL of 4N HCl was stirred overnight at room temperature and was then neutralized by the slow addition of solid NaHCO$_3$. The reaction mixture was extracted with ethyl acetate, dried over MgSO$_4$ and concentrated to yield 1.1 g of the aldehyde 158. $^1$H NMR consistent with structure.

(R and S)-1-Phenyl-7-(3-pyridyl)-4-heptanol (159).

The alcohol 159 was prepared from 1.1 g (7.4 mmol) of aldehyde 158 and 8.1 mL (8.1 mmol) of 120 in 30.0 mL of THF as described above for the synthesis of 121 in Example 1 to give 1.9 g of the crude alcohol 159. $^1$H NMR consistent with structure.

(S)-Boc-Pipecolyl-(R and S)-1-Phenyl-7-(3-pyridyl)-4-heptyl ester (160).

The ester 160 was prepared from 1.65 g (6.12 mmol) of alcohol 159, 1.54 g (6.73 mmol) of (S)-Boc-pipecolic acid, 1.29 g (6.73 mmol) of EDC and a catalytic amount of DMAP in 8.0 mL of $CH_2Cl_2$ and 8.0 mL of DMF as described above for the synthesis of 122 in Example 1. Flash chromatography (elution with 2:1 hexane:ethyl acetate) gave 1.42 g of the diastereomeric ester 160 as an oil. $^1$H NMR consistent with structure.

(R and S)-1-Phenyl-7-(3-pyridyl)-4-heptyl (S)-pipecolate (161).

The amine 161 was synthesized by treating 1.42 g (2.95 mmol) of the ester 160 with 2.0 mL of trifluoroacetic acid in 8.0 mL of $CH_2Cl_2$ as described above for the preparation of 123 in Example 1 giving 1.02 g of the diastereomeric amine 161 as an oil. $^1$H NMR consistent with structure.

(R and S)-1-phenyl-7-(3-pyridyl)-4-heptyl (S)-N-(3,4,5-trimethoxy-phenylglyoxyl)pipecolate (9).

The ester 9 was prepared from 995 mg (2.61 mmol) of the amine 161, 645 mg (2.87 mmol) of the acid 124 and 551 mg (2.87 mmol) of EDC in 6.0 mL of $CH_2Cl_2$ as described above in the synthesis of ester 3 in Example 1. Flash chromatography (elution with 3:1 acetone:hexane) gave 976 mg of the diasteromeric amide 9 as a mixture of rotamers. $^1$H NMR consistent with structure.

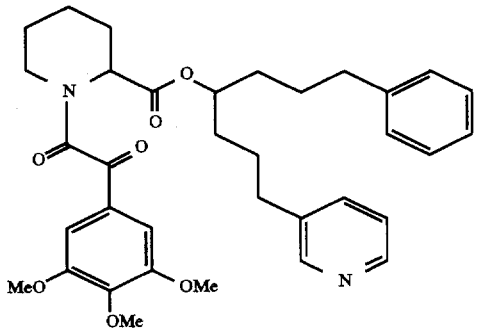

9

Example 9

(R and S)-1-phenyl-7-(3-pyridyl)-4-heptyl (S)-N-(3,4,5-trimethoxyphenylglyoxyl)pipecolate N-oxide (22).

To a solution of 15 mg (0.02 mmol) of the amide 9 in 2.0 mL of $CH_2Cl_2$ at room temperature was added 9.3 µL (0.03 mmol) of 55% 3-chloroperoxybenzoic acid and the resulting solution was allowed to stir overnight at room temperature. Flash chromatography (elution with 100% acetone) gave 12.6 mg of the N-oxide 22 as a mixture of rotamers. $^1$H NMR (500 MHz $CDCl_3$) δ 8.10 (m), 7.46–7.02 (m), 5.88 (d), 5.80 (d), 5.06–5.00 (m), 4.95–4.89 (m), 4.61 (m), 4.31 (dd), 3.87 (s), 3.84 (s), 3.83 (s), 3.81 (s), 3.78 (s), 3.50 (br d), 3.27 (ddd), 3.12 (ddd), 3.00 (ddd), 2.67–2.49 (m), 2.32 (br d), 1.86–1.78 (m), 1.55–1.50 (m), 1.39–1.22 (m).

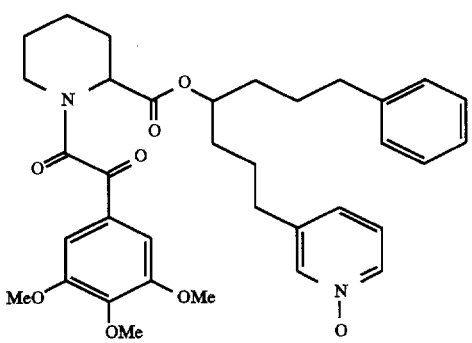

22

Example 10

Synthesis of (R and S)-1-Phenyl-7-purinyl-4-heptyl (S)-N-(3,4,5-trimethoxyphenylglyoxyl)pipecolate (25)

4-Chlorobutyraldehyde (162).

To a solution of 19.1 g (0.16 mol) of 4-chloro-1-butanol (Aldrich Chemical Co.) in 50 mL of $CH_2Cl_2$ at 0° C. was added 1.0 g of powdered 4 Å molecular sieves and 38.7 g (0.18 mol) of pyridinium dichromate and the resulting suspension was stirred at 0° C. for 45 min. The reaction mixture was diluted with ether, filtered through celite and concentrated. The residue was vacuum distilled (bp 45°–55° C.) to yield 5.0 g of the aldehyde 162 as an oil. $^1$H NMR consistent with structure.

(R and S)-1-Chloro-7-phenyl-4-heptanol (163).

The alcohol 163 was prepared from 182 mg (1.7 mmol) of aldehyde 162 and 1.9 mL (1.9 mmol) of 120 in 20.0 mL of THF as described above for the synthesis of 121 in Example 1 to give 128 mg of the alcohol 163 (flash chromatography in 100% methylene chloride). $^1$H NMR consistent with structure.

(S)-Boc-Pipecolyl-(R and S)-1-Chloro-7phenyl-4-heptyl ester (164).

The ester 194 was prepared from 128 mg (0.56 mmol) of alcohol 163, 156 mg (0.68 mmol) of (S)-Boc-pipecolic acid, 130 mg (0.68 mmol) of EDC and a catalytic amount of 4-pyrrolidinopyridine in 2.0 mL of $CH_2Cl_2$ as described above for the synthesis of 122 in Example 1. Flash chromatography (elution with 1:5:14 ether:methylene chloride:hexane) gave 159 mg of the diastereomeric ester 164. $^1$H NMR consistent with structure.

(S)-Boc-Pipecolyl-(R and S)-1-Phenyl-7purinyl-4-heptyl ester (165).

To a solution of 34 mg (0.28 mmol) of purine in 3.0 mL of DMF at room temperature was added 8.4 mg (0.28 mmol) of solid NaH (80% in mineral oil) and the resulting solution was allowed to stir at room temperature for 10 min. To this reaction mixture was added 62 mg (0.14 mmol) of the ester 164 and 10 mg of NaI and this mixture was stirred overnight at room temperature and then concentrated to dryness. The residue was dissolved into ethyl acetate, washed sequentially with water, saturated $NaHCO_3$, and brine and then dried over $MgSO_4$ and concentrated. Flash chromatography (elution with 15% 5:10:85 $NH_4OH$:MeOH:$CH_2Cl_2$ in $CH_2Cl_2$) gave 56 mg of the substituted purine 165 as an oil. $^1$H NMR consistent with structure.

(R and S)-1-Phenyl-7-purinyl-4-heptyl (s)-pipecolate hydrochloride salt (166). Anhydrous HCl was bubbled into a solution of 53.7 mg (0.10 mmol) of the ester 165 in 10 ml of EtOAc at −20° C. for 10 min and then the reaction mixture was purged with N₂. Concentration gave the crude amine 166 as the hydrochloride salt. ¹H NMR consistent with structure.

(R and S)-1-Phenyl-7-purinyl-4-heptyl (S)-N-(3,4,5-trimethoxyphenylglyoxyl)pipecolate (25).

To a slurry of the crude amine hydrochloride 166 in CH₃CN at room temperature was added 45 μL (0.26 mmol) of N,N-diisopropylethylamine, 37 mg (0.15 mmol) of acid 124, and 54 mg (0.12 mmol) of the BOP reagent and the resulting mixture was stirred at room temperature for two days and then was concentrated to dryness. The residue was reconstituted into 75 mL of ethyl acetate and then sequentially washed with water, 5% KHSO₄, saturated NaHCO₄ and brine and then dried over MgSO₄ and concentrated. Flash chromatography (elution with 1:4:36 MeOH:Et₂O:CH₂Cl₂) gave 26.5 mg of the diastereomeric amide 25 as a rotameric mixture. ¹H NMR (500 MHz, CDCl₃) δ 9.11 (s), 8.95 (m), 8.09 (m), 7.36–7.05 (m), 5.31 (m), 4.28 (m), 3.90 (m), 3.46 (br t), 3.20 (m), 2.58 (m), 2.28 (br d), 2.17–1.18 (m), R_f 0.1 (30% ether in methylene chloride).

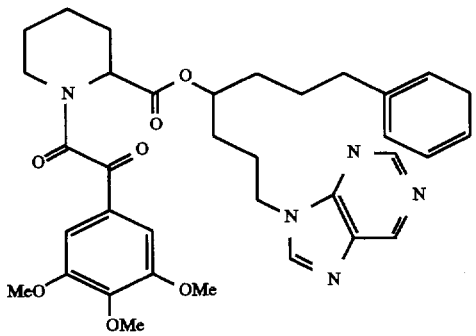

Example 11

Synthesis of (S)-1-[2-Oxo-2-(3,4,5-trimethoxyphenyl)acetyl]piperidine-2-carboxylic acid (R and S)-4-[4-(morpholine-4-carbonyl)phenyl]-1-(3-phenylpropyl)butyl ester (44)

4-Formylbenzoic acid methyl ester (167).

To a suspension of 9.6 g (63.6 mmol) of 4-carboxybenzaldehyde (Aldrich Chemical Co.) in 100 mL of CH₂Cl₂ at 0° C. was added excess trimethylsilyldiazomethane and the resulting mixture was allowed to stir at 0° C. for 1 h. The mixture was poured into saturated aqueous NaHCO₃ and extracted three times with ethyl acetate. The combined organic extracts were dried over MgSO₄, filtered and concentrated to give 4.3 g of the ester 167 as an oil. ¹H NMR consistent with the product.

(E and Z)-4-[3-[1,3]-Dioxolan-2-yl -propenyl)benzoic acid methyl ester (168).

The olefin was prepared from 4.3 g (26.2 mmol) of the aldehyde 167, 13.94 g of [1-(1,3-dioxan-2-yl)ethyl] triphenylphosphoniumbromide and 12.6 mL (32.0 mmol) of n-BuLi in 75 mL of THF as described for the synthesis of 156 in Example 8. Flash chromatography (elution with 10% ethyl acetate in hexane) gave 3.27 g of the olefin 168. ¹H NMR consistent with the product.

4-[3-[1,3]-Dioxolan-2-yl-propyl)benzoic acid methyl ester (169).

The olefin 169 (3.21 g, 12.9 mmol) was hydrogenated over 328 mg of 10% Pd/C in 50 mL of EtOH as described for compound 157 in Example 8. Filtration and evaporation gave 2.85 g of 169 as an oil. ¹H NMR consistent with the product.

[4-(3-[1,3]-Dioxan-2-yl-propyl)phenyl]methanol (170).

To a solution of 2.85 g (11.4 mmol) of ester 169 in 25 mL of THF at 0° C. was added 4.4 mL (24.7 mmol) of diisobutylaluminum hydride and the resulting mixture was allowed to stir at 0° C. for 15 min. The reaction was quenched with saturated potassium sodium tartrate and extracted three times with ethyl acetate. The combined organic extracts were dried over MgSO₄, filtered and concentrated to yield 2.58 g of the crude alcohol 170 as an oil. ¹H NMR consistent with the product.

2-[3-(4-tert-Butyldiphenylsilyloxymethylphenyl)propyl]-[1,3]-dioxolane (171).

To a solution of 2.58 g (11.6 mmol) of alcohol 170 and 1.19 g (17.5 mmol) of imidazole in 50 mL of CH₂Cl₂ was added 3.4 mL (13.1 mmol) of tert-butylchlorodiphenyl silane and the resulting mixture was allowed to stir at room temperature for 1 h. The mixture was then diluted with ethyl acetate and washed with 0.5N HCl. The organic layer was dried over MgSO₄, filtered and concentrated. Flash chromatography (elution with 5% ethyl acetate in hexane) afforded 5.5 g of 171. ¹H NMR consistent with the product.

4-(4-tert-Butyldiphenylsilyloxymethyl-phenyl) butyraldehyde (172).

To a solution of 5.5 g (11.9 mmol) of the dioxolane 171 in 40 mL of THF at room temperature was added 40 mL of 4.0N HCl and the resulting solution was allowed to stir for 1 h. The mixture was neutralized with solid K₂CO₃, extracted with ethyl acetate and concentrated. The crude mixture was dissolved into 25 mL of CH₂Cl₂ to which was added 600 mg (8.8 mmol) of imidazole and 1.9 mL (7.3 mmol) of tert-butylchlorodiphenyl silane. The resulting mixture was allowed to stir overnight at room temperature and was then poured into 0.5N HCl and extracted with ethyl acetate. The organics were dried over MgSO₄, filtered and concentrated. Flash chromatography (elution with 8% ethyl acetate in hexane) gave 2.12 g of the aldehyde 172 as an oil. ¹H NMR consistent with the product.

1-(4-tert-Butyldiphenylsilyloxymethylphenyl)-7-phenyl-heptan-4-ol (173).

The alcohol 173 was prepared from 2.12 g (5.0 mmol) of 172 and 9.0 mL (9 mmol) of 120 in 50 mL of THF as described for the synthesis of 121 in Example 1. Flash chromatography (elution with 10% ethyl acetate in hexane) gave 3.3 g of the alcohol 173. ¹H NMR consistent with the product.

(S)-Piperidine-1,2-dicarboxylic acid (R and S)-2-[4-(4-tert-butyldiphenylsilyloxymethylphenyl)-1-(3-phenylpropyl)butyl]ester 1-tert-butyl ester (174).

The ester 174 was prepared from 3.3 g (6.15 mmol) of alcohol 173, 1.7 g (7.4 mmol) of (S)-Boc-pipecolic acid, 1.4 g (7.3 mmol) of EDC and a catalytic amount of DMAP in 35 mL of CH₂Cl₂ as described above for the synthesis of 122 in Example 1. Flash chromatography (elution with 5% ethyl acetate in hexane) provided 2.4 g of the ester 174. ¹H NMR consistent with the product.

(S)-Piperidine-1,2-dicarboxylic acid 1-tert-butyl ester (R and S)-2-[4-(4-hydroxymethylphenyl-1-(3-phenylpropyl) butyl ester(175).

To a solution of 750 mg (1.0 mmol) of the ester 174 in 10 mL of THF was added 1.1 mL (1.1 mmol) of a solution of tetrabutyl-ammonium fluoride (1.0M in THF) and the resulting mixture was allowed to stir at room temperature for 15 min. The mixture was diluted with ethyl acetate, washed with 5% KHSO₄, dried over MgSO₄ and concentrated. Flash chromatography (elution with 20% ethyl acetate in hexane) gave 308 mg of the alcohol 175. ¹H NMR consistent with the product.

(S)-Piperidine-1,2-dicarboxylic acid 1-tert-butyl ester (R and S)-2-[4-(4-carboxyphenyl)-1-(3-phenylpropyl)butyl] ester (176).

To a solution of 326 mg (0.64 mmol) of the alcohol 175 in 3.0 mL of acetone was added 0.5 mL (1.27 mmol) of the Jones reagent and the resulting mixture was allowed to stir at room temperature for 1 h, and was then filtered through a pad of celite and concentrated. Flash chromatography (elution with 2% MeOH in $CH_2Cl_2$) gave 155 mg of the acid 176. $^1$H NMR consistent with the product.

(S)-Piperidine-2-carboxylic acid (R and S)-4-(4-carboxyphenyl)-1-3-phenylpropyl)butyl ester Trifluoroacetate salt (177)

To a solution of 155 mg (0.3 mmol) of the acid 176 in 3.0 mL of $CH_2Cl_2$ was added 500 µL of trifluoroacetic acid and the resulting solution was allowed to stir at room temperature for 3 h at which time the volatiles were removed in vacuo. The crude residue was suspended in 5.0 mL of dry benzene and the volatiles were removed to yield an anhydrous sample of the salt 177.

(S)-1-[2-Oxo-2-(3,4,5-trimethoxyphenyl)acetyl]piperidine-2-carboxylic acid (R and S)-4-(4-carboxyphenyl)-1-(3-phenylpropyl)butyl ester (178).

To a suspension of 159 mg (0.3 mmol) of the salt 177 in 2.5 mL of $CH_2Cl_2$ at 0° C. was added 110 µL (0.63 mmol) of N,N-diisopropylethylamine and then 40 µL (0.31 mmol) of chlorotrimethylsilane and the resulting mixture was allowed to stir at 0° C. for 30 min. To this solution was added 85 mg (0.44 mmol) EDC and 106 mg (0.44 mmol) of the acid 124 and the reaction mixture was allowed to stir at room temperature overnight. The mixture was diluted with ethyl acetate and washed with 0.5N HCl, water, brine, dried over $MgSO_4$ and concentrated. Flash chromatography (elution with 30% MeOH in $CH_2Cl_2$) gave 97 mg of the product 178 as a mixture of rotamers. $^1$H NMR consistent with the product.

(S)-1-[2-Oxo-2-(3,4,5-trimethoxyphenyl)acetyl]piperidine-2-carboxylic acid (R and S)-4-(4-(morpholine-4-carbonyl)phenyl]-1-(3- phenylpropyl)butyl ester (44).

To a solution of 11.2 mg (17 µmol) of the acid 178 in 1.0 mL of $CH_2Cl_2$ was added 4.1 mg (21.4 µmol) of EDC and 1.8 mg (20.7 µmol) of morpholine and the resulting solution was allowed to stir overnight at room temperature. Flash chromatography (elution with 20% MeOH in $CH_2Cl_2$) gave 7.6 mg of the amide 44 as a mixture of rotamers. $^1$H NMR (500 MHz $CDCl_3$) δ 7.32 (d), 7.30 (d), 7.26 (s), 7.21–7.08 (m), 5.33 (m), 5.01 (m), 4.92 (m), 3.92 (s), 3.89 (s), 3.88 (s), 3.87 (s), 3.86 (s), 3.85 (s), 3.81–3.53 (m), 3.42 (brd), 3.29–3.21 (m), 3.05 (m), 2.61 (m), 2.42 (dd), 2.31 (d), 2.12 (m), Y1.83 (m), 1.73–1.42 (m), 1.42–1.20 (m).

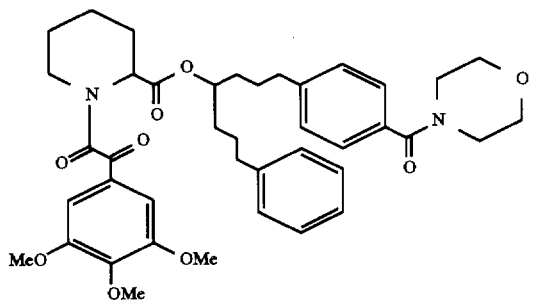

44

Example 12—NMR DATA

We have prepared other compounds of formula (I) by methods substantially similar to those described in the above Examples 1–11 and those illustrated in Schemes 1–3. The NMR spectral data for these compounds are summarized below. Compounds are numbered according to the numbering scheme of Table 1.

Compound 2.

$^1$H NMR(500 MHz $CDCl_3$), (mixture of diastereomers, mixture of rotomers) δ 8.42–8.33(m), 7.51(d), 7.42(d), 7.38 (s), 7.31(d), 7.29–7.05(m), 5.01(s,br), 4.8(m), 4.71(m), 4.62 (m), 3.92–3.83(m), 3.81(d), 3.60–3.51(m), 3.50–3.45(m), 2.65–2.51(m), 2.50–2.39(m), 2.38–2.22(m), 2.05(m), 1.95 (m), 1.81–1.68(m), 1.67–1.49(m), 1.48–1.31(m), 1.22(s).

Compound 5

$^1$H NMR(500 MHz $CDCl_3$), (mixture of diastereomers, mixture of rotomers) δ 7.39–6.80(m), 6.75(d), 5.47(m), 4.55(m), 4.45(m), 3.95–3.78(m), 3.49–3.40(m), 3.22–3.11 (m), 2.49–2.38(m), 1.88–1.67(m), 1.61–1.42(m), 1.37–1.14 (m).

Compound 6

$^1$H NMR(500 MHz $CDCl_3$), (mixture of diastereomers, mixture of rotomers) δ 7.36–7.19(m), 7.18–7.02(m), 5.77(t), 5.65(m), 5.39(m), 4.60–4.52(m), 4.35(m), 3.93–3.82(m), 3.71–3.63(m), 3.48–3.42(m), 3.41–3.34(m), 3.28–3.19(m), 3.12–3.07(m), 2.65–2.58(m), 2.57–2.48(m), 2.42–2.31(m), 2.02–1.94(m), 1.91–1.21(m), 1.11–1.02(m).

Compound 10

$^1$H NMR(500 MHz $CDCl_3$), (mixture of diastereomers, mixture of rotomers) δ 7.35–6.98(m), 5.35(d), 5.3–5.14(m), 4.52(bd), 4.24(bs), 3.97–3.87(m), 3.49(t), 3.12(q), 3.00–2.56(m), 2.46(t), 2.32(d), 2.18(d), 2.11(d), 1.93(d), 1.83–1.56(m), 1.55–1.38(m), 1.32–1.18(m), 0.94–0.72(m).

Compound 12

$^1$H NMR(500 MHz $CDCl_3$), (mixture of diastereomers, mixture of rotomers) δ 7.37(s), 7.31–7.06(m), 6.98(d), 5.39 (dd), 5.09–5.00(m), 4.99–4.93(m), 4.73(d), 4.38(m), 3.98–3.86(m), 3.91(s), 3.50(d), 3.34–3.24(m), 3.09(t), 2.73–2.16(m), 2.02–1.24(m).

Compound 13

$^1$H NMR(500 MHz $CDCl_3$), (mixture of diastereomers, mixture of rotomers) δ 7.38(s), 7.29–7.21(m), 7.20–7.03(m), 6.99(d), 6.88(d), 6.82–6.73(m), 5.40–5.32(m), 5.04–4.98 (m), 4.97–4.91(m), 4.61(d), 4.37(d), 3.93–3.83(m), 3.81–3.74(m), 3.53–3.47(d,br), 3.32–3.22(m), 3.11–3.04 (m), 2.65–2.12(m), 1.97–1.21(m).

Compound 14

$^1$H NMR(500 MHz $CDCl_3$), (mixture of diastereomers, mixture of rotomers) δ 8.04(d), 7.97(t), 7.59–7.48(m), 7.47–7.41(m), 7.31–7.22(m), 7.21–7.02(m), 6.98–6.91(m), 6.82–6.76(m), 5.43–5.38(m), 5.12–5.03(m), 4.93(m), 4.65–4.60(m), 4.38(m), 3.79(m), 3.53–3.48(m), 3.23(q), 3.11–2.99(m), 2.68–2.29(m), 2.19(t), 1.98–1.31(m).

Compound 15

$^1$H NMR(500 MHz $CDCl_3$), (mixture of diastereomers, mixture of rotomers) δ 8.05–7.92(m), 7.78(d), 7.47–7.03 (m), 6.42(bs), 5.33(d), 5.01(m), 4.94(m), 4.59(bd), 4.32–4.14(m), 4.08–4.00(m), 3.97–3.84(m), 3.77–3.68(m), 3.45(bd), 3.17–3.08(m), 2.97(t), 2.60(t), 2.48(t), 2.35–2.21 (m), 2.11(d), 2.05–1.10(m), 0.91–0.79 (m).

Compound 17

$^1$H NMR (500 MHz $CDCl_3$), (mixture of diastereomers, mixture of rotomers) δ 7.38–6.92(m), 6.82–6.71(m), 5.38–5.29(m), 5.06–4.85(m), 4.60(d), 4.31(d), 3.94–3.81 (m), 3.79–3.70(m), 3.51–3.41(m), 3.23(t,br), 3.06(t), 2.62–2.22(m), 2.15(d), 1.82–1.29(m).

Compound 18

¹H NMR(500 MHz CDCl₃), (mixture of diastereomers, mixture of rotomers) δ 8.55–8.38(m), 8.08–8.00(m), 7.98 (d), 7.68(t), 7.59(t), 7.50–7.45(m), 7.45–7.41(m), 7.29–7.25 (m), 7.25–7.08 (m), 5.40 (m), 5.11(m), 4.93(m), 4.61(brd), 4.38(m), 3.61(m), 3.51–3.46(m), 3.26–3.15(m), 3.08–2.96 (m), 2.70–2.61(m), 2.58–2.49(m), 2.38(brd), 2.19(brd), 1.83–1.78(m), 1.78–1.59(m), 1.56–1.43(m), 1.41–1.24(m).

Compound 19

¹H NMR(500 MHz CDCl₃), (mixture of diastereomers, mixture of rotomers) δ 8.52–8.49(m), 8.04(d), 7.96(d), 7.64 (t), 7.61–7.57(m), 7.52(t), 7.46–7.41(m), 7.26–7.22(m), 7.17 (t), 7.12–7.08(m), 5.41(d), 5.12(m), 4.93(m), 4.61(brd), 4.38 (d), 3.89–3.83(m), 3.67–3.61(m), 3.53–3.48(m), 3.28–3.19 (m), 3.06–3.00(m), 2.83(brt), 2.72(brt), 2.65(brt), 2.52(brt), 2.48(brd), 2.21(brd), 1.89–1.73(m), 1.73–1.70(m), 1.70–1.48(m), 1.48–1.33(m).

Compound 20

¹H NMR(500 MHz CDCl₃), (mixture of diastereomers, mixture of rotomers) δ 8.50(d), 7.61(dd), 7.28–7.25(m), 7.21–7.16(m), 7.12(dd), 5.38(brd), 5.09–5.02(m), 4.93–4.90 (m), 4.62(brd), 4.34(m), 3.94(s), 3.92(s), 3.91(s), 3.90(s), 3.89(s), 3.49(brddd), 3.28(ddd), 3.09(dd), 2.83(t), 2.74(m), 2.63(brd), 2.49(dd), 2.36(brd), 2.19(brd), 1.86–1.70(m), 1.70–1.62(m), 1.59–1.52(m), 1.48–1.23(m).

Compound 23

¹H NMR(500 MHz CDCl₃), (mixture of diastereomers, mixture of rotomers) δ 8.30(d), 8.28(d), 7.79(d), 7.34(s), 7.31–7.00(m), 6.43(s), 5.33(d), 5.06(d), 4.94(m), 4.59(d), 4.42–4.10(m), 4.04(s), 3.96(s), 3.94(s), 3.91(s), 3.81(s), 3.77 (s), 3.48(d), 3.27(dt), 3.05(dt), 2.67–2.47(m), 2.32(d), 2.14 (d), 2.03–1.22 (m), 0.94–0.81 (m).

Compound 26 ¹H NMR(500 MHz CDCl₃), (mixture of diastereomers, mixture of rotomers) δ 7.32(d), 7.27–6.99 (m), 5.34–5.28(m), 5.00(s,br), 4.61(d), 4.30(d), 3.92–3.81 (m), 3.02(t), 2.54–2.48(m), 2.47–2.39(m), 2.34–2.22(m), 2.14(d), 1.82–1.14(m).

Compound 27

¹H NMR(500 MHz CDCl₃), (mixture of diastereomers, mixture of rotomers) δ 8.46–8.38(m), 7.68–7.50(m), 7.49–7.30(m), 7.29–7.08(m), 5.48(m), 5.16–5.02(m), 4.98–4.90(m), 4.60(d), 4.32(d), 3.51–3.42(m), 3.26–3.12 (m), 3.11–2.98(m), 2.65–2.42(m), 2.32(d,br), 2.14(d,br), 1.83–1.22(m).

Compound 28

¹H NMR(500 MHz CDCl₃), (mixture of diastereomers, mixture of rotomers) δ 8.45–8.32(m), 7.62–7.53(m), 7.52–7.43(m), 7.42–7.05(m), 6.09–5.98(m), 5.44–5.25(m), 5.09(s,br), 4.92(s,br), 4.64–4.51(m), 4.31(d), 3.50–3.41(m), 3.24–3.12(m), 3.07–2.94(m), 2.68–2.45(m), 2.32(d,br), 2.14 (d,br), 1.83–1.26(m).

Compound 29

¹H NMR(500 MHz CDCl₃), (mixture of diastereomers, mixture of rotomers) δ 8.44–8.37(m), 7.58–7.51(m), 7.50–7.08(m), 5.35(t,br), 5.10(s,br), 4.93(s,br), 4.68–4.54 (m), 4.32(d), 3.51–3.42(m), 3.25–3.12(m), 3.00(q), 2.69–2.45(m), 2.38–2.29(m), 2.14(d,br), 1.82–1.20(m).

Compound 30

¹H NMR(500 MHz CDCl₃), (mixture of diastereomers, mixture of rotomers) δ 7.35(s), 7.29–7.20(m), 7.19–7.02(m), 6.89(m), 6.77(m), 5.34(d), 5.03(m), 4.91(m), 4.61(d), 4.33 (d), 3.95–3.88(m), 3.48(d), 3.31–3.21(m), 3.05(t,br), 2.87–2.43(m), 2.32(d,br), 2.18(d,br), 1.87–1.21(m).

Compound 31

¹H NMR(500 MHz CDCl₃), (mixture of diastereomers, mixture of rotomers) δ 8.00 (s,br), 7.34(s,br), 7.31–7.02(m), 5.34(s,br), 5.31(s,br), 5.03(s,br), 4.92(d,br), 4.61(d,br), 4.33 (s,br), 3.96–3.84(m), 3.48(d,br), 3.24(s,br), 2.76–2.42(m), 2.32(d,br), 2.15(m), 1.87–1.20(m).

Compound 32

¹H NMR(500 MHz CDCl₃), (mixture of diastereomers, mixture of rotomers) δ 7.38(d), 7.30–7.08(m), 7.07–7.03(d), 5.35–5.31(m), 4.98(m), 4.88(m), 4.59(m), 4.31(m), 3.97–3.86(m), 3.46(d,br), 3.29–3.18(m), 3.04(m), 2.65–2.42 (m), 2.35–2.22(m), 1.83–1.14(m), 1.10(m).

Compound 33

¹H NMR(500 MHz CDCl₃), (mixture of diastereomers, mixture of rotomers) δ 7.38(d), 7.32–7.24(m), 7.24(d), 7.21 (d), 7.01(s), 7.00(s), 6.02–7.24(m), 5.92–5.88(m), 5.38(d), 5.36(d), 4.70(ABq), 4.69(ABq), 4.64(ABq), 4.32(brd), 3.91 (s), 3.89(s), 3.88(s), 3.74(s), 3.73(s), 3.48(brddd), 3.36(brd), 3.20(ddd), 3.06–2.97(m), 2.62 (t), 2.58(t), 2.38(brd), 2.21 (brd), 2.08–2.04(m), 1.90–1.74(m), 1.73–1.46(m), 1.38–1.33(m), 1.24(t).

Compound 34

¹H NMR(500 MHz CDCl₃), (mixture of diastereomers, mixture of rotomers) δ 7.33(s), 7.30(d), 7.29(s), 7.28–7.20 (m), 7.18–7.11(m), 6.95–6.90(m), 6.83(d), 6.82(d), 6.31–6.28(m), 6.02–5.91(m), 5.43–5.40(m), 5.21(dd), 4.53 (d), 3.91(s), 3.89(s), 3.86(s), 3.85(s), 3.84(s), 3.76(s), 3.71 (s), 3.45(brddd), 3.40(brddd), 3.28(ddd), 3.15(ddd), 3.02 (ddd), 2.62(dd), 2.40(brd), 1.94–1.89(m), 1.87–1.67(m), 1.65–1.50(m).

Compound 35

¹H NMR(500 MHz CDCl₃), (mixture of diastereomers, mixture of rotomers) δ 7.34–7.29(m), 7.28–7.11(m), 7.10–6.93(m), 5.35–5.28(m), 5.09–4.98(m), 4.90(m), 4.64–4.44(m), 4.30(m), 3.95–3.81(m), 3.46(t,br), 3.31–3.19 (m), 3.03(m), 2.66–2.38(m), 2.34–2.25(m), 2.16(m), 1.85–1.19(m).

Compound 36

¹H NMR(500 MHz CDCl₃), (mixture of diastereomers, mixture of rotomers) δ 7.93–7.81(m), 7.78(s), 7.41–7.01(m), 5.32(s,br), 5.02(s,br), 4.90(m), 4.58(d), 4.31(s,br), 3.95–3.80(m), 3.45(d), 3.22(t), 3.05(m), 2.72–2.48(m), 2.47 (d), 1.83–1.43(m), 1.42–1.18(m).

Compound 37

¹H NMR(500 MHz CDCl₃), (mixture of diastereomers, mixture of rotomers) δ 7.38(s), 7.30(s), 7.30–7.02(m), 7.01 (s), 5.80–5.83(m), 5.68(dd), 5.62(dd), 5.38(d), 5.36(d), 4.66 (s), 4.65(ABq), 4.54(s), 4.32(brd), 4.28(brd), 3.90(s), 3.88 (s), 3.86(s), 3.85(s), 3.84(s), 3.78(s), 3.76(s), 3.43(brddd), 3.39(brddd), 3.24(ddd), 3.12(ddd), 3.06(ddd), 2.97(ddd), 2.62(t), 2.57(t), 2.48(brd), 2.24(brd), 2.01–1.94(m), 1.89–1.73(m), 1.72–1.65(m), 1.65–1.58(m), 1.52–1.49(m), 1.40–1.33(m), 1.12–1.08(m).

Compound 40

¹H NMR(500 MHz CDCl₃), (mixture of diastereomers, mixture of rotomers) δ 7.36(s), 7.29–7.19(m), 7.18–7.06(m), 6.89(m), 6.75(s), 5.32(s,br), 4.94(t), 3.95–3.84(m), 3.46(d, br), 3.22(m), 2.82(t), 2.61(t), 2.30(m), 1.82–1.19(m).

Compound 41

¹H NMR(500 MHz CDCl₃), (mixture of diastereomers, mixture of rotomers) δ 7.37(d), 7.29–7.08(m), 7.04(d), 5.34 (m), 4.97(m), 4.61(d), 4.33(m), 3.96–3.88(t), 3.86(d), 3.48 (d), 3.25(m), 3.09(m), 2.65–2.52(m), 2.48(m), 2.32(d), 2.18 (d), 1.86–1.49(m), 1.48–1.15(m).

Compound 42

¹H NMR(500 MHz CDCl₃), (mixture of diastereomers, mixture of rotomers) δ 7.34(d), 7.2(m), 7.13(m), 7.0–7.1(m), 5.87(m), 5.32(m), 5.22(dd), 5.12(dd), 5.0(m), 4.89(bm), 4.57(bd), 4.30(bm), 3.80–3.95(m), 3.45(bd), 3.40(m), 3.32 (m), 3.22(dt), 3.05(bm), 2.60(m), 2.52(bm), 2.44(m), 2.30 (m), 2.15(bm), 1.75(m), 1.60(m), 1.54(m), 1.20–1.45(bm).

Compound 43

¹H NMR(500 MHz CDCl₃), (mixture of diastereomers, mixture of rotomers) δ 7.36–7.30(m), 7.29–7.20(m), 7.19–7.04(m), 5.34(m), 5.01(s,br), 4.91(m), 4.59(d), 4.31(s, br), 3.95–3.86(m), 3.47(d,br), 3.25(t,br), 3.14–2.90(m), 2.68–2.52(m), 2.45(t), 2.32(d), 2.18(d), 1.85–1.46(m), 1.45–1.18(m).

Compound 45

¹H NMR(500 MHz CDCl₃), (mixture of diastereomers, mixture of rotomers) δ 7.35(d), 7.25(m), 7.15(m), 7.10(d), 7.05(d), 5.87(m), 5.38(bd), 5.34(m), 5.22(dd), 5.14(dd), 4.95(bm), 4.88(bm), 4.58(bd), 4.32(m), 3.82–3.95(m), 3.45 (bd), 3.40(t), 3.25(m), 3.05(bm), 2.60(bm), 2.44(m), 2.34 (bd), 2.18(bd), 1.78(m), 1.48–1.70(m), 1.20–1.45(m).

Compound 46

¹H NMR(500 MHz CDCl₃), (mixture of diastereomers, mixture of rotomers) δ 7.32(s), 7.25(m), 7.16(m), 7.10(t), 5.85(m), 5.50(dt), 5.38(dd), 5.25(dd), 5.18(d), 4.58(bm), 4.35(bm), 4.15(s), 4.06(d), 4.02(t), 3.85–3.95(m), 3.46(bd), 3.25(m), 3.08(bt), 2.98(bt), 2.65(t), 2.58(t), 2.53(t), 2.35(bt), 2.20(bd), 1.70–1.88(m), 1.50–1.70(m), 1.20–1.42(m).

Compound 47

¹H NMR(500 MHz CDCl₃), (mixture of diastereomers, mixture of rotomers) δ 7.44 (d) , 7.42–7.06(m), 5.45–5.30 (m), 5.12–4.91(m), 4.03–3.83(m), 3.82–3.19(m), 2.72–2.26 (m) , 1.91–1.22(m)

Compound 48

¹H NMR(500 MHz CDCl₃), (mixture of diastereomers, mixture of rotomers) δ 7.34(d), 7.25(m), 7.20(d), 7.15(m), 7.10(d), 7.05(d), 5.88(m), 5.32(bt), 5.24(dd), 5.14(dd), 4.96 (m), 4.86(m), 4.58(bd), 4.30(bm), 3.85–3.95(m), 3.45(bd), 3.38(t), 3.32(t), 3.25(m), 3.05(m), 2.60(m), 2.32(bd), 2.16 (bd), 1.78(m), 1.48–1.72(m), 1.20–1.45(m).

Compound 49

¹H NMR(500 MHz CDCl₃), (mixture of diastereomers, mixture of rotomers) δ 7.28–7.42, 6.57–6.61(m), 6.45–6.51 (m), 5.80–5.87(dd), 5.70–5.77(dd), 5.37–5.41(brd), 5.34–5.37(brd), 4.94–5.07(dd), 4.53–4.60(brd), 4.35–4.38 (m), 3.80–3.95(m), 3.74(s), 3.38–3.50(brdd), 3.22–3.31 (ddd), 3.15–3.22(ddd), 2.96–3.08(m), 2.32–2.44(brdd), 1.73–1.85(m), 1.48–1.75(m), 1.54–1.56(d), 1.15–1.48 (m).

Compound 50

¹H NMR(500 MHz CDCl₃), (mixture of diastereomers, mixture of rotomers) δ 7.34(d), 7.24(m), 7.15(m), 7.10(d), 7.04(d), 5.85(m), 5.32(m), 5.22(dd), 5.15(m), 5.00(m), 4.58 (bd), 4.30(bs), 3.74–3.95(m), 3.44(m), 3.25(bt), 3.04(bm), 2.62(m), 2.45(t), 2.30(bd), 2.18(bd), 1.88(m), 1.78(m), 1.46–1.72(m), 1.22–1.45(m).

Compound 51

¹H NMR(500 MHz CDCl₃), (mixture of diastereomers, mixture of rotomers) δ 7.34(s), 7.25(m), 7.20(d), 7.14(m), 7.10(d), 7.06(d), 5.87(m), 5.78(dt), 5.68(m), 5.45–5.60(m), 5.35(d), 5.24(m), 5.15(d), 4.58(bd), 3.85–3.96(m), 3.45(m), 3.24(m), 3.04(m), 2.62(m), 2.56(t), 2.49(dt), 2.34(dt), 2.18 (bm), 1.48–1.82(m), 1.24–1.40(m).

Compound 52

¹H NMR(500 MHz CDCl₃), (mixture of diastereomers, mixture of rotomers) δ 7.40–7.03(m), 5.38–5.28(m), 5.02(s, br), 4.90(m), 4.60(d), 4.32(s,br), 3.99–3.87(m), 3.86–3.31 (m), 3.30–3.21(t,br), 3.11–3.02(q,br), 2.69–2.50(m), 2.47 (m), 2.32(d), 2.14(d), 1.89–1.48 (m), 1.47–1.21(m).

Compound 53

¹H NMR(500 MHz CDCl₃), (mixture of diastereomers, mixture of rotomers) δ 7.40(d), 7.35(d), 7.30(d), 7.28(s), 6.60(d), 6.55(d), 6.52(t), 6.49(t), 5.86(q), 5.78(q), 5.42(d), 5.08(s), 4.64(bd), 4.35(m), 3.88–3.98(m), 3.46(bd), 3.21 (dr), 3.05(dt), 2.36(bd), 2.18(bd), 1.80(m), 1.74(bd), 1.64(s), 1.56(d), 1.48–1.55(m), 1.40(d), 1.15–1.30(m).

Compound 54

¹H NMR(500 MHz CDCl₃), (mixture of diastereomers, mixture of rotomers) δ 8.52 (m), 7.82–7.71(m), 7.70–7.62 (m), 7.55–7.42(m), 7.38–7.01(m), 5.36–5.29(m), 5.01(m), 4.90(m), 4.79–4.67(m), 4.59(d), 4.39–4.11(m), 3.96–3.73 (m), 3.44(d), 3.22(t), 3.09–3.00(q,br), 2.72–2.41(m), 2.30 (d), 2.14(d), 1.86–1.43(m) , 1.42–1.02(m), 0.98–0.73(m).

Compound 55

¹H NMR(500MHz CDCl₃), (mixture of diastereomers, mixture of rotomers) δ 7.38(d), 7.33(d), 7.29–7.02(m), 5.32 (m), 5.01(m), 4.90(m), 4.59(m), 4.30(m), 4.08–3.51(m), 3.46(d), 329–3.18(m), 3.11–2.98(q,br), 2.81–2.32(m), 2.30 (d), 2.14(d), 1.84–1.19(m).

Compound 56

¹H NMR(500 MHz CDCl₃), (single diastereomer, mixture of rotomers) δ 7.39–7.30(m), 7.27–7.20(brs), 7.20–7.15 (brt), 7.14–7.06(brd), 5.81–5.78(brt), 5.77–5.72(brt), 5.34–5.30(brd), 5.28(s), 4.60–4.55(brd), 5.33(brs), 3.91(s), 3.88(s), 3.80(brs), 3.79–3.48(m), 3.47–3.30(brd), 3.28–3.20 (brt), 3.01–2.94(brt), 2.66–2.60(t), 2.59–2.54(t), 2.42–2.35 (brd), 2.25–2.19(brd), 2.04–1.93(m), 1.89–1.73(m), 1.72–1.65(m), 1.64–1.57(m), 1.54(brs), 1.39–1.25(m), 1.20 (brs).

Compound 57

¹H NMR(500 MHz CDCl₃), (mixture of diastereomers, mixture of rotomers) δ 7.32(d), 7.31–7.01(m), 5.31(m), 5.00(m), 4.90(m), 4.59(m), 4.30(m), 3.93–3.83(m), 3.82–3.63(m), 3.49–3.38(m), 3.22(t), 3.10–2.98(t), 2.68–2.21(m), 2.12(m), 1.82–1.21(m).

Compound 58

¹H NMR(500 MHz CDCl₃), (mixture of diastereomers, mixture of rotomers) δ 7.33–7.01(m), 5.31(m), 4.99(m), 4.89(m), 4.59(d), 4.29(m), 3.92–3.84(m), 3.83–3.64(m), 3.55–3.28(m), 3.22(t), 3.04(m), 2.63–2.22(m) , 2.14(d), 1.81–1.21(m).

Compound 59

¹H NMR(500 MHz CDCl₃), (mixture of diastereomers, mixture of rotomers) δ 7.71–7.52(m), 7.42(m), 7.39–7.04 (m), 6.72–6.59(m), 5.32(m), 5.22(m), 5.11(m), 5.01(m), 4.99–4.90(m), 4.69–4.52(m), 4.39–4.26(m), 3.99–3.79(m), 3.46(t), 3.22(t), 3.11–2.94(m), 2.72–2.40(m), 2.29(t), 2.20–2.11(m), 1.88–1.19(m), 0.89(m).

Compound 60

¹H NMR ( 500 MHz CDCl₃), (mixture of diastereomers, mixture of rotomers) δ 8.53(m), 7.80(m), 7.72–7.53(m), 7.39–7.03(m), 5.36–5.28(dd), 5.12–4.98(m), 4.92(m), 4.79–4.52(m), 4.31(m), 3.98–3.81(m), 3.45(m), 3.31–3.19 (q,br), 3.11–3.00(m), 2.72–2.43(m), 2.31(d), 2.20–2.11(m), 1.88–1.22(m).

Compound 61

¹H NMR(500 MHz CDCl₃), (mixture of diastereomers, mixture of rotomers) δ 8.45(s,br), 7.60–7.49(m), 7.38–7.21 (m), 5.38–5.31(m), 5.03–4.98(m), 3.99–3.88(m), 3.50(d,br), 3.29(q), 2.65(m), 2.38–2.31(m), 1.88–1.13(m), 0.92–0.74 (m).

Compound 62

¹H NMR(500 MHz CDCl₃), (mixture of diastereomers, mixture of rotomers) δ 8.55–8.65 (m), 7.32–7.40(m), 6.80–7.00(m), 5.74–5.78(m), 5.62–5.71(m), 5.85–5.89(brd), 5.80–5.84(brd), 5.13–5.21(m), 5.03–5.10(m), 4.77–4.81 (dd), 3.87–3.94(m), 3.80(s), 3.79(s), 3.72(s), 3.38–3.46 (brdd), 3.14–3.28(m), 2.66–2.83(m), 2.48–2.58(m), 2.28–2.48(m), 1.32–1.18(m).

Compound 63

¹H NMR (500 MHz CDCl₃), (mixture of diastereomers, mixture of rotomers) δ 8.62(d), 8.61–8.58(m), 7.64(dd), 7.59(dd), 7.32–7.24(m), 7.12(d), 6.92(dd), 6.89–6.83(m), 6.82(d), 6.79(d), 6.74(d), 5.48(d), 5.07(d), 4.60(m), 4.44 (brdd), 3.91(s), 3.90(s), 3.86(s), 3.84(s), 3.83(s), 3.78(s), 3.44(brd), 3.18(ddd), 2.92(ddd), 2.40(brt), 2.32(brt), 1.89–1.70(m), 1.62–1.48(m).

Compound 64

¹H NMR(500 MHz CDCl₃), (mixture of diastereomers, mixture of rotomers) δ 8.59(d), 8.58(d), 7.32–7.04(m), 6.99–6.80(m), 5.62(dd), 5.61(dd), 5.38(dd), 5.06(s), 5.02(d), 4.99(d), 4.53(m), 4.36(m), 3.91(s), 3.90(s), 3.89(s), 3.88(s), 3.84(s), 3.69(s), 3.61(s), 3.46(brd), 3.41(brd), 3.24(dd), 3.12 (dd), 2.62(t), 2.58(t), 2.34(brt), 1.99–1.92(m), 1.86–1.42(m).

Compound 66

¹H NMR(500 MHz CDCl₃), (mixture of diastereomers, mixture of rotomers) δ 8.56–8.51(m), 7.35–7.28(m), 7.27–7.22(m), 7.14(s), 7.07(s), 6.93–6.88(m), 6.87–6.80(m), 6.79–6.71(m), 6.65–6.62(m), 5.81(q), 5.71(q), 5.32–5.27 (m), 5.20–4.98(m), 4.57–4.47(m), 4.28–4.23(m), 3.92–3.70 (m), 3.40(brd), 3.20(brd), 3.11(ddd), 3.00–2.89(m), 2.33(d), 2.26(d), 2.20(d), 2.07(d), 1.80–1.57(m), 1.56–1.25(m), 1.24–1.17(m), 1.13–1.00(m).

Compound 67

¹H NMR(500 MHz CDCl₃), (mixture of diastereomers, mixture of rotomers) δ 8.63–8.54(m), 8.53–8.44(m), 7.38–7.11(m), 7.10–6.99(m), 6.78(d), 6.72(dd), 6.63(dd), 6.53(d), 6.44(d), 6.14(dd), 6.08(dd), 6.00(dd), 5.88(dd), 5.39 (d), 5.31(d), 5.23–4.95(m), 4.61–4.50(m), 4.32–4.29(m), 3.91(s), 3.90(s), 3.88–3.74(m), 3.71(s), 3.64–3.58(m), 3.47–3.38(m), 3.37–3.32(m), 3.24(ddd), 3.13(ddd), 3.07 (ddd), 2.94(ddd), 2.62–2.45(m), 2.38–2.29(m), 2.20–2.11 (m), 2.00–1.88(m), 1.87–1.40(m), 1.39–1.08(m).

Compound 68

¹H NMR(500 MHz CDCl₃), (single diastereomer, mixture of rotomers) δ 8.61(d), 7.38(d), 7.31(s), 7.28–7.22(m), 7.14 (dd), 7.10(d), 7.04(d), 6.83(d), 5.23(dd), 5.14(dd), 5.36(d), 5.11(brs), 4.58(m), 4.31(m), 3.91(s), 3.90(s), 3.89(s), 3.88 (s), 3.82–3.79(m), 3.78–3.64(m), 3.51–3.44(m), 3.40(brd), 3.26–3.10(m), 2.63(dd), 2.32(brd), 2.00–1.92(m), 1.88–1.40 (m), 1.08–1.00(m).

Compound 69

¹H NMR(500 MHz CDCl₃), (mixture of diastereomers, mixture of rotomers) δ 8.60–8.57(m), 8.56–8.53(m), 7.38–7.35(m), 7.32–7.17(m), 6.53(s), 6.52(s), 5.83(q), 5.76 (q), 5.38–5.32(m), 5.17–5.05(m), 4.67–4.60(m), 4.30–4.28 (m), 4.13–4.08(m), 3.96–3.82(m), 3.80(s), 3.45(brd), 3.28 (ddd), 2.97(ddd), 2.77–2.72(m), 2.53–2.43(m), 2.36–2.22 (m), 2.15–1.92(m), 1.86–0.79(m).

Compound 70

¹H NMR(500 MHz CDCl₃), (mixture of diastereomers, mixture of rotomers) δ 8.59–8.43 (m), 7.38–6.98(m), 6.65 (s), 6.57(s), 6.53(m), 6.43(m), 5.88–5.84(m), 5.68–5.64(m), 5.63–5.59(m), 5.58–5.54(m), 5.35–5.28(m), 5.15–5.00(m), 4.99(d), 4.92(d), 4.58(d), 4.51(d), 4.33(d), 4.26(d), 3.89(s), 3.87(s), 3.83(s), 3.79(s), 3.72(s), 3.65(s), 3.45–3.37(m), 3.21 (ddd), 3.10(ddd), 2.95–2.83(m), 2.62–2.42(m), 2.28(d), 2.21 (d), 1.92–1.26(m), 1.17–1.12(m), 1.11–1.01(m).

Compound 71

¹H NMR(500 MHz CDCl₃), (single diastereomer, mixture of rotomers) δ 8.64(d), 7.35(d), 7.28(s), 6.60(d), 6.55(d), 6.52(t), 6.49(t), 5.86(q), 5.78(q), 5.42(d), 5.08(s), 4.64(bd), 4.35(m), 3.88–3.98(m), 3.46(bd), 3.21 (dt), 3.05 (dt), 2.36 (bd), 2.18(bd), 1.80(m), 1.74(bd), 1.64(s), 1.56 (d), 1.48–1.55 (m), 1.40 (d), 1.15–1.30(m).

Compound 72

¹H NMR(500 MHz CDCl₃), (single diastereomer, mixture of rotomers) δ 8.62(d), 7.35(d), 7.28(s), 6.60(d), 6.50(d), 6.45(t), 6.42(t), 5.85(q), 5.73(q), 5.40(d), 5.10(d), 5.04(d), 4.58(bd), 4.38(m), 3.92(s), 3.88(s), 3.82(s), 3.72(s), 3.50 (bd), 3.30(dt), 3.01(dt), 2.40(bd), 2.30(bd), 1.85(m), 1.64 (bs), 1.56(d), 1.48(d), 1.35–1.45(m).

Compound 73

¹H NMR (500 MHz CDCl₃), (mixture of diastereomers, mixture of rotomers) δ 8.55–8.65(brd), 7.32–7.42(brdd), 7.28(s), 7.20(s), 6.50–6.55(m), 5.72–5.87(m), 5.32–5.39(m), 5.05–5.17(m), 4.58–4.64(brd), 4.53–4.58(brd), 4.34–4.36 (brd), 4.25–4.29(brd), 3.71–3.96(ms), 3.40–3.48(m), 3.23–3.30(ddd), 3.13–3.22(ddd), 2.17–2.37(m), 1.10–1.86 (m), 1.48–1.52(d).

Compound 74

¹H NMR(500 MHz CDCl₃), (single diastereomer, mixture of rotomers) δ 8.62–8.58(d), 8.57–8.51(d), 7.38–7.35(d), 7.33–7.28(m), 7.27(s), 7.18(s), 6.61(s), 6.59(s), 5.65–5.60 (t), 5.55–5.50(t), 5.40–5.36(d), 5.18–5.05(m), 4.67–4.63 (brd), 4.33–4.30(d), 3.96(s), 3.93(s), 3.92(s), 3.87(s), 3.50–3.43(brd), 3.25–3.16(dt), 3.05–2.97(dt), 2.32–2.28 (brd), 2.14–2.08(brd), 1.95–1.85(m), 1.84–1.64 (m), 1.63–1.56(brd), 1.55–1.42(m), 1.35–1.23(m), 1.22–1.12(m), 0.92–0.83(t), 0.73–0.68(t).

Compound 75

¹H NMR(500 MHz CDCl₃), (single diastereomer, mixture of rotomers) δ 8.62–8.58(m), 8.57–8.53(d), 7.41–7.39(d), 7.38–7.35(d), 7.27(s), 7.23(s), 7.13(s), 6.61(s), 6.51(s), 5.60–5.55(t), 5.54(s), 5.50(t), 5.39–5.35(d), 5.15(s), 5.14–5.10(m), 5.09(s), 5.07(s), 5.01(s), 5.00(s), 4.60–4.55 (brd), 4.51–4.49(t), 4.40–4.38(brd), 3.90(s), 3.85(s), 3.80(s), 3.73(s), 3.48–3.43(brd), 3.30–3.22(dt), 2.95–2.88(dt), 2.38–2.32(brd), 2.27–2.22(brd), 1.90–1.70(m), 1.69–1.62 (brd), 1.59–1.50(m), 1.46–1.35(m), 1.26(s), 0.90–0.85(t), 0.82–0.78(t).

Compound 76

¹H NMR(500 MHz CDCl₃), (mixture of diastereomers, mixture of rotomers) δ 8.95(s), 8.80(d), 8.55(m), 8.50(m), 7.34(s), 7.30(s), 7.28(s), 6.76(s), 6.73(s), 5.85(q), 5.77(q), 5.40(m), 5.20–5.35(m), 4.60(m), 4.35(m), 3.85–3.98(m), 3.80(s), 3.48(bt), 3.18–3.30(m), 3.00(m), 2.40(bd), 2.32(bd), 2.26(bd), 1.65–1.90(m), 1.60(s), 1.55(dd), 1.48(d), 1.40(m), 1.12(m).

Compound 77

¹H NMR(500 MHz CDCl₃), (mixture of diastereomers, mixture of rotomers) δ 8.43–8.53(m), 7.20–7.56(m), 7.04(s), 7.01(s), 6.75–6.92(m), 6.62(brs), 5.78–5.85(m), 5.68–5.77 (m), 5.80–5.84(brd), 5.02–5.12(m), 3.76–4.00(m), 3.64–3.76(m), 3.49–3.60(m), 3.38–3.49(m), 3.32–3.34(d), 3.21–3.27(m), 3.02–3.18(m), 2.73–2.82(m), 2.37–2.53(m), 2.24–2.32(m), 2.20(s), 2.15(s), 1.27–1.72(m), 1.07–1.22(m), 0.92–0.97(dd), 0.82–0.86(dd).

Compound 78

¹H NMR(500 MHz CDCl₃), (single diastereomer, mixture of rotomers) δ 8.65–8.56(d), 8.55–8.51(d), 7.40–7.35(d), 7.34–7.20(m), 7.16(s), 6.70–6.60(m), 6.21–6.18(d), 6.15–6.11(d), 5.97–5.88(m), 5.83–5.75(m), 5.45–5.40(d), 5.32(s), 5.28(s), 5.27(s), 5.21–5.18(m), 5.13(s), 5.11(s), 4.67–4.61(brd), 4.51(d), 4.49(d), 4.35–4.33(d), 4.05–4.00 (m), 3.95(s), 3.94(s), 3.90(s), 3.84–3.82(d), 3.81(s), 3.66–3.60(q), 3.50–3.45(brd), 3.40(s), 3.30(s), 3.23–3.17 (dt), 3.03–2.97(brt), 3.86–3.80(brt), 2.60–2.55(brt), 2.50–2.40(m), 2.30–2.25(brd), 2.20(s), 2.15–2.10(brd), 1.90–1.65 (m), 1.64–1.60(brd), 1.56–1.43(m), 1.36–1.27(m), 1.26–1.11(m).

Compound 79

¹H NMR(500 MHz CDCl₃), (single diastereomer, mixture of rotomers) δ 8.65–8.59(d), 8.58–8.52(d), 7.40–7.35(d), 7.32–7.28(d), 7.25–7.24(d), 7.13(s), 6.65(s), 6.60(s), 6.20–6.18(d), 6.12–6.10(d), 5.97–5.90(m), 5.89–5.75(m), 5.43–5.38(d), 5.33–5.20(m), 5.16(s), 5.15(s), 5.10(s), 4.60–4.58(brd), 4.51–4.49(d), 4.40–4.38(d), 4.05–4.00(m), 3.93–3.85(m), 3.83(s), 3.82(s), 3.79(s), 3.65–3.60(q), 3.50–3.45(brd), 3.39(s), 3.30–3.18(m), 2.95–2.80(m), 2.61–2.55(m), 2.39–2.32(brd), 2.20(s), 1.90–1.75(m), 1.74–1.66(m), 1.65–1.60(m), 1.59–1.48(m), 1.47–1.31(m), 1.27–1.22(m), 1.20–1.18(d).

Compound 80

¹H NMR(500 MHz CDCl₃), (single diastereomer, mixture of rotomers) δ 8.62–8.58(d), 8.56–8.52(d), 7.40–7.35(d), 7.30(brs), 7.26(s), 7.18(s), 6.62(s), 6.60(s), 5.72–5.68(t), 5.62–5.58(t), 5.40–5.36(d), 5.30(s), 5.18(s), 5.17–5.13(d), 5.10(s), 4.66–4.61(br d), 4.60–4.58(m), 4.31–4.29(br d), 3.96(s), 3.95(s), 3.92(s), 3.87(s), 3.49–3.43(br d), 3.24–3.16 (dt), 3.04–2.96(brt), 2.32–2.28(br d), 2.17(s), 2.13–2.06(m), 2.91–2.85(m), 2.81–1.64(m), 1.63–1.55(m), 1.54–1.40(m), 1.36–1.00(m), 0.93–0.87(t), 0.83–0.77(t).

Compound 81

¹H NMR(500 MHz CDCl₃), (single diastereomer, mixture of rotomers) δ 8.62–8.58(d), 8.56–8.52(d), 7.41–7.39(d), 7.38–7.35(d), 7.33–7.28(d), 7.27(s), 7.23(s), 7.11(s), 6.60 (s), 6.50(s), 5.65(t), 5.61(t), 5.60–5.97(t), 5.38–5.35(d), 5.30 (s), 5.15(s), 5.13–5.10(d), 5.08(s), 5.06(s), 5.01(s), 4.59 (brd), 4.54(brd), 4.40–4.38(brd), 3.91(s), 3.85(s), 3.80(s), 3.74(s), 3.48–3.42(brd), 3.30–3.23(dt), 2.95–2.90(brt), 2.38–2.32(brd), 2.18(s), 1.90–1.75(m), 1.74–1.46(m), 1.44–1.10(m), 0.94–0.88(t), 0.87–0.82(t).

Compound 82

¹H NMR(500 MHz CDCl₃), (single diastereomer, mixture of rotomers) δ 7.28–7.35(m), 7.26(s), 7.24(m), 7.14(d), 7.10(d), 6.65(s), 6.57(s), 5.85(q), 5.78(q), 5.40(d), 5.13(s), 5.07(q), 5.04(s), 4.60(bd), 4.38(d), 3.92(s), 3.88(s), 3.80(s), 3.48(bd), 3.26 (dt), 2.95(dt), 2.40(bd), 2.25(bd), 1.82(m), 1.64(bd), 1.56(s), 1.54(d), 1.46(d), 1.38(m).

Compound 83

¹H NMR(500 MHz CDCl₃), (single diastereomer, mixture of rotomers) δ 7.36(s), 7.34(m), 7.27(m), 7.22(d), 7.13(dd), 7.08(dd), 6.65(s), 5.85(q), 5.75(q), 5.40(d), 5.10(d), 5.04(s), 4.63(bd), 4.34(d), 3.95(s), 3.92(s), 3.88(s), 3.46(bd), 3.22 (dt), 3.04(dt), 2.33(bd), 2.15(bd), 1.80(m), 1.70(dt), 1.55(d), 1.46–1.58(m), 1.36(d), 1.14(m).

Compound 84

¹H NMR(500 MHz CDCl₃), (single diastereomer, mixture of rotomers) δ 8.53 (d), 8.52(d), 7.42(d), 7.31(s), 7.27(d), 7.17(s), 6.52(ABq), 5.81(q), 5.74(q), 5.10(d), 5.04(s), 5.03 (s), 4.58–4.50(m), 4.31(m), 3.91(s), 3.88(s), 3.87 (s), 3.85 (s), 3.41(brd), 3.18(ddd), 3.00(ddd), 2.29(brd), 2.12(brd), 1.78–1.72(m), 1.68(brd), 1.52(d), 1.36(d), 1.32(d), 1.31(d), 1.11(m).

Compound 85

¹H NMR(500 MHz CDCl₃), (single diastereomer, mixture of rotomers) δ 8.51(d), 7.42(d), 7.31(s), 7.28(d), 7.25(s), 7.13(s), 6.58(s), 5.80(q), 5.76(q), 5.33(d), 5.10(s), 5.02(s), 4.56–4.50(m), 4.31(brd), 3.90(s), 3.88(s), 3.81(s), 3.79(s), 3.46 (brd), 3.24 (ddd), 2.90 (ddd), 2.33 (brd), 2.21 (brd), 1.85–1.74(m), 1.62(m), 1.51(d), 1.47(d), 1.31(d), 1.29(d).

Compound 86

¹H NMR(500 MHz CDCl₃), (single diastereomer, mixture of rotomers) δ 8.61–8.45(m), 7.38–7.28(m), 6.68(s), 6.49(s), 5.79(q), 5.61(q), 5.19–5.01(m), 4.72–4.63(m), 3.89–3.67 (m), 3.65–3.45(m), 2.85(t), 2.58(t), 2.39–2.23(m), 2.11–1.92 (m), 1.72–1.45(m), 1.39–1.16(m), 0.89(m).

Compound 87

¹H NMR(500 MHz CDCl₃), (single diastereomer, mixture of rotomers) δ 8.60–8.46(m), 7.38–7.15(m), 6.74–6.63(m), 6.62(s), 6.52–6.47(m), 5.75(q), 5.61(m), 5.32–5.25(m), 5.15–5.01(m), 4.72–4.59(m), 3.93–3.80(m), 3.75(m), 3.62–3.43(m), 2.39–1.55(m), 1.50(dd), 1.36–1.21(m).

Compound 88

¹H NMR (500 MHz CDCl₃), (mixture of diastereomers, mixture of rotomers) δ 9.16(d), 8.74(d), 8.70(d) 7.85(d), 7.50(t), 7.27(d), 6.68(s), 5.80(m), 5.70(m), 5.38(bd), 5.31 (bd), 5.24(s), 5.20(d), 4.60(m), 4.34(dd), 3.88–3.95(m), 3.84 (s), 3.75(s), 3.45(bd), 3.24(dt), 3.19(dt), 2.98(bt), 2.34(bd), 2.30(bd), 2.22(bd), 1.10–1.90(m), 1.52(d), 1.45(d).

Compound 89

¹H NMR(500 MHz CDCl₃), (single diastereomer, mixture of rotomers) δ 7.36–7.22(m), 5.43(d), 5.36(quintet), 5.25 (quintet), 4.60–4.35(m), 3.95(s), 3.91(s), 3.88(s), 3.03(d), 3.67(d), 3.47–3.40(brd), 3.24(dt), 3.07(dt), 2.38(br d), 2.22 (br d), 1.85–1.60(m), 1.58–1.25(m).

Compound 91

¹H NMR(500 MHz CDCl₃), (single diastereomer, mixture of rotomers) δ 9.01–8.93(m), 8.78(m), 8.06(m), 7.75(s), 7.68(t), 7.61(m), 7.57(d), 7.51–7.41(m), 7.28–7.19(m), 7.15 (t), 7.12–7.05(m), 7.03(s), 5.82(q), 5.73(t), 5.33(d), 4.55(d), 4.33(d), 3.93–3.78(m), 3.73(s), 3.43(d,br), 3.21(dt), 3.01(t), 2.63(t), 2.58(t), 2.39(d,br), 2.22(d), 2.09–1.94(m), 1.92–1.43 (m), 1.41–1.14(m).

Compound 92

¹H NMR(500 MHz CDCl₃), (single diastereomer, mixture of rotomers) δ 8.94(d), 8.81(m), 8.08(m), 7.75(s), 7.69(t), 7.55(d), 7.48(t), 7.42(m), 7.31(s), 7.29–7.07(m), 7.02(d), 5.81(t), 5.71(t), 5.40(d), 4.56(d), 4.34(d), 3.92–3.79(m), 3.40(d,br), 3.11(dr), 2.96(t), 2.61(t), 2.50(m), 2.22–1.91(m), 1.90–1.35(m), 1.20(s), 1.02(m), 0.83(t).

Compound 93

¹H NMR (500 MHz CDCl₃), (mixture of diastereomers, mixture of rotomers) δ 8.62–8.55(m), 7.66–7.58(m), 7.57–7.56(m), 7.52–7.46 (m), 7.40–7.30(m), 7.29–7.20(m), 7.19–7.04(m), 6.96–6.79(m), 6.77–6.69(m), 5.85–5.77(m), 5.70–5.62(m), 5.43–5.38(m), 5.10–4.98(m), 4.64–4.52(m), 4.39–4.35(m), 4.08–4.06(m), 4.02–3.99(m), 3.98–3.90(m), 3.89–3.84(m), 3.83–3.68(m), 3.48–3.40(m), 3.18(ddd), 3.14 (ddd), 2.96(ddd), 2.92(ddd), 2.68–2.58(m), 2.57–2.51(m), 2.37(dd), 2.24–2.11(m), 2.05–1.94(m), 1.89–1.41(m), 1.40–1.23(m), 1.22–1.10(m).

Compound 94

¹H NMR(500 MHz CDCl₃), (mixture of diastereomers, mixture of rotomers) δ 8.61–8.55(m), 7.47–7.40(m), 7.38–7.02(m), 6.92–6.88(m), 6.87–6.82(m), 6.81–6.71(m), 6.68–6.64(m), 5.77–5.72(m), 5.65–5.59(m), 5.40–5.36(m), 5.11–5.04(m), 5.02(s), 4.97(s), 4.58(m), 4.52(m), 4.36–4.33

(m), 3.87(s), 3.83(s), 3.77(s), 3.70(s), 3.57–3.52(m), 3.48–3.36(m), 3.24(ddd), 3.12(ddd), 2.99(ddd), 2.81(ddd), 2.66–2.53(m), 2.41–2.31(m), 2.28–2.22(m), 2.02–1.92(m), 1.88–1.45(m), 1.44–1.21(m).

Compound 95

$^1$H NMR(500 MHz CDCl$_3$), (mixture of diastereomers, mixture of rotomers) δ 8.91–8.75(m), 7.38–7.29(m), 7.28–7.02(m), 6.92–6.80(m), 6.79–6.76(m), 6.74–6.71(m), 6.69–6.64(m), 6.09–5.98 (m), 5.78–5.70(m), 5.65–5.60(m), 5.40–5.34(m), 5.32–5.26(m), 5.19–5.13(m), 5.09–5.00(m), 4.63–4.52(m), 4.36–4.32(m), 3.95–3.63(m), 3.46(brd), 3.41 (brd), 3.24(ddd), 3.12(ddd), 3.02–2.92(m), 2.67–2.45(m), 2.41–2.30(m), 2.27–2.21(m), 2.20–2.12(m), 2.01–1.90(m), 1.89–1.04(m).

Compound 96

$^1$H NMR(500 MHz CDCl$_3$), (mixture of diastereomers, mixture of rotomers) δ 8.59–8.54(m), 7.67–7.57(m), 7.55–7.49(m), 7.47–7.38(m), 7.37–7.05(m), 6.95–6.71(m), 5.83(t), 5.78(t), 5.68(t), 5.65(t), 5.42(m), 5.28(s), 5.23–4.95 (m), 4.62–4.52(m), 4.38(m), 3.93(s), 3.92(s), 3.88(s), 3.87 (s), 3.47(m), 3.18–3.07(m), 2.98–2.87(m), 2.67–2.58(m), 2.57–2.50(m), 2.41–2.30(m), 2.22–2.17(m), 2.16–2.11(m), 2.03–1.92(m), 1.89–1.21(m), 1.20–1.09(m). Compound 97

$^1$H NMR(500 MHz CDCl$_3$), (mixture of diastereomers, mixture of rotomers) δ 8.62–8.52(m), 7.64–7.54(m), 7.52–7.46(m), 7.42–7.04(m), 6.97–6.78(m), 6.77–6.70(m), 6.12–5.97(m), 5.85–5.76(m), 5.69–5.61(m), 5.46–5.35(m), 5.33–5.24(m), 5.10–5.01(m), 4.70–4.52(m), 4.39–4.33(m), 3.92(s), 3.91(s), 3.88(s), 3.87 (s), 3.48–3.41(m), 3.18–3.10 (m), 2.97–.2.90(m), 2.67–2.57(m), 2.56–2.50(m), 2.42–2.31 (m), 2.23–2.10(m), 2.04–1.93(m), 1.89–1.10(m).

Compound 98

$^1$H NMR (500 MHz CDCl$_3$), (mixture of diastereomers, mixture of rotomers) δ 8.59–8.53(m), 7.67–7.44(m), 7.39–7.03(m), 6.94–6.78(m), 6.77–6.66(m), 6.46–6.33(m), 6.03–5.93(m), 5.83(t), 5.78(t), 5.68(t), 5.46(t), 5.42–5.37 (m), 5.08–4.97(m), 4.92–4.66 (m), 4.64–4.52(m), 4.40–4.33 (m), 3.94(s), 3.92(s), 3.90(s), 3.88(s), 3.87–3.84(m), 3.48–3.40(m), 3.20–3.08(m), 2.98–2.88(m), 2.64–2.57(m), 2.56–2.50(m), 2.41–2.31(m), 2.23–2.17(m), 2.16–2.10(m), 2.03–1.92(m), 1.88–1.08(m).

Compound 99

$^1$H NMR(500 MHz CDCl$_3$), (mixture of diastereomers, mixture of rotomers) δ 8.67–8.58(m), 8.54–8.48(m), 7.49–7.03(m), 6.95–6.87(m), 6.86–6.82(m), 6.72–6.68(m), 5.78–5.68(m), 5.63–5.57(m), 5.40–5.31(m), 5.14–4.93(m), 4.59–4.51(m), 4.35–4.30(m), 3.90–3.78(m), 3.73(s), 3.71(s), 3.45(brd), 3.38(brd), 3.22(ddd), 3.11(ddd), 2.99–2.91(m), 2.67–2.48(m), 2.42–2.39(m), 2.26–2.18(m), 2.17–2.11(m), 2.05–1.92(m), 1.89–1.18(m), 1.09–0.98(m).

Compound 100

$^1$H NMR(500 MHz CDCl$_3$), (mixture of diastereomers, mixture of rotomers) δ 8.63–8.56(m), 7.68–7.59(m), 7.57–7.40(m), 7.39–7.20(m), 7.19–7.04(m), 7.03–6.98(m), 6.97–6.81(m), 6.78–6.71(m), 5.80(s), 5.77(s), 5.67(t), 5.62 (t), 5.40–5.34(m), 5.27–4.94(m), 4.62–4.52(m), 4.38–4.32 (m), 3.94(s), 3.92(s), 3.91(s), 3.88(s), 3.87(s), 3.82(s), 3.81 (s), 3.47–3.37(m), 3.18–3.05(m), 3.00–2.90(m), 2.68–2.50 (m), 2.43–2.29(m), 2.22–2.09(m), 2.07–1.95(m), 1.90–1.63 (m), 1.62–1.20(m), 1.14–1.02(m).

Compound 101

$^1$H NMR(500 MHz CDCl$_3$), (mixture of diastereomers, mixture of rotomers) δ 8.64–8.58(m), 7.43–7.30(m), 7.29–7.19(m), 7.18–7.02(m), 6.98–6.94(m), 6.93–6.87(m), 6.86–6.83(m), 6.77–6.73(m), 5.73(t), 5.71(t), 5.62(t), 5.60 (t), 5.41–5.32(m), 5.10–5.05(m), 4.58–4.52(m), 4.35–4.30 (m), 3.94(s), 3.93(s), 3.91(s), 3.90(s), 3.88(s), 3.84(s), 3.83 (s), 3.78(s), 3.76(s), 3.45(brd), 3.38(brd), 3.22(ddd), 3.10 (ddd), 3.06–2.92(m), 2.67–2.53(m), 2.52–2.48(m), 2.42–2.29(m), 2.28–2.11(m), 2.04–1.94(m), 1.88–1.20(m), 1.08–0.98(m).

Compound 102

$^1$H NMR(500 MHz CDCl$_3$), (mixture of diastereomers, mixture of rotomers) δ 8.63–8.57 (m), 7.66–7.60 (m), 7.58–7.54(m), 7.53–7.47(m), 7.41–7.31(m), 7.27–7.20(m), 7.19–7.03(m), 6.92–6.70(m), 5.80(t), 5.77(t), 5.67(t), 5.61 (t), 5.40–5.36(m), 5.09–5.02(m), 4.70–4.52(m), 4.37–4.33 (m), 3.92(s), 3.91(s), 3.89(s), 3.88(s), 3.87(s), 3.86(s), 3.85 (s), 3.82–3.77(m), 3.48(s) 3.40(m), 3.18–3.09(m), 2.98–2.88 (m), 2.66–2.42(m), 2.40–2.10(m), 2.04–1.94(m), 1.89–1.62 (m), 1.61–1.18(m), 1.14–1.13(m).

Compound 103

$^1$H NMR(500 MHz CDCl$_3$), (mixture of diastereomers, mixture of rotomers) δ 7.76–7.59(m), 7.50–7.40(m), 7.38–7.18(m), 7.17–7.05(m), 6.93–6.87(m), 6.77–6.73(m), 6.18–6.15(m), 5.85(t), 5.79(t), 5.20(t), 5.16(t), 5.41–5.38 (m), 5.21–5.08(m), 4.60–4.52(m), 4.37–4.32(m), 3.92(s), 3.91(s), 3.88(s), 3.87(s), 3.47–3.37(m), 3.17–3.03(m), 2.97–2.91(m), 2.64–2.58(m), 2.57–2.50(m), 2.42–2.33(m), 2.05–1.95(m), 1.90–1.80(m), 1.79–1.62(m), 1.61–1.31(m), 1.13–1.08(m).

Compound 104

$^1$H NMR(500 MHz CDCl$_3$), (mixture of diastereomers, mixture of rotomers) δ 7.47–7.41(m), 7.37–7.02(m), 5.78–5.72(m), 5.18(t), 5.12(t), 5.40–5.37(m), 5.10(s), 5.08 (s), 5.07(s), 5.05(s), 4.59–4.51(m), 4.37–4.31(m), 3.87(s), 3.85(s), 3.77(s), 3.73(s), 3.45(brd), 3.37(brd), 3.24(ddd), 3.10(ddd), 3.02–2.94(m), 2.65–2.59(m), 2.58–2.53(m), 2.52–2.46(m), 2.43–2.35(m), 2.27–2.22(m), 2.21–2.15(m), 2.05–1.94(m), 1.89–1.30(m), 1.10–1.01(m).

Compound 105

$^1$H NMR(500 MHz CDCl$_3$), (mixture of diastereomers, mixture of rotomers) δ 8.39(d), 7.64(q), 7.52(q), 7.43(m), 7.29–7.03(m), 5.02–4.88(m), 4.60(q), 4.46(q), 3.62(m), 3.52–3.38(m), 2.68–2.49(m), 2.31–2.13(m), 2.09–1.75(m), 1.74–1.44(m), 1.29–1.16(m).

Compound 106

$^1$H NMR(500 MHz CDCl$_3$), (single diastereomer, mixture of rotomers) δ 8.43–8.34 (m), 7.46(ddt), 7.39(ddt), 7.32(s), 7.19–7.15(m), 5.32(br d), 5.28(s), 5.04–4.98(m), 4.92–4.88 (m), 4.85(br d), 3.92(s), 3.90(s), 3.88(s), 3.87(s), 3.45(br d), 3.23(dt), 3.05(dt), 2.64–2.02(m), 2.29(br d), 2.13(br d), 1.82–1.48(m).

Compound 107

$^1$H NMR(500 MHz CDCl$_3$), (single diastereomer, mixture of rotomers) δ 7.34–7.23(m), 5.31(quintet), 5.12(quintet), 4.74(dd), 4.69(dd), 4.52(dq), 4.41(dq), 3.93(s), 3.90(s), 3.82 (s), 3.70(m), 3.56–3.43(m), 2.34–1.88(m).

Compound 108

$^1$H NMR(500 MHz CDCl$_3$), (single diastereomer, mixture of rotomers) δ 8.50–8.31(m), 7.62(d), 7.57(d), 7.46(d), 7.44–7.31(m), 7.30(s), 7.19(q), 7.10(q), 5.00(m), 4.80(m), 4.69(m), 4.56(m), 3.97–3.71(m), 3.61–3.43(m), 2.68–2.41 (m), 2.34–2.12(m), 2.08–1.84(m), 1.83–1.72(m), 1.71–1.42 (m), 1.29–1.13(m).

Compound 109

$^1$H NMR(500 MHz CDCl$_3$), (single diastereomer, mixture of rotomers) δ 8.48–8.32(m), 7.53(dd), 7.47(m), 7.25–7.14 (m), 5.02–4.89(m), 4.79(m), 4.49(m), 3.73–3.55(m), 3.48

(quintet), 3.30(quintet), 2.69–2.44(m), 2.32–1.41(m), 1.32–1.04(m), 1.01(m).

Compound 110

$^1$H NMR(500 MHz CDCl$_3$), (single diastereomer, mixture of rotomers) δ 8.63–8.51(m), 8.50–8.31(m), 8.06(m), 7.93–7.85(m), 7.84–7.76(m), 7.69(d), 7.51–7.40(m), 7.23–7.11(m), 7.09(t), 5.32(d), 5.20(m), 5.08(m), 4.95(m), 4.61–4.52(m), 3.80(m), 3.61(m), 3.39(t), 3.21(dt), 2.94(dt), 2.74–2.44(m), 2.40(d), 2.31(m), 2.22–2.14(m), 2.13–1.91 (m), 1.90–1.13(m).

Compound 110

$^1$H NMR(500 MHz CDCl$_3$), (single diastereomer, mixture of rotomers) δ 8.46–8.36(m), 7.61(dd), 7.52(dd), 7.50–7.40 (m), 7.22–7.15(m), 6.87(dd), 6.83(dd), 6.07(s), 6.04(dd), 5.35(d), 5.10–5.06(m), 4.98–4.92(m), 4.6(br d), 4.34 (d), 3.4(br d), 3.15(dr), 2.98(dt), 2.68–2.50(m), 2.24 (br d), 1.8–1.46(m), 1.37–1.24(m).

Compound 112

$^1$H NMR(500 MHz CDCl$_3$), (single diastereomer, mixture of rotomers) δ 8.7(d), 8.6(d), 7.7.–7.6(dd), 7.45(s), 7.3–7.2 (m), 6.9(d), 6.1(d), 5.3(m), 4.6(d), 4.4(d), 3.45(dd), 3.4–3.3 (m), 3.1–2.9(m), 2.85–2.8(m), 2.4(dd), 1.97–1.7(m), 1.6–1.35(m).

Compound 113

$^1$H NMR(500 MHz CDCl$_3$), (single diastereomer, mixture of rotomers) δ 8.7(d), 8.6(d), 8.5(m), 7.7–7.6(dd), 7.3(s), 7.2(m), 5.4(d), 5.3(m), 4.6(brd), 4.4(brd), 3.95(s), 3.90(s), 3.85(s), 3.45(dd), 3.3–3.2(dd), 3.1–2.9(m), 2.4(dd), 1.95(s), 1.9–1.7(m), 1.6–1.35(m).

Compound 114

$^1$H NMR(500 MHz CDCl$_3$), (single diastereomer, mixture of rotomers) δ 8.49(d), 7.52(q), 7.31(s), 7.18(s), 7.12–6.99 (m), 5.31(d), 4.99(m), 4.54(d), 3.92–3.79(m), 3.42(d,br), 3.22(dt), 3.02(dt), 2.81–2.62(m), 2.60(t), 2.30(d,br), 2.13(d), 1.82–1.19(m).

Compound 115

$^1$H NMR(50 0MHz CDCl$_3$), (single diastereomer, mixture of rotomers) δ 8.63–8.53(m), 7.43–7.37(d), 7.35–7.23(m), 7.17(s), 6.56(s), 6.54(s), 5.48–5.42(d), 5.41–5.38(d), 5.32–5.29(d), 5.20–5.10(m), 4.68–4.62(brd), 4.32–4.30(d), 4.00–3.90(m), 3.86(s), 3.53–3.47(brd), 3.25–3.20(dt), 3.05–3.00(dt), 2.37–2.21(brd), 2.10–2.00(m), 1.92–1.87(m), 1.80–1.70(m), 1.69–1.59(m), 1.57–1.43(m), 1.34–1.15(m), 0.97–0.92(d), 0.85–0.78(d), 0.77–0.75(d), 0.66–0.64(d).

Compound 116

$^1$H NMR(500 MHz CDCl$_3$), (single diastereomer, mixture of rotomers) δ 8.65–8.55(m), 7.42–7.40(d), 7.39–7.37(d), 7.33–7.30(d), 7.26(s), 7.22(s), 7.10(s), 6.60(s), 6.42(s), 5.42–5.40(d), 5.39–5.37(d), 5.34–5.32(d), 5.16(s), 5.15–5.11(m), 5.10(s), 5.07–4.94(q), 4.60–4.55(brd), 4.41–4.39(brd), 3.93(s), 3.84(s), 3.80(s), 3.70(s), 3.48–3.43 (brd), 3.30–3.22(dt), 2.96–2.90(dt), 2.39–2.35(brd), 2.29–2.25(brd), 2.05–2.00(m), 1.90–1.75(m), 1.65–1.60(m), 1.59–1.48(m), 1.47–1.33(m), 0.95–0.87(d), 0.86–0.83(d), 0.82–0.78(d), 0.73–0.69(d).

Compound 117

$^1$H NMR(500 MHz CDCl$_3$), (single diastereomer, mixture of rotomers) δ 8.65–8.60(d), 8.59–8.52(d), 7.45–7.39(d), 7.38–7.23(m), 7.21(s), 6.67(s), 6.66(s), 5.83–5.79(t), 5.78–5.75(t), 5.74–5.63(m), 5.53–5.48(m), 5.45–5.41(brd), 5.20–5.05(m), 5.04(s), 5.01(s), 4.99(s), 4.72–4.68(brd), 4.35–4.32(brd), 3.98(s), 3.97(s), 3.93(s), 3.90(s), 3.85(s), 3.55–3.48(brd), 3.32–3.24(dt), 3.10–3.03(dt), 2.70–2.62(m), 2.61–2.56(m), 2.55–2.45(m), 2.39–2.32(brd), 2.20–2.15 (brd), 1.97–1.70(m), 1.69–1.60(m), 1.59–1.47(m), 1.40–1.20(m), 0.93–0.90(m).

Compound 118

$^1$H NMR(500 MHz CDCl$_3$), (single diastereomer, mixture of rotomers) δ 8.66–8.62(d), 8.61–8.59(d), 7.46–7.44(d), 7.43–7.40(d), 7.39–7.33(d), 7.31(s), 7.28(s), 7.16(s), 6.68 (s), 6.57(s), 5.80–5.75(t), 5.74–5.67(m), 5.43–5.40(d), 5.20–5.05(m), 4.64–4.60(brd), 4.43–4.41(brd), 3.96(s), 3.90 (s), 3.85(s), 3.78(s), 3.53–3.49(brd), 3.35–3.28(dt), 3.02–2.96(brt), 2.70–2.50(m), 2.42–2.36(brd), 2.32–2.29 (brd), 1.91–1.78(m), 1.73–1.68(brd), 1.63–1.55(m), 1.50–1.40(m).

Example 13—MDR SENSITIZATION ASSAYS

To assay the ability of the compounds according to this invention to increase the antiproliferative activity of a drug, cell lines which are known to be resistant to a particular drug may be used. These cell lines include, but are not limited to, the L1210, P388D, CHO and MCF7 cell lines. Alternatively, resistant cell lines may be developed. The cell line is exposed to the drug to which it is resistant, or to the test compound; cell viability is then measured and compared to the viability of cells which are exposed to the drug in the presence of the test compound.

We have carried out assays using L1210 mouse leukemia cells transformed with the pHaMDR1/A retrovirus carrying a MDR1 cDNA, as described by Pastan et al., *Proc. Natl. Acad. Sci.*, Vol. 85, 4486–4490. (1988). The resistant line, labelled L1210VMDRC.06, was obtained from Dr. M. M. Gottesman of the National Cancer Institute. These drug-resistant transfectants had been selected by culturing cells in 0.06 mg/ml colchicine.

Multi-drug resistance assays were conducted by plating cells (2×10$^3$, 1×10$^4$, or 5×10$^4$ cells/well) in 96 well microtiter plates and exposing them to a concentration range of doxorubicin (50 nM-10 NM) in the presence or absence of multi-drug resistance modifier compounds ("MDR inhibitors") of this invention (1, 2.5 or 10 μM) as described in Ford et al., *Cancer Res.*, Vol. 50, 1748–1756. (1990). After culture for 3 days, the viability of cells was quantitated using MTT (Mossman) or XTT dyes to assess mitochondrial function. All determinations were made in replicates of 4 or 8. Also see, Mossman T., *J. Immunol. Methods*, Vol. 65, 55–63 (1983).

Results were determined by comparison of the IC$_{50}$ for doxorubicin alone to the IC$_{50}$ for doxorubicin+MDR inhibitor. An MDR ratio was calculated (IC$_{50}$ Dox/IC$_{50}$ Dox+ Inhibitor) and the integer value used for comparison of compound potencies.

In all assays, compounds according to this invention were tested for intrinsic antiproliferative or cytotoxic activity. The results are summarized in Table 2 below. As demonstrated in Table 2, the compounds generally caused <10% cytotoxicity at concentrations of 10 μM or greater.

Compounds of formula (I) have also been assayed for MDR sensitization activity with other MDR cell lines including several human cell lines (e.g., myeloma cells (8226/DOX6, 8226/DOX40, MDR10V, MR 20), melanoma cells (VCR 4.5, VBL 3.0, COL-1), GM3639 T cells, MCF-7 breast carcinoma, A549 bronchogenic adenocarcinoma, LOX melanoma, P388/ADR, and P388 VMDRC.04), and different chemotherapeutic drugs (e.g., doxorubicin, vincristine, vinblastine, taxol, colchicine, and etoposide). Results similar to those shown in Table 2 were obtained in these assays (data not shown), further demonstrating the effectiveness of the compounds of this invention in multi-drug resistance sensitization.

TABLE 2

Evaluation of Compounds for Reversal of Multidrug Resistance

| Cmpd | IC$_{50}$ Dox Alone | IC$_{50}$ Dox + 1 µM | IC$_{50}$ Dox + 2.5 µM | IC$_{50}$ Dox + 10 µM | MDR Ratio 1 µM | MDR Ratio 2.5 µM | MDR Ratio 10 µM |
|---|---|---|---|---|---|---|---|
| 2 | 900 nM | 400 | | <60 | 2.25 | | >15 |
| 4 | 800 | 400 | | <60 | 2 | | 2.7 |
| 6 | 900 | 300 | | <60 | 3 | | >15 |
| 8 | 800 | 500 | | 100 | 1.6 | | 8 |
| 10 | 6500 | | 625 | | | 10.4 | |
| 11 | 700 | 200 | | <60 | 3.5 | | >12 |
| 12 | 6500 | | 350 | | | 18.6 | |
| 15 | 800 | 400 | | 90 | 1.4 | | 11.1 |
| 21 | 1000 | 700 | | 90 | 1.4 | | 11.1 |
| 27 | 1200 | 900 | | 200 | 1.3 | | 6 |
| 31 | 1300 | 900 | | 500 | 1.4 | | 2.6 |
| 43 | 6500 | | 600 | | | 10.8 | |
| 44 | 400 | 200 | | <60 | 2 | | >6 |
| 47 | 900 | 800 | | 100 | 1.1 | | 9 |
| 48 | 1400 | 800 | | 100 | 1.75 | | 14 |
| 49 | 5000 | | 700 | | | 7.1 | |
| 52 | 900 | 500 | | <60 | 1.8 | | >15 |
| 53 | 1600 | 700 | | 200 | 2.3 | | 8 |
| 54 | 6500 | | 510 | | | 12.7 | |
| 55 | 900 | 400 | | <60 | 1.3 | | >7 |
| 56 | 400 | 300 | | <60 | 1.3 | | >7 |
| 64 | 1500 | 700 | | 400 | 2.1 | | 3.75 |
| 66 | 1600 | 1300 | | 400 | 1.3 | | 4 |
| 69 | 800 | 400 | | <60 | 2 | | >13 |
| 84 | 6000 | | 350 | | | 17.1 | |
| 98 | 6000 | | 2000 | | | 3 | |
| 105 | 9000 | 2800 | | 500 | 3.2 | | 18 |
| CsA | 1800 | 80 | | | 22.5 | | |
| FK506 | 400 | 400 | | 100 | 1 | | 4 |

Example 14—Immunosuppression (Mitogenesis) Assays Cell Source and Culture

Fresh peripheral blood lymphocytes (PBLs) from Leuko-Pak cells or whole blood from random normal blood donors (tested HIV-negative and hepatitis negative) were isolated and separated by density centrifugation over Histopaque 1077 (Sigma Chemical Co., St. Louis, Mo.). The murine CTLL cytotoxic T cell line and the human Jurkat T cell line were from ATCC (CTLL-2 ATCC TIB214, JURKAT CLONE E6-1 ATCC TIB152). The human allogeneic B cell lines used for activation of the fresh PBLs were EBV-transformed lymphocytes from normal healthy adult donors with two completely different HLA haplotypes. All cell lines were routinely tested for the presence of Mycoplasma contamination using the Gibco Mycotect test kit and found to be Mycoplasma-free. Culture medium consisted of RPMI 1640 (Gibco, Grand Island, N.Y.) containing penicillin (50 U/ml) and streptomycin (50 µg/ml), L-glutamine 2 mM, 2 mercaptoethanol ($5 \times 10^{-5}$), 10% heat-inactivated FCS and 10 mM HEPES.

Compound Solutions and Titrations

All chemical stocks were dissolved in DMSO. Titrations of compounds were made into the medium the individual assay was carried out in, i.e., complete RPMI or HB 104 for final diluted concentrations, using multiple three-fold dilutions from 1 µM or 10 µM stock solutions.

Mitogenesis Assays ("PMA" and "OKT3")

The inhibitory effect of test compounds on the proliferation of human PBLs in response to mitogens (Waithe, W. K. and K. Hirschhorn, *Handbook of Experimental Immunology*, 3d Ed. Blackwell Scientific Publications, Oxford (1978); Mishell, B. B. and S. M. Shiigi, *Selected Methods in Cellular Immunology* W. H. Freeman and Co., San Francisco, Calif. (1980)) was assessed by stimulation of $5 \times 10^4$ cells with OKT3 ($10^{-4}$ dilution final) or PMA (10 ng/ml) plus ionomycin (250 ng/ml) in the presence or absence of different concentrations of test compounds and control drugs (CsA, FK506, rapamycin) in final volume of 200 µl per well in 96 well round bottomed plates. After 48 h incubation (37° C., 5% $CO_2$), cells were pulsed with 1 µCi of $^3$H-Leucine, harvested 24 h later with a Tom Tek cell harvester, and counted in LKB β-scintillation counter. Results (cpm) were compared with controls with medium alone, and concentrations causing 50% reduction in counts (IC$_{50}$) were calculated. The results are summarized in Table 3 below.

TABLE 3

PMA and OKT3 - Induced Proliferation Assay

| Cmpd. | PMA (µM) | OKT3 (µM) |
|---|---|---|
| 3 | >10 | 17.5 |
| 4 | >10 | >17.5 |
| 5 | >17.5 | >17.5 |
| 6 | 7.5 | >17.5 |
| 7 | >17.5 | >17.5 |
| 8 | 14.6 | 17.5 |
| 9 | 5.6 | 6.0 |
| 10 | >7.6 | >17.5 |
| 11 | >7.6 | >17.5 |
| 12 | 8.2 | 17.5 |
| 13 | 9.3 | 15.0 |
| 14 | >8.3 | >15 |
| 15 | 6.7 | 9.0 |
| 16 | 9.0 | >15.0 |
| 17 | >15.0 | >15.0 |
| 18 | 6.3 | >9.0 |
| 19 | 7.8 | 9.8 |
| 20 | 5.5 | >9.0 |
| 21 | >9.0 | 12.6 |
| 22 | 10.0 | 4.6 |
| 23 | 8.0 | 4.0 |
| 25 | 8.7 | 3.8 |
| 26 | >17.0 | >12.5 |
| 27 | 10.0 | 37.5 |
| 28 | >8.7 | >8.7 |
| 29 | >50.0 | >50.0 |
| 30 | >20.0 | >23.3 |
| 31 | 7.5 | 15.0 |
| 32 | >10.0 | >30.0 |
| 33 | >9.0 | >10.0 |
| 34 | 50.0 | 50.0 |
| 35 | 6.5 | 9.5 |
| 36 | 33.0 | 40.0 |
| 37 | 5.0 | 6.0 |
| 40 | 10.0 | 50.0 |
| 41 | 20.0 | >50.0 |
| 44 | 10.0 | 10.0 |
| 45 | 10.0 | 10.0 |
| 47 | >10.0 | >10.0 |
| 56 | >10.0 | >10.0 |
| 57 | 6.0 | 7.0 |
| 62 | 10.0 | 9.0 |
| 64 | 7.5 | 9.5 |
| 65 | 6.0 | 10.0 |
| 67 | 5.0 | 5.0 |
| 68 | 5.0 | 2.2 |
| 69 | 10.0 | 3.0 |
| 70 | 2.5 | 2.5 |
| 71 | 10.0 | 3.5 |
| 72 | 8.2 | 3.2 |
| 73 | 2.7 | 2.0 |
| 74 | 7.5 | >10.0 |
| 75 | >10.0 | 7.0 |
| 76 | 10.0 | 1.0 |
| 77 | 6.5 | 6.0 |
| 78 | 10.0 | 9.0 |
| 79 | 10.0 | 2.5 |
| 80 | 4.0 | 1.9 |

TABLE 3-continued

PMA and OKT3 - Induced Proliferation Assay

| Cmpd. | PMA (μM) | OKT3 (μM) |
|---|---|---|
| 81 | 9.0 | NT |
| 84 | 7.0 | 3.2 |
| 85 | 10.0 | 5.0 |
| 88 | >10.0 | >6.5 |
| 91 | 7.0 | 10.0 |
| 92 | 7.0 | 4.5 |
| 93 | 7.0 | 7.0 |
| 94 | >10.0 | >10.0 |
| 95 | >10.0 | >10.0 |
| 96 | >10.0 | >10.0 |
| 97 | 9.0 | 9.0 |
| 98 | >10.0 | >10.0 |
| 99 | >10.0 | >10.0 |
| 100 | >10.0 | >10.0 |
| 101 | 4.0 | 1.0 |
| 102 | 2.5 | 9.5 |
| 105 | >9.0 | >12.6 |
| 115 | 5.0 | 5.0 |
| 116 | >10.0 | 5.0 |
| 117 | 8.5 | 7.0 |
| 118 | 7.3 | 3.3 |

NT = Not Tested

The above results demonstrate the efficacy of the compounds of this invention against mitogen-induced proliferation, and as immunosuppressive agents.

EXAMPLE 14

Inhibition of MRP-Mediated MDR

In order to demonstrate that the compounds of this invention are effective in reversing MPR-mediated MDR, in addition to P-glycoprotein-mediated MDR, we assayed inhibition in a non-P-glycoprotein expressing cell line.

We plated HL60/ADR cells in 96 well microtiter plates ($4\times10^4$ cells/well). The cells were then exposed to various concentrations of doxorubicin (50 nM to 10 μM) in the presence or absence of various compounds of this invention at various concentrations (0.5–10 μM). After culturing the cells for 3 days, their viability was quantitated using the XTT dye method to assess mitochondrial function. Results were expressed as a ratio of the $IC_{50}$ for doxorubicin alone to the the $IC_{50}$ for doxorubicin plus MDR inhibitor. $IC_{50}$ values are expressed in nM. In all assays the intrinsic antiproliferative or cytotoxicity activity of the MDR inhibitors was also determined for HL60/ADR cells. The results of this assay are set forth in Table 4 below:

invention is to be defined by the appended claims, rather than by the specific embodiments which have been presented by way of example.

We claim:

1. A compound of formula (I):

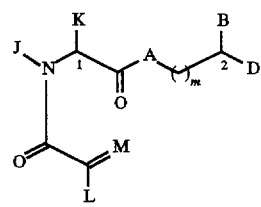

wherein

A is O, NH, or N—(C1–C4 alkyl);

B and D are independently:

(i) Ar, (C5–C7)-cycloalkyl substituted (C1–C6)-straight or branched alkyl or (C2–C6)-straight or branched alkenyl, (C5–C7)-cycloalkenyl substituted (C1–C6)-straight or branched alkyl or (C2–C6)-straight or branched alkenyl, or Ar-substituted (C1–C6)-straight or branched alkyl or Ar-substituted (C2–C6)-straight or branched alkenyl;

wherein in each case, any one of the $CH_2$ groups in said alkyl or alkenyl chains may be optionally replaced by a heteroatom selected from the group consisting of O, S, SO, $SO_2$; or (ii) 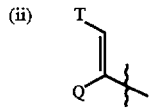

wherein Q is hydrogen, (C1–C6)-straight or branched alkyl or (C2–C6)-straight or branched alkenyl;

wherein T is Ar or substituted 5–7 membered cycloalkyl with substituents at positions 3 and 4 which are independently selected from the group consisting of hydrogen, oxo, hydroxyl, O—(C1–C4-alkyl) and O—(C2–C4alkenyl);

wherein Ar is a carbocyclic aromatic group selected from the group consisting of phenyl, 1-naphthyl, 2-naphthyl, indenyl, azulenyl, fluorenyl, and anthracenyl; or a heterocyclic aromatic group selected from the group consisting of 2-furyl, 3-furyl, 2-thienyl, 3-thienyl, 2-pyridyl, 3-pyridyl, 4-pyridyl,

TABLE 4

Reversal Of MRP-meidated MDR in HL60/ADR Cells

| Cmpd | $IC_{50}$Dox alone | $IC_{50}$Dox + 0.5 μM Cpd | $IC_{50}$Dox + 1 μM Cpd | $IC_{50}$Dox + 2.5 μM Cpd | $IC_{50}$Dox + 5 μM Cpd | $IC_{50}$Dox + 10 μM Cpd | MDR Ratio 0.5 μM | MDR Ratio 1 μM | MDR Ratio 2.5 μM | MDR Ratio 5 μM | MDR Ratio 10 μM |
|---|---|---|---|---|---|---|---|---|---|---|---|
| 9 | 5.0 | 3.75 | 2.5 | 1.3 | 0.6 | 0.4 | 1.3 | 2 | 3.8 | 8.3 | 12.5 |
| 12 | 5.0 | 4.75 | 4.3 | 3.5 | 3 | 3 | 1.1 | 1.2 | 1.4 | 1.7 | 1.7 |
| 106 | 5.0 | 3.0 | 1.75 | 0.6 | 0.24 | 0.1 | 1.7 | 2.9 | 8.3 | 21 | 50 |

While we have described a number of embodiments of this invention, it is apparent that our basic constructions may be altered to provide other embodiments which utilize the products, processes and methods of this invention. Therefore, it will be appreciated that the scope of this pyrrolyl, oxazolyl, thiazolyl, imidazolyl, pyrazolyl, 2-pyrazolinyl, pyrazolidinyl, isoxazolyl, isothiazolyl, 1,2,3-oxadiazolyl, 1,2, 3-triazolyl, 1,3,4-thiadiazolyl, pyridazinyl, pyrimidinyl, pyrazinyl, 1,3,5-triazinyl, 1,3,5- trithianyl, indolizinyl, indolyl, isoindolyl, 3-H-indolyl, indolinyl, benzo[b]furanyl, benzo[b]thiophenyl, 1H-indazolyl, benzimidazolyl, benzthiazolyl, purinyl, 4H-quinolizinyl, quinolinyl, isoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl, and phenoxazinyl;

wherein Ar may contain one to three substituents which are independently selected from the group consisting of hydrogen, halogen, hydroxyl, nitro, trifluoromethyl, trifluoromethoxy, (C1–C6)-straight or branched alkyl, (C2–C6)-straight or branched alkenyl, O—((C1–C4)-straight or branched alkyl), O—((C2–C4)-straight or branched alkenyl), O-benzyl, O-phenyl, 1,2-methylenedioxy, amino, carboxyl and phenyl;

L is U;

M is either oxygen or CH—U;

wherein U is hydrogen, O—((C1–C4)-straight or branched alkyl), O—((C2–C4)-straight or branched alkenyl), (C1–C6)-straight or branched alkyl, (C2–C6)-straight or branched alkenyl, (C5–C7)-cycloalkyl, (C5–C7)-cycloalkenyl substituted with (C1–C4)-straight or branched alkyl or (C2–C4)-straight or branched alkenyl, [(C1–C4)-alkyl or (C2–C4)-alkenyl]-Ar or Ar (Ar as defined above);

J is hydrogen or C1 or C2 alkyl or benzyl;

K is (C1–C4)-straight or branched alkyl, benzyl or cyclohexylmethyl;

m is 0–3; and wherein the stereochemistry at carbon positions 1 and 2 are independently (R) or (S);

provided that if L is hydrogen, then M is CH—U or if M is oxygen then L is not hydrogen.

2. A compound of formula (I):

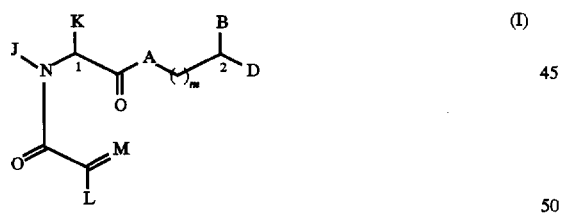

(I)

wherein

A is CH$_2$, oxygen, NH or N—(C1–C4 alkyl);

B and D are independently:

(i) Ar, (C1–C10)-straight or branched alkyl, (C2–C10)-straight or branched alkenyl or alkynyl, (C5–C7)-cycloalkyl-substituted (C1–C6)-straight or branched alkyl or (C2–C6)-straight or branched alkenyl or alkynyl, (C5–C7)-cycloalkenyl-substituted (C1–C6)-straight or branched alkyl or (C2–C6)-straight or branched alkenyl or alkynyl, or Ar-substituted (C1–C6)-straight or branched alkyl or (C2–C6)-straight or branched alkenyl or alkynyl;

wherein, in each case, any one of the CH$_2$ groups of said alkyl, alkenyl or alkynyl chains may be optionally replaced by a heteroatom selected from the group consisting of O, S, SO, SO$_2$; or

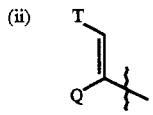

(ii)

wherein Q is hydrogen, (C1–C6)-straight or branched alkyl or (C2–C6)-straight or branched alkenyl or alkynyl;

wherein T is Ar or substituted 5–7 membered cycloalkyl with substituents at positions 3 and 4 which are independently selected from the group consisting of oxo, hydrogen, hydroxyl, O—(C1–C4)-alkyl or O—(C2–C4)-alkenyl;

provided that at least one of B or D is independently selected from the group consisting of (C2–C10)-straight or branched alkynyl, (C5–C7)-cycloalkyl-substituted (C2–C6)-straight or branched alkynyl, (C5–C7)-cycloalkenyl-substituted (C2–C6)-straight or branched alkynyl, and Ar-substituted (C2–C6)-straight or branched alkynyl;

wherein Ar is a carbocyclic aromatic group selected from the group consisting of phenyl, 1-naphthyl, 2-naphthyl, indenyl, azulenyl, fluorenyl, and anthracenyl; or a heterocyclic aromatic group selected from the group consisting of 2-furyl, 3-furyl, 2-thienyl, 3-thienyl, 2-pyridyl, 3-pyridyl, 4-pyridyl, pyrrolyl, oxazolyl, thiazolyl, imidazolyl, pyrazolyl, 2-pyrazolinyl, pyrazolidinyl, isoxazolyl, isothiazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5trithianyl, indolizinyl, indolyl, isoindolyl, 3H-indolyl, indolinyl, benzo[b]furanyl, benzo[b]thiophenyl, 1H-indazolyl, benzimidazolyl, benzthiazolyl, purinyl, 4H-quinolizinyl, quinolinyl, isoquinolinyl, cinnolinyl, phthalazinyl, quinazolinyl, quinoxalinyl, 1,8naphthyridinyl, pteridinyl, carbazolyl, acridinyl, phenazinyl, phenothiazinyl, and phenoxazinyl;

wherein Ar may contain one to three substituents which are independently selected from the group consisting of hydrogen, halogen, hydroxyl, nitro, trifluoromethyl, trifluoromethoxy, (C1–C6)-straight or branched alkyl, (C2–C6)-straight or branched alkenyl, O—((C1–C4)-straight or branched alkyl), O—((C2–C4)-straight or branched alkenyl), O-benzyl, O-phenyl, 1,2-methylenedioxy, amino, carboxyl, N—((C1–C5)-straight or branched alkyl or (C2–C5)-straight or branched alkenyl) carboxamides, N,N-di-((C1–C5)-straight or branched alkyl or (C2–C5)-straight or branched alkenyl)carboxamides, N-morpholinocarboxamide, N-benzylcarboxamide, N-thiomorpholinocarboxamide, N-picolinoylcarboxamide, O—X, CH$_2$—(CH$_2$)$_q$—X, O—(CH$_2$)$_q$—X, (CH$_2$)$_q$—O—X, and CH=CH—X;

wherein X is 4-methoxyphenyl, 2-pyridyl, 3-pyridyl, 4-pyridyl, pyrazyl, quinolyl, 3,5-dimethylisoxazoyl, isoxazoyl, 2-methylthiazoyl, thiazoyl, 2-thienyl, 3-thienyl, or pyrimidyl, and q is 0–2;

L is U;

M is either oxygen or CH—U;

wherein U is hydrogen, O—((C1–C4)-straight or branched alkyl) or O—((C2–C4)straight or branched alkenyl), (C1–C6)-straight or branched alkyl or (C2–C6)-straight or branched alkenyl, (C5–C7)-cycloalkyl or (C5–C7)-cycloalkenyl substituted with (C1–C4)-straight or branched alkyl or (C2–C4)-straight or branched alkenyl, [(C1–C4)-alkyl or (C2–C4)-alkenyl]-Y or Y;

wherein Y is a carbocyclic aromatic group selected from the group consisting of phenyl, 1-naphthyl, 2-naphthyl, indenyl, azulenyl, fluorenyl, and anthracenyl; or a heterocyclic aromatic group as defined above;

wherein Y may contain one to three substituents which are independently selected from the group consisting of hydrogen, halogen, hydroxyl, nitro, trifluoromethyl, trifluoromethoxy, (C1–C6)-straight or branched alkyl, (C1–C6)-straight or branched alkenyl, O—((C1–C4)-straight or branched alkyl), O—((C2–C4)-straight or branched alkenyl), O-benzyl, O-phenyl, 1,2-methylenedioxy, amino, and carboxyl;

J is hydrogen, (C1–C2)-alkyl or benzyl;

K is (C1–C4)-straight or branched alkyl, benzyl or cyclohexylmethyl; and m is 0–3;

provided that if L is hydrogen, then M is CH—U or if M is oxygen, then L is U.

3. A compound of formula (I), as defined in claim 1 or 2, wherein said Ar group may have a hydroxymethyl substituent.

4. The compound according to claim 2, wherein said Ar group contains one to three substituents selected from the group consisting of N—((C1–C5)-straight or branched alkyl or (C2–C5)-straight or branched alkenyl)carboxamides, N,N-di-((C1–C5)-straight or branched alkyl or alkenyl) carboxamides, N-morpholinocarboxamide, N-benzylcarboxamide, N-thiomorpholinocarboxamide, N-picolinoylcarboxamide, O—X, CH$_2$—(CH$_2$)$_q$—X, O—(CH$_2$)$_q$—X, (CH$_2$)$_q$—O—X, and CH=CH—X; wherein X is 4-methoxyphenyl, 2-pyridyl, 3-pyridyl, 4-pyridyl, pyrazyl, quinolyl, 3,5-dimethylisoxazoyl, isoxazoyl, 2-methylthiazoyl, thiazoyl, 2-thienyl, 3-thienyl, or pyrimidyl, and q is 0–2.

5. A method for treating multi-drug resistance in a patient comprising the step of administering to said patient a pharmaceutical composition comprising a pharmaceutically effective amount of a compound and a pharmaceutically acceptable carrier, adjuvant or vehicle, said compound being a compound of formula (I):

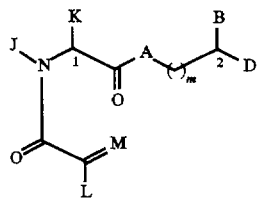

wherein

A is CH$_2$, oxygen, NH or N—(C1–C4 alkyl);

B and D are independently:

(i) hydrogen, Ar, (C1–C10)-straight or branched alkyl, (C2–C10)-straight or branched alkenyl or alkynyl, (C5–C7)-cycloalkyl substituted (C1–C6)-straight or branched alkyl, (C2–C6)-straight or branched alkenyl or alkynyl, (C5–C7)-cycloalkenyl substituted (C1–C6)-straight or branched alkyl, (C2–C6)-straight or branched alkenyl or alkynyl, or Ar substituted (C1–C6)-straight or branched alkyl, (C2–C6)-straight or branched alkenyl or alkynyl;

wherein, in each case, any one of the CH$_2$ groups of said alkyl, alkenyl or alkynyl chains may be optionally replaced by a heteroatom selected from the group consisting of O, S, SO, SO$_2$, N, and NR;

wherein R is selected from the group consisting of hydrogen, (C1–C4)-straight or branched alkyl, (C2–C4)-straight or branched alkenyl or alkynyl, and (C1–C4) bridging alkyl wherein a bridge is formed between the nitrogen and a carbon atom of said heteroatom-containing chain to form a ring, and wherein said ring is optionally fused to an Ar group; or (ii) 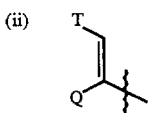

wherein Q is hydrogen, (C1–C6)-straight or branched alkyl or (C2–C6)-straight or branched alkenyl or alkynyl;

wherein T is Ar or substituted 5–7 membered cycloalkyl with substituents at positions 3 and 4 which are independently selected from the group consisting of oxo, hydrogen, hydroxyl, O—(C1–C4)-alkyl, and O—(C2–C4)-alkenyl;

wherein Ar is a carbocyclic aromatic group selected from the group consisting of phenyl, 1-naphthyl, 2-naphthyl, indenyl, azulenyl, fluorenyl, and anthracenyl; or a heterocyclic aromatic group selected from the group consisting of 2-furyl, 3-furyl, 2-thienyl, 3-thienyl, 2-pyridyl, 3-pyridyl, 4-pyridyl, pyrrolyl, oxazolyl, thiazolyl, imidazolyl, pyrazolyl, isoxazolyl, isothiazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, benzo[b]thiophenyl, 1-H-indazolyl, benzimidazolyl, benzthiazolyl, purinyl, 4H-quinolizinyl, quinolinyl, isoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl, and phenoxazinyl;

wherein Ar may contain one to three substituents which are independently selected from the group consisting of hydrogen, halogen, hydroxyl, hydroxymethyl, nitro, trifluoromethyl, trifluoromethoxy, (C1–C6)-straight or branched alkyl, (C2–C6)-straight or branched alkenyl, O—[(C1–C4)-straight or branched alkyl], O—[(C2–C4)-straight or branched alkenyl], O-benzyl, O-phenyl, 1,2-methylenedioxy, amino, carboxyl, N—[(C1–C5)-straight or branched alkyl or (C2–C5)-straight or branched alkenyl) carboxamides, N,N-di-[(C1–C5)-straight or branched alkyl or (C2–C5)-straight or branched alkenyl)]carboxamides, N-morpholinocarboxamide, N-benzylcarboxamide, N-thiomorpholinocarboxamide, N-picolinoylcarboxamide, O—X, CH$_2$—(CH$_2$)$_q$—X, O—(CH$_2$)$_q$—X, (CH$_2$)$_q$—O—X, and CH=CH—X;

wherein X is 4-methoxyphenyl, 2-pyridyl, 3-pyridyl, 4-pyridyl, pyrazyl, quinolyl, 3,5-dimethylisoxazoyl, isoxazoyl, 2-methylthiazoyl, thiazoyl, 2-thienyl, 3-thienyl, or pyrimidyl, and q is 0–2;

L is U;

M is either oxygen or CH—U;

wherein U is hydrogen, O—[(C1–C4)-straight or branched alkyl] or O—[(C2–C4)straight or branched alkenyl], (C1–C6)-straight or branched alkyl or (C2–C6)-straight or branched alkenyl, (C5–C7)-cycloalkyl or (C5–C7)-cycloalkenyl substituted with (C1–C4)-straight or branched alkyl or (C2–C4)-straight or branched alkenyl, [(C1–C4)-alkyl or (C2–C4)-alkenyl]-Y or Y;

wherein Y is selected from the group consisting of phenyl, 1-naphthyl, 2-naphthyl, indenyl, azulenyl, fluorenyl, anthracenyl, 2-pyrrolinyl, 3-pyrrolinyl, pyrolidinyl, 1,3-dioxolyl, 2-imidazolinyl, imidazolidinyl, 2H-pyranyl, 4H-pyranyl, piperidyl, 1,4-dioxanyl, morpholinyl, 1,4-dithianyl, thiomorpholinyl, piperazinyl, quinuclidinyl, and heterocyclic aromatic groups as defined above;

wherein Y may contain one to three substituents which are independently selected from the group consisting of hydrogen, halogen, hydroxyl, hydroxymethyl, nitro, trifluoromethyl, trifluoromethoxy, (C1–C6)-straight or branched alkyl, (C2–C6)-straight or branched alkenyl, O—[(C1–C4)-straight or branched alkyl], O—[(C2–C4)-straight or branched alkenyl], O-benzyl, O-phenyl, 1,2-methylenedioxy, amino, and carboxyl;

J is hydrogen, (C1–C2) alkyl or benzyl;

K is (C1–C4)-straight or branched alkyl, benzyl or cyclohexylmethyl; and m is 0–3;

provided that if L is hydrogen, then M is CH—U or if M is oxygen, then L is U.

6. A method for treating multi-drug resistance in a patient comprising the step of administering to said patient a pharmaceutical composition comprising a pharmaceutically effective amount of a compound and a pharmaceutically acceptable carrier, adjuvant or vehicle, said compound being a compound of formula (I):

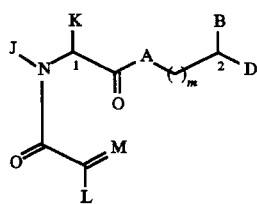

(I)

wherein:

A is CH$_2$, oxygen, NH or N—(C1–C4 alkyl);

B and D are independently:

(i) Ar, (C1–C10)-straight or branched alkyl, (C2–C10)-straight or branched alkenyl or alkynyl, (C5–C7)-cycloalkyl-substituted (C1–C6)-straight or branched alkyl or (C2–C6)-straight or branched alkenyl or alkynyl, (C5–C7)-cycloalkenyl-substituted (C1–C6)-straight or branched alkyl or (C2–C6)-straight or branched alkenyl or alkynyl, or Ar-substituted (C1–C6)-straight or branched alkyl or (C2–C6)-straight or branched alkenyl or alkynyl;

wherein, in each case, any one of the CH$_2$ groups of said alkyl, alkenyl or alkynyl chains may be optionally replaced by a heteroatom selected from the group consisting of O, S, SO, SO$_2$; or (ii) 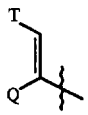

wherein Q is hydrogen, (C1–C6)-straight or branched alkyl or (C2–C6)-straight or branched alkenyl or alkynyl;

wherein T is Ar or substituted 5–7 membered cycloalkyl with substituents at positions 3 and 4 which are independently selected from the group consisting of oxo, hydrogen, hydroxyl, O—(C1–C4)-alkyl or O—(C2–C4)-alkenyl;

wherein Ar is a carbocyclic aromatic group selected from the group consisting of phenyl, 1-naphthyl, 2-naphthyl, indenyl, azulenyl, fluorenyl, and anthracenyl; or a heterocyclic aromatic group selected from the group consisting of 2-furyl, 3-furyl, 2-thienyl, 3-thienyl, 2-pyridyl, 3-pyridyl, 4-pyridyl, pyrrolyl, oxazolyl, thiazolyl, imidazolyl, pyrazolyl, 2-pyrazolinyl, pyrazolidinyl, isoxazolyl, isothiazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, benzo[b]thiophenyl, 1H-indazolyl, benzimidazolyl, benzthiazolyl, purinyl, 4H-quinolizinyl, quinolinyl, isoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl, and phenoxazinyl;

wherein Ar may contain one to three substituents which are independently selected from the group consisting of hydrogen, halogen, hydroxyl, nitro, trifluoromethyl, trifluoromethoxy, (C1–C6)-straight or branched alkyl, (C2–C6)-straight or branched alkenyl, O—((C1–C4)-straight or branched alkyl), O—((C2–C4)-straight or branched alkenyl), O-benzyl, O-phenyl, 1,2-methylenedioxy, amino, carboxyl, N—((C1–C5)-straight or branched alkyl or (C2–C5)-straight or branched alkenyl) carboxamides, N,N-di-((C1–C5)-straight or branched alkyl or (C2–C5)-straight or branched alkenyl)carboxamides, N-morpholinocarboxamide, N-benzylcarboxamide, N-thiomorpholinocarboxamide, N-picolinoylcarboxamide, O—X, CH$_2$—(CH$_2$)$_q$—X, O—(CH$_2$)$_q$—X, (CH$_2$)$_q$—O—X, and CH=CH—X;

wherein X is 4-methoxyphenyl, 2-pyridyl, 3-pyridyl, 4-pyridyl, pyrazyl, quinolyl, 3,5-dimethylisoxazoyl, isoxazoyl, 2-methylthiazoyl, thiazoyl, 2-thienyl, 3-thienyl, or pyrimidyl, and q is 0–2;

L is U;

M is either oxygen or CH—U;

wherein U is hydrogen, O—((C1–C4)-straight or branched alkyl) or O—((C2–C4)-straight or branched alkenyl), (C1–C6)-straight or branched alkyl or (C2–C6)-straight or branched alkenyl, (C5–C7)-cycloalkyl or (C5–C7)-cycloalkenyl substituted with (C1–C4)-straight or branched alkyl or (C2–C4)-straight or branched alkenyl, [(C1–C4)-alkyl or (C2–C4)-alkenyl]-Y or Y;

wherein Y is a carbocyclic aromatic group selected from the group consisting of phenyl, 1-naphthyl, 2-naphthyl, indenyl, azulenyl, fluorenyl, and anthracenyl; or a heterocyclic aromatic group as defined above;

wherein Y may contain one to three substituents which are independently selected from the group consisting of hydrogen, halogen, hydroxyl, nitro, trifluoromethyl, trifluoromethoxy, (C1–C6)-straight or branched alkyl, (C1–C6)-straight or branched alkenyl, O—(C1–C4)-straight or branched alkyl), O—((C2–C4)-straight or branched alkenyl), O-benzyl, O-phenyl, 1,2-methylenedioxy, amino, and carboxyl;

J is hydrogen, (C1–C2)-alkyl or benzyl;

K is (C1–C4)-straight or branched alkyl, benzyl or cyclohexylmethyl; and m is 0–3;

provided that if L is hydrogen, then M is CH—U or if M is oxygen, then L is U.

7. The compound according to claim 1, wherein, in formula (I), at least one of B or D is independently represented by the formula

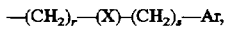
—(CH$_2$)$_r$—(X)—(CH$_2$)$_s$—Ar, wherein r is 0–4;

s is 0–1;

Ar is as defined in claim 1; and each X is independently selected from the group consisting of CH$_2$, O, S, SO, and SO$_2$.

8. A pharmaceutical composition for treatment of multidrug resistance comprising a pharmacetically effective amount of a compound according to any one of claims 1, 2, 4 or 7, a chemosensitizer other than said compound and a pharmaceutically acceptable carrier, adjuvant or vechicle.

9. The pharmaceutical composition according to claim 8, further comprising a chemotherapeutic agent.

10. A method for reducing or, suppressing an immune response in a mammal comprising the step of administering to said mammal a pharmaceutical composition comprising a pharmaceutically effective amount of a compound and a pharmaceutically acceptable carrier, adjuvant of vehicle, said compound being a compound of formula (I) as defined in claim 1 or 2.

11. The method according to claim 10, further comprising the step of administering to said mammal an immunosuppressant selected from the group consisting of cyclosporin A, rapamycin, FK-506, 15-deoxyspergualin, OKT3 and azathioprine.

12. A pharmaceutical composition for treatment of multidrug resistance comprising a pharmaceutically effective amount of a compound according to any one of claims 1–2, or 7 and a pharmaceutically acceptable carrier, adjuvant or vehicle.

13. The pharmaceutical composition according to claim 12, further comprising a chemotherapeutic agent.

14. The method according to claim 10, further comprising the step of administering a steroid to said mammal.

15. A pharmaceutical composition for reduction or suppression of an immune response comprising a pharmaceutically effective of a compound according to any one of claims 1–2, or 7 and a pharmaceutically acceptable carrier, adjuvant or vehicle.

16. The pharmaceutical composition according to claim 15, further comprising an immunosuppressant selected from the group consisting of cyclosporin A, rapamycin, FK-506, 15-deoxyspergualin, OKT3 and azathioprine.

17. The pharmaceutical composition according to claim 16, further comprising an immunosuppressant selected from the group consisting of mycophenolic acid and brequinar.

18. The pharmaceutical composition according to claim 16, further comprising a steroid.

19. The method according to any one of claims 5 or 6, wherein the compound is administered orally.

20. The method according to claim 5 or 6, wherein the compound is not substantially immunosuppressive at the dosage level required to cause chemosensitization.

21. The method according to claim 5 or 6, wherein, in formula (I), at least one of B or D is independently selected from the group consisting of (C2–C10)-straight or branched alkynyl; (C5–C7)-cycloalkyl substituted (C2–C6)-straight or branched alkynyl; (C5–C7)-cycloalkenyl substituted (C2–C6)-straight or branched alkynyl; and Ar substituted (C2–C6)-straight or branched alkynyl.

22. The method according to claim 5 or 6, wherein, in formula (I), at least one of B or D is independently selected from the group consisting of Ar', Ar'-substituted (C1–C6)-straight or branched alkyl, and Ar'-substituted (C2–C6)-straight or branched alkenyl or alkynyl;

wherein Ar' is an Ar group substituted with one to three substituents which are independently selected from the group consisting of N-(straight or branched (C1–C5)-alkyl or (C2–C5)-alkenyl) carboxamides, N,N-di-(straight or branched (C1–C5)-alkyl or (C2–C5)-alkenyl)carboxamides, N-morpholinocarboxamide, N-benzylcarboxamide, N-thiomorpholinocarboxamide, N-picolinoylcarboxamide, O—X, CH$_2$—(CH$_2$)$_q$—X, O—(CH$_2$)$_q$—X, (CH$_2$)$_q$—O—X, and CH=CH—X; wherein X is 4-methoxyphenyl, 2-pyridyl, 3-pyridyl, 4-pyridyl, pyrazyl, quinolyl, 3,5-dimethylisoxazoyl, isoxazoyl, 2-methylthiazoyl, thiazoyl, 2-thienyl, 3-thienyl, or pyrimidyl, wherein q is 0–2.

23. The method according to claim 5, wherein in formula (I), at least one of B or D is independently represented by the formula —(CH$_2$)$_r$—(X)—CH$_2$)$_s$—Ar, wherein:

r is 0–4;

s is 0–1;

Ar is a carbocyclic aromatic group selected from the group consisting of phenyl, 1-naphthyl, 2-naphthyl, indenyl, azulenyl, fluorenyl, and anthracenyl; or a heterocyclic aromatic group selected from the group consisting of 2-furyl, 3-furyl, 2-thienyl, 3-thienyl, 2-pyridyl, 3-pyridyl, 4-pyridyl, pyrrolyl, oxazolyl, thiazolyl, imidazolyl, pyrazolyl, 2-pyrazolinyl, pyrazolidinyl, isoxazolyl, isothiazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, benzo[b]thiophenyl, 1H-indazolyl, benzimidazolyl, benzthiazolyl, purinyl, 4H-quinolizinyl, quinolinyl, isoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl, and phenoxazinyl;

wherein Ar may contain one to three substituents which are independently selected from the group consisting of hydrogen, halogen, hydroxyl, nitro, trifluoromethyl, trifluoromethoxy, (C1–C6)-straight or branched alkyl, (C2–C6)-straight or branched alkenyl, O—((C1–C4)-straight or branched alkyl), O—((C2–C4)-straight or branched alkenyl), O-benzyl, O-phenyl, 1,2-methylenedioxy, amino, carboxyl and phenyl; and each X is independently selected from the group consisting of $CH_2$, O, S, SO, $SO_2$, N, and NR, wherein R is selected from the group consisting of hydrogen, (C1–C4)straight or branched alkyl, (C2–C4)-straight or branched alkenyl or alkynyl, and (C1–C4) bridging alkyl wherein a bridge is formed between the nitrogen atom and the Ar group.

24. The method according to claim 5 or 6, wherein said multi-drug resistance is P-glycoprotein-mediated.

25. The method according to claim 5 or 6, wherein said multi-drug resistance mediated.

26. The pharmaceutical composition according to claim 15, further comprising an immunosuppressant selected from the group consisting of mycophenolic acid and brequinar.

27. The pharmaceutical composition according to claim 15, further comprising a steroid.

28. The method according to claim 10 wherein the compound is administered orally.

* * * * *

UNITED STATES PATENT AND TRADEMARK OFFICE
CERTIFICATE OF CORRECTION

PATENT NO. : 5,723,459
DATED : March 3, 1998
INVENTOR(S) : David M. Armistead, et al.

It is certified that error appears in the above-identified patent and that said Letters Patent is hereby corrected as shown below:

Column 1, line 61 delete "non-P-glycoprtoein" and substitute therefor -- non-P-glycoprotein --.
Column 1, line 62 delete "brast" and substitute therefor -- breast --.
Column 3, line 27 delete "coliris" and substitute therefor -- colitis --.
Columns 8, 9, 11, 13, 15, Table 1 delete " 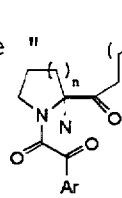 " and substitute therefor -- 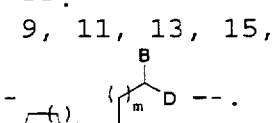 --.

Column 9, Table 1, Cmpd. 22 delete "Tdmethoxyphenyl" and substitute therefor -- Trimethoxyphenyl --.
Column 9, Table 1, Cmpd. 24 delete "3-(4-Mathoxyphenyl)propyl" and substitute therefor -- 3-(4-Methoxyphenyl)propyl --.
Column 9, Table 1, Cmpd. 29 delete "3-(Pyridin-3-yi)propyl" and substitute therefor -- 3-(Pyridin-3-yl)propyl --.
Column 9, Table 1, Cmpd. 31 delete "3-(4-Carboxyphenyi)propyl" and substitute therefor -- 3-(4-Carboxyphenyl)propyl --.
Column 9, Table 1, Cmpd. 38 delete "2-Hydroxypheny" and substitute therefor -- 2-Hydroxyphenyl --.
Column 9, Table 1, Cmpd. 39 delete "Pyridin-3-yi" and substitute therefor -- Pyridin-3-yl --.
Column 13, Table 1, Cmpd. 73 delete "(N-Pyridin-4-y[methoxy)" and substitute therefor --(N-Pyridin-4-ylmethoxy)--.
Column 15, Table 1, Cmpd. 102 delete "3,4-Dimethoxyphe" and substitute therefor -- 3,4-Dimethoxyphenyl --.
Column 19, line 31 delete "intreating of" and substitute therefor -- in treating or --.

UNITED STATES PATENT AND TRADEMARK OFFICE
CERTIFICATE OF CORRECTION

PATENT NO. : 5,723,459
DATED : March 3, 1998
INVENTOR(S) : David M. Armistead, et al.

It is certified that error appears in the above-identified patent and that said Letters Patent is hereby corrected as shown below:

Column 19, line 32, delete "P-glycoprotein-meidated" and substitute therefor -- P-glycoprotein-mediated --.
Column 23, line 39 delete "asteroid," and substitute therefor -- a steroid, --.
Column 27, line 28 delete "ester130" and substitute therefor -- ester 130 --.
Column 28, line 7 delete "cykclohexan-1-ol" and substitute therefor -- cyclohexan-1-ol --.
Column 36, line 41 delete "194" and substitute therefor --164--.
Column 38, line 53, delete "hexame)" and substitute therefor -- hexane) --.
Column 39, line 50 delete "Y1.83(m)," and substitute therefor -- 1.83(m), --.
Column 41, line 57 delete "6" and substitute therefor --$\delta$ --.
Column 42, line 17 delete "6.02-7.24(m)," and substitute therefor -- 6.02-5.99(m), --.
Column 43, line 30 and column 47, line 53 delete "$^1_H$" and substitute therefor -- $^1H$ --.
Column 44, line 22 delete "329-3.18(m)," and substitute therefor -- 3.29-3.18 (m), --.
Column 47, line 7 delete "4.51(d), 4.49(d)," and substitute therefor -- 4.51-4.49(d), --.
Column 47, line 39 delete "5.65(t), 5.61(t)" and substitute therefor -- 5.65-5.61(t) --.
Column 47, line 41 delete "(brd), 4.54(brd)" and substitute therefor -- -4.54(brd) --.
Column 48, line 48 delete "3.11(dr)" and substitute therefor -- 3.11(dt) --.
Column 48, line 67 delete "4.58(m), 4.52(m)" and substitute therefor -- 4.58-4.52(m) --.

UNITED STATES PATENT AND TRADEMARK OFFICE
CERTIFICATE OF CORRECTION

Page 3 of 4

PATENT NO. : 5,723,459
DATED : March 3, 1998
INVENTOR(S) : David M. Armistead, et al.

It is certified that error appears in the above-identified patent and that said Letters Patent is hereby corrected as shown below:

```
Column 49, line 19 delete "5.42(m)," and substitute therefor
-- 5.42-5.37(m), --.
Column 49, line 20 delete "4.38(m)," and substitute therefor
-- 4.38-4.32(m), --.
Column 49, line 22 delete "3.47(m)," and substitute therefor
-- 3.47-3.38(m), --.
Column 50, line 14 delete "3.48(s), 3.40(m)" and substitute
therefor -- 3.48-3.40 (m) --.
Column 51, line 17 delete "3.15(dr)" and substitute therefor
-- 3.15(dt) --.
Column 51, line 39 delete "50 0 MHz" and substitute therefor
-- 500 MHz --.
Column 52, line 36 delete "(50 nM-10NM)" and substitute therefor
-- (50 nM-10mM) --.
Column 53, Table 2, Compd. 15 delete "90  1.4  11.1" and
substitute therefor -- <60  2  >13 --.
Column 53, Table 2, Compd. 55 delete "<60  1.3  >7" and
substitute therefor -- <60  2.25  >15 --.
Table 4 delete "MRP-meidated" and substitute therefor -- MRP-
mediated --.
Column 59, line 33 delete "carboxamides" and substitute therefor
-- carboxamide --.
Column 63, line 49 delete "of" and substitute therefor
-- or --.
Column 64, line 1 after "effective" insert  -- amount --.
```

UNITED STATES PATENT AND TRADEMARK OFFICE
CERTIFICATE OF CORRECTION

PATENT NO. : 5,723,459
DATED : March 3, 1998
INVENTOR(S) : David M. Armistead, et al.

It is certified that error appears in the above-identified patent and that said Letters Patent is hereby corrected as shown below:

Column 64, line 1 after "effective" insert -- amount --.
Column 64, line 44 delete "-$(CH_2)_r$-$(X)$-$CH_2)_s$-Ar," and substitute therefor -- -$(CH_2)_r$-$(X)$-$(CH_2)_s$-Ar, --.
Column 66, line 4 delete "mediated" and substitute therefor -- is MRP-mediated --.

Signed and Sealed this

Thirteenth Day of February, 2001

Attest:

NICHOLAS P. GODICI

Attesting Officer   Acting Director of the United States Patent and Trademark Office